(12) United States Patent
Schwartz et al.

(10) Patent No.: US 7,732,628 B2
(45) Date of Patent: *Jun. 8, 2010

(54) FUNCTIONAL BIOPOLYMER MODIFICATION REAGENTS AND USES THEREOF

(75) Inventors: David A. Schwartz, Encinitas, CA (US); Richard I. Hogrefe, San Diego, CA (US)

(73) Assignee: Solulink Incorporated, San Diego, CA (US)

( * ) Notice: Subject to any disclaimer, the term of this patent is extended or adjusted under 35 U.S.C. 154(b) by 1523 days.

This patent is subject to a terminal disclaimer.

(21) Appl. No.: 10/936,751

(22) Filed: Sep. 8, 2004

(65) Prior Publication Data

US 2005/0203289 A1 Sep. 15, 2005

Related U.S. Application Data

(62) Division of application No. 09/630,060, filed on Aug. 1, 2000, now Pat. No. 7,102,024.

(51) Int. Cl.
C07F 9/02 (2006.01)
(52) U.S. Cl. ..................................................... 558/70
(58) Field of Classification Search ..................... 558/70
See application file for complete search history.

(56) References Cited

U.S. PATENT DOCUMENTS

| | | | |
|---|---|---|---|
| 3,939,123 A | 2/1976 | Matthews et al. | 260/77.5 |
| 4,006,117 A | 2/1977 | Merrifield | 260/45.9 |
| 4,162,355 A | 7/1979 | Tsibris | 526/293 |
| 4,171,412 A | 10/1979 | Coupek et al. | 525/329 |
| 4,175,183 A | 11/1979 | Ayers | 536/57 |
| 4,177,038 A | 12/1979 | Biebricher et al. | 8/192 |
| 4,178,439 A | 12/1979 | Ayers et al. | 536/59 |
| 4,180,524 A | 12/1979 | Reusser et al. | 585/644 |
| 4,241,537 A | 12/1980 | Wood | 47/77 |
| 4,337,063 A | 6/1982 | Mihara et al. | 23/230 |
| 4,404,289 A | 9/1983 | Masuda et al. | 436/538 |
| 4,405,711 A | 9/1983 | Masuda et al. | 435/4 |
| 4,439,585 A | 3/1984 | Gould et al. | 525/127 |
| 4,485,227 A | 11/1984 | Fox | 528/61 |
| 4,507,230 A | 3/1985 | Tam et al. | 260/112.5 |
| 4,569,981 A | 2/1986 | Wenzel et al. | 528/67 |
| 4,683,202 A | 7/1987 | Mullis | 435/91 |
| 4,707,440 A | 11/1987 | Stavrianopoulos | 435/6 |
| 4,833,251 A | 5/1989 | Musso et al. | 548/303 |
| 4,874,813 A | 10/1989 | O'Shannessy | 525/54.1 |
| 4,889,798 A | 12/1989 | Rabbani | 435/6 |
| 4,927,879 A | 5/1990 | Pidgeon | 525/54.1 |
| 4,931,498 A | 6/1990 | Pidgeon | 525/54.1 |
| 5,092,992 A | 3/1992 | Crane et al. | 210/198.2 |
| 5,130,446 A | 7/1992 | Musso et al. | 549/223 |
| 5,151,507 A | 9/1992 | Hobbs, Jr. et al. | 536/23 |
| 5,206,370 A | 4/1993 | Schwartz et al. | 546/281 |
| 5,210,203 A | 5/1993 | Musso et al. | 548/130 |
| 5,237,016 A | 8/1993 | Ghosh et al. | 525/329.4 |
| 5,242,756 A | 9/1993 | Hensel et al. | 428/480 |
| 5,242,796 A | 9/1993 | Prober et al. | 435/6 |
| 5,328,603 A | 7/1994 | Velander et al. | 210/198.2 |
| 5,334,640 A | 8/1994 | Desai et al. | 524/56 |
| 5,389,449 A | 2/1995 | Afeyan et al. | 428/523 |
| 5,403,750 A | 4/1995 | Braatz et al. | 436/531 |
| 5,420,285 A | 5/1995 | Schwartz et al. | 546/281 |
| 5,432,018 A | 7/1995 | Dower et al. | 435/5 |
| 5,474,895 A | 12/1995 | Ishii et al. | 435/6 |
| 5,478,893 A | 12/1995 | Ghosh et al. | 525/329.4 |
| 5,486,616 A | 1/1996 | Waggoner et al. | 548/217 |
| 5,521,290 A | 5/1996 | Sivam et al. | 530/391.5 |
| 5,547,835 A | 8/1996 | Koster | 435/6 |
| 5,547,839 A | 8/1996 | Dower et al. | 435/6 |
| 5,556,752 A | 9/1996 | Lockhart et al. | 435/6 |
| 5,569,587 A | 10/1996 | Waggoner | 435/6 |
| 5,569,766 A | 10/1996 | Waggoner et al. | 548/150 |
| 5,627,027 A | 5/1997 | Waggoner | 435/6 |
| 5,663,242 A | 9/1997 | Ghosh et al. | 525/329.4 |
| 5,679,778 A | 10/1997 | Abrams et al. | 530/391.5 |
| 5,726,329 A | 3/1998 | Jones et al. | 552/105 |
| 5,741,462 A | 4/1998 | Nova et al. | 422/68.1 |
| 5,744,305 A | 4/1998 | Fodor et al. | 435/6 |
| 5,751,629 A | 5/1998 | Nova et al. | 365/151 |
| 5,753,520 A | 5/1998 | Schwartz et al. | 436/542 |
| 5,789,576 A | 8/1998 | Daily et al. | 536/25.6 |
| 5,792,615 A | 8/1998 | Arnold et al. | 435/6 |
| 5,824,473 A | 10/1998 | Meade et al. | 435/6 |
| 5,837,856 A | 11/1998 | Arnold, Jr. et al. | 536/24.5 |
| 5,837,860 A | 11/1998 | Anderson et al. | 536/25.3 |
| 5,854,410 A | 12/1998 | Arnold, Jr. et al. | 536/23.1 |
| 5,856,571 A | 1/1999 | Berninger et al. | 564/37 |
| 5,874,214 A | 2/1999 | Nova et al. | 435/6 |
| 5,874,552 A | 2/1999 | Jones et al. | 536/22.1 |
| 5,876,938 A | 3/1999 | Stolowitz et al. | 435/6 |
| 5,877,220 A | 3/1999 | Schwartz et al. | 514/626 |
| 5,880,270 A | 3/1999 | Berninger et al. | 530/391.1 |
| 5,925,562 A | 7/1999 | Nova et al. | 435/287.1 |

(Continued)

FOREIGN PATENT DOCUMENTS

EP 0361768 A2 9/1989

(Continued)

OTHER PUBLICATIONS

Tsou et al. Journal of Medicinal Chemistry, 1967, 10(4), p. 662-664.*

(Continued)

*Primary Examiner*—Shaojia Anna Jiang
*Assistant Examiner*—Jonathan S Lau
(74) *Attorney, Agent, or Firm*—The Nath Law Group; David B. Waller

(57) ABSTRACT

Hydrazino, oxyamino and carbonyl-based reagents and methods for incorporation into oligonucleotides during their solid phase synthesis are provided. Modified oligonucleotides are provided that incorporate the reagents provided herein. Immobilized oligonucleotides and oligonucleotide conjugates that contain covalent hydrazone or oxime linkages are provided. Methods for preparation of surface bound oligonucleotides are provided. Methods for the preparation of oligonucleotide conjugates are also provided.

11 Claims, 22 Drawing Sheets

U.S. PATENT DOCUMENTS

| | | | | |
|---|---|---|---|---|
| 5,952,172 | A | 9/1999 | Meade et al. | 435/6 |
| 5,955,597 | A | 9/1999 | Arnold, Jr. et al. | 536/24.3 |
| 5,958,901 | A | 9/1999 | Dwyer et al. | 514/75 |
| 5,961,923 | A | 10/1999 | Nova et al. | 422/68.1 |
| 5,972,639 | A | 10/1999 | Parandoosh | 435/29 |
| 6,001,826 | A | 12/1999 | Murrer et al. | 514/183 |
| 6,017,496 | A | 1/2000 | Nova et al. | 422/68.1 |
| 6,020,526 | A | 2/2000 | Schwartz et al. | 564/153 |
| 6,025,129 | A | 2/2000 | Nova et al. | 435/6 |
| 6,028,188 | A | 2/2000 | Arnold, Jr. et al. | 536/25.3 |
| 6,034,135 | A | 3/2000 | Schwartz et al. | 514/616 |
| 6,066,448 | A | 5/2000 | Wohlstadter et al. | 435/6 |
| 6,071,699 | A | 6/2000 | Meade et al. | 435/6 |
| 6,074,823 | A | 6/2000 | Koster | 435/6 |
| 6,087,186 | A | 7/2000 | Cargill et al. | 436/518 |
| 6,217,845 | B1 | 4/2001 | Schwartz et al. | 424/1.69 |

FOREIGN PATENT DOCUMENTS

| | | |
|---|---|---|
| EP | 0384769 A2 | 2/1990 |
| EP | 0384769 B1 | 2/1990 |
| EP | 0772135 A1 | 6/1996 |
| WO | 9815825 | 4/1998 |
| WO | 9831732 | 7/1998 |
| WO | 9965993 A1 | 12/1999 |
| WO | 0004382 | 1/2000 |
| WO | 0004389 | 1/2000 |
| WO | 0004390 | 1/2000 |
| WO | 0008042 A1 | 2/2000 |
| WO | 0040590 A2 | 7/2000 |
| WO | 0040590 A3 | 7/2000 |
| WO | 0109385 A2 | 2/2001 |

OTHER PUBLICATIONS

Garrett et al. Biochemistry, 1999, Saunders College Publishing, 2nd edition, p. 382-384.*
Horwitz et al. J. Med. Chem. 1970, 13(5), p. 1024-1025.*
Bologna et al. Eur. J. Org. Chem. 1999, p. 2353-2358.*
Patani et al. Chem. Rev, 1996, 96, p. 3147-3176.*
"IUPAC-IUB Commission on Biochemical Nomenclature, Abbreviated Nomenclature of Synthetic Polypeptides (Polymerized Amino Acids), Revised Recommendations (1971)," *Biochem*. 11(5): 942-4 (1972).
Abrams et al. "Technetium-99m-Human Polyclonal IgG Radiolabeled via the Hydrazino Nicotinamide Derivative for Imaging Focal Sites of Infection in Rats," *J. Nucl. Med*. 31:2022-8 (1990).
Adleman et al. "Molecular Computation of Solutions to Combinatorial Problems," *Science* 266: 1021-4 (1994).
Agrawal, S. "Importance of nucleotide sequence and chemical modifications of antisense oligonucleotides," *Biochim. Biophys. Acta*. 1489: 53-68 (1999).
Agrawal, S. (Ed.) "Protocols for Oligonucleotides and Analogs," *Methods in Molecular Biology* 20 (Humana Press, 1993).
Berg et al. "Polystyrene-Grafted Polyethylene: Design of Film and felt Matrices for Solid-Phase Peptide Synthesis," *Innovation Perspect Solid Phase Synth. Collect. Pap*., Int. Symp., 1st, Epton R. (Ed.) pp. 453-459 (1989).
Berg et al. "Long-Chain Polystyrene-Grafted Polyethylene Film Matrix: A New Support for Solid-Phase Peptide Synthesis," *J. Am. Chem. Soc*. 111: 8024-6 (1989).
Berg et al. "Peptide Synthesis on Polystyrene-Grafted Polyethylene Sheets," *Pept. Proc. Eur. Pept. Symp*., 20th, Jung, G. et al. (Eds.) pp. 196-198 (1989).
Bielinska et al. "Application of membrane-based dendrimer/DNA complexes for solid phase transfection in vitro and in vivo," *J. Biomaterials* 21: 877-887 (2000).
Blomqvist et al. "Rapid Detection of Human Rhinoviruses in Nasopharyngeal Aspirates by a Microwell Reserve Transcription-PCR-Hybridization Assay," *J. Clin. Microbiol*. 37: 2813-6 (1999).
Brown, M.P. and Royer, C. "Fluorescence spectroscopy as a tool to investigate protein," *Curr. Opin. Biotechnol*. 8: 45-9 (1997).
Browne, D.W. and Dyson, G.M. "The Inhibitory Effect of Substituents in Chemical Reactions. Part III. The Reactivity of the *iso*Thiocyano-group in Substituted Arylthiocarbimides," *J. Chem. Soc*. 178-9 (1934).
Carlsson, B. and Haggblad, J. "Quantitative Determination of DNA-Binding Parameters for the Human Estrogen Receptor in a Solid-Phase Nonseparation Assay," *Anal. Biochem*. 232: 172-9 (1995).
Chen et al. "Stable-Isotope-Assisted MALDI-TOF Mass Spectrometry for Accurate Determination of Nucleotide Compositions of PCR Products," 71: 3118-25 (1999).
Compagno et al. "Antisense Oligonucleotides Containing Modified Bases Inhibit in Vitro Translation of *Leishmania amazonensis* mRNAs by Invading the Mini-exon Hairpin," *J. Biol. Chem*. 274: 8191-8 (1999).
Cristiano, R. J. and Roth, J.A. "Epidermal growth factor mediated DNA delivery into lung cancer cells via the epidermal growth factor receptor," *Cancer Gene Therapy* 3: 4-10 (1996).
Crooke, S.T. "Molecular mechanisms of action of antisense drugs," *Biochim. Biophys. Acta*. 1489: 31-44 (1999).
De Benedetti et al. "DNA chips: the future of biomarkers," *Int. J. Biol. Markers* 15(1): 1-9 (2000).
Earnshaw et al. "Investigation of the Proposed Interdomain Ribose Zipper in Hairpin Ribozyme Cleavage Using 2'-Modified Nucleosides," *Biochemistry* 39: 6410-21 (2000).
Filippov et al. "Solid-Phase Ligation of Synthetic DNA Fragments," *Bioorg Khim*. 16: 1045-51 (1990).
Flanagan et al. "A cytosine analog that confers enhanced potency to antisense oligonucleotides," *Proc. Natl. Acad. Sci. USA* 96: 3513-8 (1999).
Frutos et al. "Enzymatic Ligation Reactions of DNA 'Words' on Surfaces for DNA Computing," *J. Am. Chem. Soc*. 120(40): 10277-82 (1998).
Frutos et al. "Demonstration of a word design strategy for DNA computing on surfaces," *Nucl. Acids Res*. 25: 4748-57 (1997).
Fujita, K. and Silver, J. "Surprising Lability of Biotin-Streptavidin Bond During Transcription of Biotinylated DNA Bound to Paramagnetic Streptavidin Beads," *Biotechniques* 14(4): 608-17 (1993).
Gottschalk et al. "Efficient gene delivery and expression in mammalian cellsusing DNA coupled with perfringolysin O," *Gene Therapy* 2: 498-503 (1995).
Greene, T.W. and Wuts, P.G.M. (Eds.) *Protective Groups in Organic Synthesis* 3rd ed. (J. Wiley & Sons, Inc.) (1999).
Gryaznov, S.M. "Oligonucleotide N3' -> P5' phosphoramidates as potential therapeutic agents," *Biochim. Biophys. Acta* 1489: 131-40 (1999).
Hermanson et al. *Immobilized Affinity Ligand Techniques* (Academic Press, Inc., San Diego) 1992.
Hoganson et al. "Targeted Delivery of DNA Encoding Cytotoxic Proteins through High-Affinity Fibroblast Growth Factor Receptors," *Human Gene Therapy* 9: 2565-75 (1998).
Hostomsky et al. "Solid-phase assembly of DNA duplexes from synthetic oligonucleotides," *Nucl. Acid. Symp. Ser*. 18: 241-244 (1987).
Hultman et al. "Solid-phase cloning to create sublibraries suitable for DNA sequencing," *J. Biotechnol*. 35: 229-38 (1994).
Kaneko et al. "New Hydrazone Derivates of Adriamycin and Their lmmunoconjugates—a Correlation between Acid Stability and Cytotoxicity," *Bioconj. Chem*. 2(3): 133-41 (1991).
Kari, L. "DNA Computing: Arrival of Biological Mathematics," *Mathmatical Intelligencer* 19: 9-22 (1997).
Kent, S.B.H. and Merrifeld, R.B. Preparation and Properties of tert-Butyloxycarbonylaminoacyl-4-(oxymethyl)phenylacetamidomethyl-(Kel F-g-styrene) Resin, an Insoluble, Noncrosslinked Support for Solid Phase Peptide Synthesis, *Isr. J. Chem*. 17: 243-7 (1978).
Kozwich et al. "Development of a Novel, Rapid, Integrated *Cryptosporidium parvum* Detection Assay," *Appl. Environ. Microbiol*. 66(6): 2711-7 (2000).
Lannutti et al. "Probing the Protein—DNA Contacts of a Yeast RNA Polymerase III Transcription Complex in a Crude Extract: Solid Phase Synthesis of DNA Photoaffinity Probes Containing a Novel Photoreactive Deoxycytidine Analog," *Biochemistry* 35: 9821-31 (1996).

Lee et al. "Direct Measurement of the Forces Between Complementary Strands of DNA," *Science* 266: 771-3 (1994).

Lees et al. "Activation of soluble polysaccharides with 1-cyano-4-dimethylaminopyridinium tetrafluoroborate for use in protein-polysaccharide conjugate vaccines and immunological reagents," *Vaccine* 14: 190-8 (1996).

Liu et al. "DNA computing on surfaces," *Nature* 403: 175-9 (2000).

Liu et al. "Progress toward demonstration of a surface based DNA computation: a one word approach to solve a model satisfiability problem," *BioSystems* 52: 25-33 (1999).

Liu et al. "DNA Computing on Surfaces: Encoding Information at the Single Base Level," *J. Comp. Biol.* 5: 269-278 (1998).

Lu et al. " Antisense DNA Delivery In Vivo: Liver Targeting by Receptor-Mediated Uptake," *J. Nucl. Med.* 35:269-75 (1994).

Maeji et al. "Grafted supports used with the multipin method of peptide synthesis," *Reactive Polymers* 22: 203-12 (1994).

Marble et al. "RNA Transcription from Immobilized DNA Templates," *Biotechnol. Prog.* 11: 393-6 (1995).

Merrifeld, R.B. "Solid-Phase Peptide Synthesis. III. An Improved Synthesis of Bradykinin," *Biochemistry* 3: 1385-90 (1964).

Mitchell et al. "Preparation of Aminomethyl-Polystyrene Resin by Direct Amidomethylation," *Tetrahedron Lett.* 42: 3795-8 (1976).

Mitchell, A.R., Kent S.B.H. et al. "A New Synthetic Route to *tert*-Butyloxycarbonylaminoacyl-4-(oxymethyl)phenylacetamidomethl-resin, an Improved Support for Solid-Phase Synthesis," *J. Org. Chem.* 43: 2845-52 (1978).

Morishita, R. "Oligonucleotide-based therapy as a potential new pharmacotherapy," *Folia Pharmacol. Jpn.* (*Nippon Yakurigaku Zasshi*) 115: 123-30 (2000).

Muddiman et al. "Length and Base Composition of PCR-Amplifiedd Nucleic Acids Using Mass Measurements from Electrospray Ionization Mass Spectrometry," *Anal. Chem.* 69(8): 1543-1549 (1997).

Mustajoki et al. "Steady-State Transcript Levels of the Porphobilinogen Deaminase Gene in Patients with Acute Intermittent Porphyria," *Genome Res.* 7: 1054-60 (1997).

Niemeyer et al. "Oligonucleotide-directed self-assembly of proteins: semisynthetic DNA—streptavidin hybrid molecules as connectors for the generation of macroscopic arrays and the construction of supramolecular bioconjugates," *Nucl. Acids Res.* 22(25): 5530-9 (1994).

Perales et al. "An evaluation of receptor-mediated gene transfer using synthetic DNA-ligand complexes," *Eur. J. Biochem.* 226: 255-66 (1994).

Pidgeon et al. "Solid phase membrane mimetics: Immobilized artificial membranes," *Enzyme Microb. Technol.* 12: 149-150 (1990).

Pinkel et al. "Cytogenetic analysis using quantitative, high-sensitivity, fluorescence hybridization," *Proc. Natl. Acad. Sci. USA* 83: 2934-8 (1986).

Powers et al. "Protein Purification by Affinity Binding to Unilamellar Vesicles," *Biotechnol. Bioorg.* 33: 173-82 (1989).

Reed, M.A. and Tror, J.M. "Computing with Molecules," *Scientific American* (Jun. 2000) pp. 86-93.

Roth, A. and Messer, W. "The DNA binding domain of the initiator protein," *EMBO J.* 14: 2106-11 (1995).

Salles et al. "DNA damage excision repair in microplate wells with chemiluminescence detection: Development and perspectives," *Biochimie* 81: 53-8 (1999).

Shafer,D.E., Lees, A. et al. "Activation of soluble polysaccharides with 1-cyano-4-dimethylaminopyridinium tetrafluoroborate (CDAP) for use in protein-polysaccharide conjugates vaccines and immunological reagents. II. Selective crosslinking of proteins to CDAP-activated polysaccharides," *Vaccine* 18: 1273-81 (2000).

Shirota et al. "Regulation of Murine Airway Eosinophilia and Th2 Cells by Antigen-Conjugaed CpG Oligodeoxynucleotides as a Novel Antigen-Specific Immunomodulator," *J. Immunol.* 164: 5575-82 (2000).

Smith et al. "A Surface-Based Approach to DNA Computation," *J. Comp. Biol.* 5(2): 255-67(1998).

Verheijen et al. "Incorporation of a 4-Hydroxy-N-acetylprolinol Nucleotide Analogue Improves the 3'-Exonuclease Stability of 2'-5'-Oligoadenylate-Antisense Conjugates," *Bioorg. Med. Chem. Lett.* 10: 801-4 (2000).

Wang et al. "Surface-based DNA computing operations: DESTROY and READOUT," *BioSystems* 52: 189-91 (1999).

Watkins, T.I. "Trypanocides of the Phenanthridine Series. Part I. The Effect of CHanging the Quarternary Grouping in Dimidium Bromide," *J. Chem. Soc.* pp. 3059-3064 (1952).

Bischoff et al., Introduction of 5'-Terminal Functional Groups into Synthetic Oligonucleotides for Selective Immobilization, *Anal. Biochem.* 164: 336-44 (1987).

Chang et al., Early Results in the International Design of New Bifunctional Chelators, *6th Conference on Radioimmunodetection and Radioimmunotherapy of Cancer—Supplement to Cancer* 80: 2347-53 (1997).

Feinberg et al., A Technique for Radiolabeling DNA Restrictoin Endonuclease Fragments to High Specific Activity, *Analytical Biochemistry* 132: 6-13 (1983).

Frutos et al., Reversible Protection and Reactive Patterning of Amine- and Hydroxyl-Terminated Self-Assembled Monolayers on Gold Surfaces for the Fabrication of Biopolymer Arrays, *Langmuir* 16: 2192-7 (2000).

Ghosh et al., Covalent attachment of oligonucleotides to solid supports, *Nucl. Acids. Res.* 15(3):5353-72 (1987).

Ghosh et al., Synthesis of 5'-Oligonucleotide Hydrazide Derivatives and Their Use in Preparation of Enzyme-Nucleic Acid Hybridization Probes, *Anal. Biochem.* 178: 43-51 (1989).

Hakala et al., Detection of Oligonucleotide Hybridization on a Single Microparticle by Time-Resolved Fluorometry: Hybridization Assays on Polymer Particles obtained by Direct Solid Phase Assembly of the Oligonucleotide Probes, *Bioconjugate Chem.* 8: 378-84 (1997).

Hakala et al., Detection of Oligonucleotide Hybridization on a Single Microparticle by Time-Resolved Fluorometry: Quantiation and Optimization of a Sandwich Type Assay, *Bioconjugate Chem.* 9: 316-21 (1998).

Hogrefe, R.I., An Antisense Oligonucleotide Primer, *Antisense & Nucleic Acid Drug Development* 9: 351-7 (1999).

Hogrefe et al., An Improved Method for the Synthesis and Deprotection of Methylphosphonate Oligonucleotides, *Chapter 7 in Methods in Molecular Biology* vol. 20: *Protocols for Oligonucleotides and Analogs* Agrawal, S. (Ed.) Humana Press Inc., Totowa, NJ. pp. 143-164 (1993).

Hnatowich et al., Comparative Properties of a Technetium-99m-Labeled Single Stranded Natural DNA and a Phosphorothioate Derivative in Vitro and in Mice, *The Journal of Pharmacology and Experimental Therapeutics* 276: 326-34 (1996).

Hnatowich et al., Pharmacokinetics of 99mTc-labeled oligonucleotides, *QJ Nucl. Med.* 40: 202-8 (1996).

Hnatowich et al., Technetium-99m Labeling of DNA Oligonucleotides, *The Journal of Nuclear Medicine* 36(12): 2306-14 (1995).

Kremsky et al., Immobilization of DNA via oligonucleotides containing an aldehyde or carboxylic acid group at the 5' terminus, *Nucl. Acids. Res.* 15(7): 2891-909 (1987).

Kumar et al., Nonradioactive Labeling of Synthetic Oligonucleotide Probes with Terminal Deoxynucleotidyl Transferase, *Analytical Biochemistry* 169: 376-82 (1988).

Reynolds et al., Antisense oligonucleotides containing an internal non-nucleotide-based linker promote site-specific cleavage of RNA, *Nucl. Acids. Res.* 24(4): 760-5 (1996).

Reynolds et al., A Non-Nucleotide-Based Linking Method for the Preparation of Psoralen-Derivatized Methylphosphonate Oligonucleotides, *Bioconjugate Chem.* 3: 366-74 (1992).

Reynolds et al., Synthesis and thermodynamics of oligonucleotides containing chirally pure Rp methylphosphonate linkages, *Nucl. Acids. Res.* 24(22): 4584-91 (1996).

Rigby et al., Labeling Deoxyribonucleic Acid to High Specific Activity in Vitro by Nick Translation with DNA Polymerase I, *J. Mol. Biol.* 113: 237-51 (1977).

Rogers et al., Immobilization of Oligonucleotides onto a Glass Support via Disulfide Bonds: A Method for Preparation of DNA Microarrays, *Anal. Biochem.* 266: 23-30 (1999).

Rusckowski et al., Effect of Endogenous Biotin on the Applications of Streptavidin and Biotin in Mice, *Nuclear Medicine & Biology* 24:263-8 (1997).

Rusckowski et al., Imaging Osteomyelitis with Streptavidin and Indium-111-Labeled Biotin, *J. Nuclear Medicine* 37: 1655-62 (1996).

Rusckowski et al., Pretargeting Using Peptide Nucleic Acid, *6th Conference on Radioimmunodetection and radioimmunotherapy of Cancer—Supplement to Cancer* 80: 2699-705 (1997).

Salo et al., Aminooxy Functionalized Oligonucleotides: Preparation, On-Support Derivatization, and Postsynthetic Attachment to Polymer Support, *Bioconjugate Chem.* 10:815-23 (1999).

Salo et al., Disulfide-Tethered Solid Supports for Synthesis of Photoluminescent Oligonucleotide Conjugates: Hydrolytic Stability and Labeling on the Support, *Bioconjugate Chem.* 9: 365-71 (1998).

Timofeev et al., Regioselective immobilization of short oligonucleotides to acrylic copolymer gels, *Nucl. Acids. Res.* 24(16): 3142-8 (1996).

Trevisiol et al., The Oxyamino-Aldehyde Coupling Reaction: An Efficient Method for the Derivatization of Oligonucleotides, *Tetrahedron Letters* 38(50): 8687-90 (1997).

Trevisiol et al., Synthesis of Nucleoside Triphosphate that Contain an Aminooxy Function for "Post-Ampification Labeling", *Eur. J. Org. Chem.* pp. 211-217 (2000).

* cited by examiner hydrazine semicarbazide carbazide hydrazide thiosemicarbazide thiocarbazide carbonic acid dihydrazine hydrazine carboxylate hydrazine X = NH
oxyamino X = O carbonyl hydrazone X = NH
oxime X = O R = hydrogen, or aliphatic, aromatic, or heteroaromatic moiety

```
                        SEQUENCE LISTING

<160> NUMBER OF SEQ ID NOS: 5

<210> SEQ ID NO 1
<211> LENGTH: 25
<212> TYPE: DNA
<213> ORGANISM: Artificial Sequence
<220> FEATURE:
<223> OTHER INFORMATION: Synthetic olignucleotide

<400> SEQUENCE: 1 ttttttagc ctaactgatg ccatg                                          25

<210> SEQ ID NO 2
<211> LENGTH: 25
<212> TYPE: DNA
<213> ORGANISM: Artificial Sequence
<220> FEATURE:
<221> NAME/KEY: misc_feature
<222> LOCATION: 1
<223> OTHER INFORMATION: n = thymidine 6-(4-formylbenzoylamino)hexyl
      phosphodiester

<400> SEQUENCE: 2
nttttttagc ctaactgatg ccatg                                         25

<210> SEQ ID NO 3
<211> LENGTH: 18
<212> TYPE: DNA
<213> ORGANISM: Artificial Sequence
<220> FEATURE:
<221> NAME/KEY: misc_feature
<222> LOCATION: 1
<223> OTHER INFORMATION: n = fluorescein bound cytidine at 5' end to
      form fluorescein-oligonucleotide conjugate

<400> SEQUENCE: 3
natggcatca gttacgct                                                 18

<210> SEQ ID NO 4
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 4
```

```
aacttaggac acgttacg                                    18

<210> SEQ ID NO 5
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 5
cgtaacgtgt cctaagtt                                    18
```

FUNCTIONAL BIOPOLYMER MODIFICATION REAGENTS AND USES THEREOF

RELATED APPLICATIONS

This application is a divisional of patent application Ser. No. 09/630,060 entitled "FUNCTIONAL BIOPOLYMER MODIFICATION REAGENTS AND USES THEREOF" TO Schwartz et al. filed 1 Aug. 2000 now U.S. Pat. No. 7,102,024 and is related to co-owned United States utility patent application entitled "TRIPHOSPHATE OLIGONUCLEOTIDE MODIFICATION REAGENTS AND USES THEREOF", to Schwartz et al., filed 1 Aug. 2000; and to U.S. patent application Ser. No. 09/815,978, entitled "HYDRAZINE-BASED AND CARBONYL-BASED BIFUNCTIONAL CROSSLINKING REAGENTS", to Schwartz, D. filed 22 Mar. 2000. The above-referenced applications are incorporated herein by reference in their entirety.

FIELD OF THE INVENTION

The field of invention relates to the preparation reagents and methods for preparation of modified biopolymers, and to methods and reagents for preparing immobilized biopolymers and also for preparing conjugates of biopolymers.

BACKGROUND OF THE INVENTION

Oligonucleotides functionalized 3', 5' or internally with reactive moieties have been used for a variety of therapeutic and diagnostic purposes. For example, modified oligonucleotides incorporating targeting moieties have been prepared to increase activity of antisense oligonucleotides for therapy. Functionalized or modified oligonucleotides have been prepared to permit conjugation to supports and also for preparation of conjugates.

Methods have been described for achieving these purposes, but in many cases these methods have inherent disadvantages and do not satisfy all the criteria required by currently developing technologies. Methods in which a functional moiety can be incorporated into an oligonucleotide during its synthesis on a solid support are limited. There is a need to develop methods to site-specifically bind oligonucleotides to surfaces for a variety of purposes, such as for identification of genes for pharmacogenomic, diagnostic and therapeutic purposes.

Functional groups that can be added directly to a growing oligonucleotide on a solid support include amines and thiols. Direct binding of amino or thiol-functionalized oligonucleotides to solid surfaces require that the surface be modified with a moiety that reacts directly with an amino or thiol function. The reactive moieties succinimidyl esters and maleimides have been used for this purpose. The coupling efficiency of these moieties suffers from their inherent instability and ease of hydrolysis (for maleimides and succinimidyl esters).

Biotin monomers that can be added to the 5'-end of an oligonucleotide on a solid support have been described, as well as coupling of biotinylated oligonucleotides to surfaces and other molecules that have been modified to incorporate either avidin or streptavidin protein. This method is functional but requires the use of a protein that is expensive, may lead to non-specific binding, and has at most four biotin binding sites per molecule. Also, incorporation of large molecules on biotin reduces the binding affinity and the number of accessible binding sites on avidin. The density of oligonucleotide per $mm^2$ is limited due to the use of a protein having a molecular weight of about 14000.

These same limitations exist for the preparation of oligonucleotide conjugates. The incorporation of activated functionalities, such as succinimidyl esters or maleimides, of the conjugation partner (compound to be conjugated to the oligonucleotide) can be costly, and not even possible in some instances.

Table 1 below lists the available reactive couples to bind oligonucleotides to solid surfaces.

TABLE 1

| 5'-oligonucleotide modification | Surface modification |
|---|---|
| amino | N-hydroxysuccinimidyl ester (NHS), isothiocyanates (ITC) |
| thiol | Maleimide, bromoacetyl, activated thiol (to form disulfide) |
| disulfide | thiol |
| biotin | avidin |

Due to the limitations of available methods, there is a need for efficient crosslinking agents for immobilization of oligonucleotides on solid surfaces, and for preparation of biopolymer conjugates.

Therefore, it is an object herein to provide reagents and methods for immobilization of oligonucleotides on solid surfaces without the need for post-synthetic modification of the oligonucleotide. It is also an object herein to provide reagents and methods for synthesis of biopolymer conjugates, including oligonucleotide, protein, oligosaccharide, glycoprotein and/or protein nucleic acid (PNA) conjugates. A further object herein is to provide modified, immobilized or conjugated oligonucleotides.

SUMMARY OF THE INVENTION

Reagents and methods for immobilization and conjugation of biopolymers, particularly oligonucleotides (a "first component"), are provided. The reagents are bifunctional phosphorous-containing monomers that are incorporated into an oligonucleotide during standard solid phase synthesis. The resulting modified first component is then conjugated to a second component. The reagents possess a phosphorous based coupling group that can be coupled at the 5' or 3' terminus of an oligonucleotide, preferably at the 5' terminus. Alternatively, the reagents can be incorporated at an internal position in the oligonucleotide, thus forming an oligonucleotide analog.

The reagents provided herein also are useful as mass modification reagents in DNA sequencing (see, e.g., U.S. Pat. Nos. 6,074,823 and 5,547,835). The reagents can be incorporated into oligonucleotides for the accurate determination of base composition (Muddiman et al. (1997) *Anal. Chem.* 69:1543), and for the scoring of single nucleotide polymorphisms (SNPs) (Chen et al. (1999) *Anal. Chem.* 71:3118). The reagents also can be used to study the mechanisms by which ribozymes effect catalytic cleavage (Earnshaw et al. (2000) *Biochemistry* 39:6410). The reagents can be incorporated into antisense oligonucleotides to increase their resistance to enzymatic degradation (Verheijen et al. (2000) *Bioorg. Med. Chem. Lett.* 10:801), their overall potency (Flanagan et al. (1999) *Proc. Natl. Acad. Sci. USA* 96:3513) and the stability of their hybrids with the complementary RNA sequences (Compagno et al. (1999) *J. Biol. Chem.* 274:8191).

Phosphorous based coupling groups for use in the reagents and methods herein are well known to those of skill in the art.

In certain embodiments herein, the phosphorous based coupling groups include, but are not limited to, phosphoramidites, phosphonamidites, H-phosphonates and phosphotriesters. As provided herein, the phosphorous-based coupling group forms linking groups with the oligonucleotides. Such linking groups include, but are not limited to, phosphorodithioates, phosphorothioates, phosphoramidates, phosphonates, phosphodiesters, phosphotriesters, thiophosphoramidates, thionoalkylphosphonates, thionoalkylphosphotriesters or boranophosphates. Preferred phosphorous based coupling groups are phosphoramidites and preferred linking groups are phosphodiesters. In particular, β-cyanoethyl-N,N-diisopropylphosphoramidite groups can be used in the reagents and methods provided herein.

The reagents also possess, in addition to the phosphorous based coupling group, a protected hydrazino, protected oxyamino (—O—NH$_2$), or carbonyl moiety for formation of a hydrazone or oxime linkage with an appropriately modified second component. The hydrazino moiety is an aliphatic, aromatic or heteroaromatic hydrazine, semicarbazide, carbazide, hydrazide, thiosemicarbazide, thiocarbazide, carbonic acid dihydrazine or hydrazine carboxylate (see, e.g., FIG. 1). The protecting groups are salts of the hydrazino or oxyamino group, including but not limited to, mineral acids salts, such as but not limited to hydrochlorides and sulfates, and salts of organic acids, such as but not limited to acetates, lactates, malates, tartrates, citrates, ascorbates, succinates, butyrates, valerates and fumarates, or any amino or hydrazino protecting group known to those of skill in the art (see, e.g., Greene et al. (1999) *Protective Groups in Organic Synthesis* (3rd Ed.) (J. Wiley Sons, Inc.)). The carbonyl moiety is any carbonyl containing group capable of forming a hydrazone or oxime linkage with one or more of the above hydrazino or oxyamino moieties. Preferred carbonyl moieties include aldehydes and ketones.

For incorporation at an internal position in the oligonucleotide, the reagents provided herein also possess a group, such as a hydroxyl group or other group that provides a site for oligonucleotide synthesis. An hydroxyl group or other such group provides a site for continuing the oligonucleotide synthesis. The hydroxyl group of the reagent is preferably a primary alcohol or a functional equivalent thereof, including a free OH group or such group ppropriately protected for use in solid phase oligonucleotide synthesis. For example, the hydroxyl group may be protected as the corresponding monomethoxytrityl (MMT) ether. In these embodiments, the hydrazino or oxyamino group, if present, is protected with a group that is orthogonal to an MMT ether (i.e., that is not removed under conditions where an MMT ether is cleaved, but is removed under conditions where an MMT ether is stable). Groups that are orthogonal to an MMT ether include, but are not limited to, carbamates, including 9-fluorenylmethoxycarbonyl (FMOC) carbamates.

Alternatively, a phosphoramidite monomer containing two orthogonally-protected alcohols can be used in the oligonucleotide synthesis. One of the protecting groups is amenable to standard oligonucleotide synthesis. Following oligonucleotide synthesis incorporating the monomer at an internal position of the oligonucleotide; the orthogonal protecting group is removed to afford a free alcohol. Reaction of this alcohol with a reagent of formula (I) provides the desired hydrazino, oxyamino, or carbonyl modified oligonucleotide. In one embodiment, the protecting group amenable to oligonucleotide synthesis is an MMT ether, and the other is a protecting group that is orthogonal to MMT ether including, but not limited to, a carbonate such as an FMOC carbonate. Phosphoramidites containing two orthogonally-protected alcohols are commercially available (see, e.g., "Asymmetric Doubler Phosphoramidite", Glen Research Corporation, Sterling, Va.).

In another alternative, a hydroxyl-substituted nucleoside, preferably possessing the hydroxy group on the nucleobase, is incorporated into the oligonucleotide during standard synthesis. The hydroxyl group is preferably protected with a group that is orthogonal to protecting groups amenable to oligonucleotide synthesis. Such groups include, but are not limited to, carbonates such as an FMOC carbonate. Following oligonucleotide synthesis, the protecting group is removed and the resulting free alcohol is reacted with a reagent of formula (I) to provide a hydrazino, oxyamino, or carbonyl modified oligonucleotide. In one embodiment, the hydroxy substituted nucleoside is a 5'-(O-MMT)-5-substituted cytosine possessing an FMOC protected hydroxyl group on the 5-substituent.

In another embodiment, the reagents possess a protected amino or protected hydroxyl group, in addition to a protected hydrazino group or a protected oxyamino group, and a phosphorous based coupling group. The protected amino or protected hydroxyl group provides a site for conjugation of a second component. Of particular interest in these embodiments are second components that do not possess substantial fluorescence in the absence of intercalation into a DNA double helix. The second component in this embodiment is preferably an ethidium bromide analog.

In one embodiment, the reagents for use in the methods provided herein have formula (I):

or a derivative thereof, as defined herein, where $P^1$ is a phosphorous based coupling group, as defined herein; X is a protected hydrazino group, a protected oxyamino group, or a carbonyl derivative, where the protecting group is a salt or any amino or hydrazino protecting group known to those of skill in the art; and M is a divalent group having any combination of the following groups, which are combined in any order: arylene, heteroarylene, cycloalkylene, $C(R^1)_2$, —$C(R^1)$=$C(R^1)$—, >$C$=$C(R^2)(R^3)$, >$C(R^2)(R^3)$, —C≡C—, O, $S(A)_a$, $P(D)_b(R^1)$, $P(D)_b(ER^1)$, $N(R^1)$, >$N^+(R^2)(R^3)$ and C(E); where a is 0, 1 or 2; b is 0, 1, 2 or 3; A is O or $NR^1$; D is S or O; and E is S, O or $NR^1$; each $R^1$ is a monovalent group independently selected from hydrogen and $M^1$-$R^4$; each $M^1$ is a divalent group independently having any combination of the following groups, which groups are combined in any order: a direct link, arylene, heteroarylene, cycloalkylene, $C(R^5)_2$, —$C(R^5)$=$C(R^5)$—, >$C$=$C(R^2)(R^3)$, >$C(R^2)(R^3)$, —C≡C—, O, $S(A)_a$, $P(D)_b(R^5)$, $P(D)_b(ER^5)$, $N(R^5)$, $N(COR^5)$, >$N^+(R^2)(R^3)$ and C(E); where a is 0, 1 or 2; b is 0, 1, 2 or 3; A is O or $NR^5$; D is S or O; and E is S, O or $NR^5$; $R^4$ and $R^5$ are each independently selected from the group among hydrogen, halo, pseudohalo, cyano, azido, nitro, $SiR^6R^7R^8$, alkyl, alkenyl, alkynyl, haloalkyl, haloalkoxy, aryl, aralkyl, aralkenyl, aralkynyl, heteroaryl, heteroalkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy and $NR^9R^{10}$; $R^9$ and $R^{10}$ are each independently selected from hydrogen, alkyl, alkenyl, alkynyl, cycloalkyl, aryl, aralkyl, heteroaryl, heteroaralkyl and heterocyclyl; $R^2$ and $R^3$ are selected from (i) or (ii) as follows: (i) $R^2$ and $R^3$ are independently selected from among hydrogen, alkyl, alkenyl, alkynyl, cycloalkyl, aryl and heteroaryl; or (ii) $R^2$ and $R^3$ together form alkylene, alkenylene or cycloalkylene; $R^6$, $R^7$ and $R^8$ are each independently a monovalent group selected from hydrogen, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy and $NR^9R^{10}$; and $R^1, R^2, R^3, R^4, R^5, R^6, R^7, R^8, R^9$ and $R^{10}$ can be substituted with one or more substituents each independently selected from Z, wherein Z is selected from alkyl, alkenyl, alkynyl, aryl, cycloalkyl, cycloalkenyl, hydroxy, $S(O)_hR^{20}$, $NR^{20}R^{21}$, $COOR^{20}$, $COR^{20}$, $CONR^{20}R^{21}$, $OC(O)NR^{20}R^{21}$, $N(R^{20})C(O)R^{21}$, alkoxy, aryloxy, heteroaryl, heterocyclyl, heteroaralkoxy, heterocyclyloxy, aralkyl, aralkenyl, aralkynyl, heteroaralkyl, heteroaralkenyl, heteroaralkynyl, aralkoxy, heteroaralkoxy, alkoxycarbonyl, carbamoyl, thiocarbamoyl, alkoxycarbonyl, carboxyaryl, halo, pseudohalo, haloalkyl and carboxamido; h is 0, 1 or 2; and $R^{20}$ and $R^{21}$ are each independently selected from among hydrogen, halo, pseudohalo, cyano, azido, nitro, trialkylsilyl, dialkylarylsilyl, alkyldiarylsilyl, triarylsilyl, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy, amino, amido, alkylamino, dialkylamino, alkylarylamino, diarylamino and arylamino.

In certain embodiments, particularly when X is a protected oxyamino group, the M group is not tetra(ethyleneoxy) (i.e., $(CH_2CH_2O)_4$, TEG). In other embodiments, when X is a protected oxyamino group, it does not substitute the 2', 3' or 5', particularly the 2', position of a nucleoside, nucleotide, or analog thereof. In particular embodiments herein, particularly when X is an aldehyde group, a protected hydrazine group, or a protected oxyamino group, the X group does not substitute the nucleobase of a nucleoside, nucleotide or analog thereof.

In another embodiment, the reagents for use in the methods provided herein have formula (VIII):

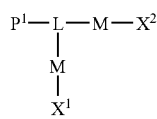

or a derivative thereof, where $P^1$ is selected as above; each M is independently selected as above; L is a trivalent group having any combination of the following groups: arylene, heteroarylene, cycloalkylene, $C(R^1)_2$, $—C(R^1)=C(R^1)—$, $—C\equiv C—$, O, $S(A)_a$, $P(D)_b(R^1)$, $P(D)_b(GR^1)$, $N(R^1)$, $>N^+(R^2)(R^3)$, $C(R^{40})_2$, $C(R^1)(R^{40})$, $—C(R^{40})=C(R^1)—$, $—C(R^{40})=C(R^{40})—$, $S(NR^{40})$, $P(D)_b(R^{40})$, $P(D)_b(GR^{40})$, $N(R^{40})$ or C(G); where a is 0, 1 or 2; b is 0, 1, 2 or 3; A is O or $NR^1$; D is S or O; and G is S, O, $NR^1$ or $NR^{40}$; which groups are combined in any order; $R^1, R^2$ and $R^3$ are as defined above; each $R^{40}$ is a divalent group independently having any combination of the following groups: arylene, heteroarylene, cycloalkylene, $C(R^5)_2$, $—C(R^5)=C(R^5)—$, $—C\equiv C—$, O, $S(A)_a$, $P(D)_b(R^5)$, $P(D)_b(GR^5)$, $N(R^5)$, $N(COR^5)$, $>N^+(R^2)(R^3)$, $C(R^{41})_2$, $C(R^5)(R^{41})$, $—C(R^4)=C(R^5)—$, $S(NR^{41})$, $P(D)_b(R^{41})$, $P(D)_b(GR^{41})$, $N(R^{41})$, $N(COR^{41})$ or C(G); where a is 0, 1 or 2; b is 0, 1, 2 or 3; A is O or $NR^5$; D is S or O; and G is S, O, $NR^5$ or $NR^{41}$; which groups are combined in any order; each $R^{41}$ is a divalent group and each is independently selected from alkylene, alkenylene, alkynylene, arylene, heteroarylene, heterocyclylene, cycloalkylene, cycloalkenylene, alkylenoxy, arylenoxy, aralkylene, aralkenylene, aralkynylene, heteroaralkylene, heteroaralkenylene, heteroaralkynylene, aralkylenoxy, and heteroaralkylenoxy; $X^1$ is a protected hydrazino or a protected oxyamino group; and $X^2$ is an orthogonally protected amino or orthogonally protected hydroxyl group.

In another embodiment, the reagents for use in the methods provided herein have formula (X):

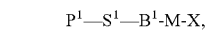

or a derivative thereof, as defined herein, where $P^1$, M and X are selected as above; $S^1$ is a ribose, a deoxyribose or a dideoxyribose; and $B^1$ is a nucleobase. In these embodiments, it is preferred that $P^1$ is attached to the 3'-hydroxyl of $S^1$. The 5'-hydroxyl group of $S^1$ is preferably protected with a group amenable to solid phase oligonucleotide synthesis, including, but not limited to, a monomethoxytrityl (MMT) or a dimethoxytrityl (DMT) group. In the compounds of formula (X), the variable X, in addition to the groups recited above, is selected from protected hydroxy or protected amino groups, where the protecting group is orthogonal to the protecting group on the 5'-hydroxyl of $S^1$. Such orthogonal protecting groups include, but are not limited to, carbamates and carbonates, particularly 9-fluorenylmethoxycarbonyl (FMOC) carbamates and carbonates. Removal of the orthogonal protecting group following oligonucleotide synthesis provides a free hydroxy or amino group. Reaction of this free hydroxy or amino group with a reagent of formula (I) affords certain of the oligonucleotides provided herein modified with a hydrazino, oxyamino or carbonyl moiety at an internal position.

Biopolymers, including oligonucleotides, that are modified by incorporation of the above monomers are provided. Thus, in certain embodiments, provided herein are oligonucleotide analogs of formula (II):

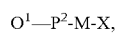

or a derivative thereof, where $O^1$ is a first component that is an oligonucleotide or analog thereof, such as a protein nucleic acid (PNA); $P^2$ is a phosphorous based linking group, including, but not limited to, a phosphorodithioate, phosphorothioate, phosphoramidate, phosphonate, phosphodiester, phosphotriester, thiophosphoramidate, thionoalkylphosphonate, thionoalkylphosphotriester or boranophosphate group, preferably a phosphodiester group, resulting from the coupling of a compound of formula (I) with the oligonucleotide or analog thereof; and M and X are as defined above. In these embodiments, X also includes the free hydrazino and oxyamino groups resulting from deprotection.

In certain embodiments, the oligonucleotide analogs of formula (II) are selected with the proviso that if X is CHO, then M is not undecylenecarbonylaminomethylene ($n-C_{11}H_{22}C(O)NHCH_2$) or $C_{1-20}$alkylene. In other embodiments, the oligonucleotide analogs are of formula (II) where X is not an oxyamino or protected oxyamino group. In further embodiments, the oligonucleotide analogs are of formula (II) where X is not a hydrazide ($—C(O)—NHNH_2$) group. In particular embodiments, the oligonucleotide analogs of formula (II) are selected with the proviso that if X is $—NHNH_2$, then M is not $—CH(CH_2OH)(CH_2)_6NHCO$-5-pyrid-2-ylene. In other embodiments, the oligonucleotide analogs of formula (II) are selected with the proviso that $P^2$ is not a phosphoramidate group.

In another embodiment, provided herein are oligonucleotide analogs of formula (IX):

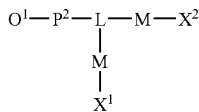

or a derivative thereof, where $O^1$, $P^2$, L, $X^1$ and $X^2$ are selected as above; and each M is independently selected as above. In these embodiments, $X^1$ also includes the free hydrazino and oxyamino groups resulting from deprotection. $X^2$ also includes the free amino or hydroxy group resulting from deprotection.

In another embodiment, oligonucleotide analogs of formula (XI) are provided:

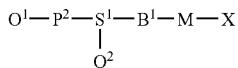

or a derivative thereof, where $O^1$, $P^2$, $S^1$, $B^1$, M and X are selected as above; and $O^2$ is an oligonucleotide, or analog thereof such as a PNA. In these embodiments, X also includes the free hydrazino and oxyamino groups resulting from deprotection.

Such oligonucleotide analogs are useful as antisense drugs, cis-elements acting as regulators of gene expression, and substrates for RNA binding proteins such as HIV-1 Rev and Tat (see, e.g., Agrawal (1999) *Biochim. Biophys. Acta* 1489: 53; Crooke (1999) *Biochim. Biophys. Acta* 1489:31; Gryaznov (1999) *Biochim. Biophys. Acta* 1489:131; and Morishita (2000) *Nipp. Yakuri. Zass.* 115:123).

Oligonucleotides covalently immobilized on a solid surface are also provided. The oligonucleotides are of formula (II), (IX) or (XI), and are immobilized through a covalent hydrazone or oxime linkage. Solid surfaces for use in this embodiment are any know to those of skill in the art to be suitable for immobilization of biopolymers.

The solid surface is modified to possess a hydrazino, oxyamino, or carbonyl group that is complementary to the hydrazino, oxyamino or carbonyl moiety of the oligonucleotide of formula (II), (IX) or (XI) for formation of a hydrazone or oxime linkage. In preferred embodiments, the oligonucleotides are immobilized through a covalent hydrazone linkage.

The immobilized oligonucleotides are useful for a variety of purposes known to those of skill in the art, including, but not limited to, diagnostic probe assays, DNA amplification by solid phase polymerase chain reactions (PCR), molecular computing (see, e.g., Adleman (1994) *Science* 266:1021-1024; Kari (1997) *Mathematical Intelligencer* 19:9-22; Frutos et al. (1997) *Nucleic Acids Res.* 25:4748; Smith et al. (1998) *J. Comp. Biol.* 5:255; Liu et al. (1998) *J. Comp. Biol.* 5:267; Frutos et al. (1998) *J. Am. Chem. Soc.* 120:10277; Wang et al. (1999) *Biosystems* 52:189-191; Liu et al. (1999) *Biosystems* 52:25-33; Liu et al. (2000) *Nature* 403:175-179; European Patent Application Publication No. EP 0 772 135; Reed et al. (June 2000) *Scientific American*: 86-93), molecular addressing (Niemeyer et al. (1994) *Nucl. Acids Res.* 22(25):5530-5539), DNA sequencing by mass spectrometry (see, e.g., U.S. Pat. Nos. 6,074,823 and 5,547,835) and in studying the molecular electronics of DNA (see, e.g., U.S. Pat. Nos. 6,071,699, 6,066,448, 5,952,172 and 5,824,473).

The immobilized oligonucleotides also can be used, for example, in PCR-based solid phase sequencing methods (Mustajoki et al. (1997) *Genome Res.* 7:1054). They also can be used to measure the interaction forces between single strands of DNA (Lee et al. (1994) *Science* 266:771), in solid phase-mediated transfection of oligonucleotides (Bielinska et al. (2000) *J. Biomaterials* 21:877), and in solid phase cloning to create libraries suitable for direct solid phase sequencing (Hultman et al. (1994) *J. Biotechnol.* 35:229). The immobilized oligonucleotides also can be used in DNA chip technology to create arrays of oligonucleotides, such as chips used to compare the qualitative and quantitative characteristics of gene expression profiles, mutations, insertions and deletions in normal and diseased states (De Benedetti et al. (2000) *Int. J. Biol. Markers* 15:1). They also can be used to identify and characterize the DNA binding site of DNA binding proteins (Roth et al. (1995) *EMBO J.* 14:2106; Carlsson et al. (1995) *Anal. Biochem.* 232:172). Immobilized oligonucleotides bound, for example to Sephacryl S-500 particles via a CNBr-activation procedure can be used to assemble extended DNA duplexes by phosphorylation, and ligation and restriction enzyme digestion of assemblies of annealed oligonucleotides in solid phase (Hostomsky et al. (1987) *Nucleic Acids Symp. Ser.* 18:241). The immobilized oligonucleotides also can be used in PCR, RT-PCR (Kozwich et al. (2000) *Appl. Environ. Microbiol.* 66:2711; Blomqvist et al. (1999) *J. Clin. Microbiol.* 37:2813), transcription (Marble et al. (1995) *Biotechnol. Prog.* 11:393; Fujita et al. (1993) *Biotechniques* 14:608), ligation reactions (Filippov et al. (1990) *Bioorg. Khim.* 16:1045), and in studying DNA repair mechanisms (Salles et al. (1999) *Biochimie* 81:53).

In embodiments where X of the modified oligonucleotide is a hydrazino or oxyamino group, the solid surface also can be modified to possess an epoxide, α-bromocarbonyl, maleimide, maleic anhydride, isothiocyanate or isocyanate group. Such solid surfaces can be prepared by methods provided herein or other methods well known to those of skill in the art. For example, reaction of pentafluorophenyl 4-isothiocyanatobenzoate with an amino or hydroxy solid surface results in formation of an isothiocyanato modified solid surface. Some of these surfaces are commercially available from, e.g., Pierce (Rockford, Ill.), SINTEF Applied Chemistry (Trondheim, Norway), Rapp Polymere Gmbh (Tubingen, Germany), and Dyno Particles AS (Trondheim, Norway). Reaction of the hydrazino or oxyamino group of the modified oligonucleotide with the epoxide, α-bromocarbonyl, maleimide, maleic anhydride, isothiocyanate or isocyanate group of the solid surface results in covalent attachment of the oligonucleotide to the solid surface.

In certain embodiments, particularly where X is an oxyamino group, the immobilized oligonucleotides are selected such that the solid surface is not modified with an aldehyde or epoxide group.

Oligonucleotide conjugates are provided. The conjugates are prepared from the modified oligonucleotides of formula (II), (IX) or (XI). The modified oligonucleotide of formula (II), (IX) or (XI) is reacted with a complementary derivative of a second component to form a hydrazone or oxime covalent linkage. Second components for use herein include, but are not limited to, biopolymers as defined herein, macromolecules as defined herein, polymers including, but not limited to, polyamines, polyamides, polyethers and polyethylene glycols, and other compounds of interest herein for use in assays, kits, diagnostic arrays, including, but not limited to, intercalators, vitamins, reporter molecules, cholesterols, phospholipids, biotin, phenazine, phenanthridine, anthraquinone, acridine, fluoresceins, rhodamines, coumarins, dyes, antibodies, haptens, antigens, enzymes, and detection reagents including, but not limited to, fluorophores, metals including, but not limited to, gold, metal chelates, chromophores, fluorophore precursors and chromophore precursors, that possess or are modified to possess a hydrazino, oxyamino or carbonyl group that is complementary to the carbonyl, oxyamino or hydrazino group of the oligonucleotide of formula (II), (IX) or (XI) for formation of hydrazone or oxime linkage. Fluorophore precursors and chromophore precursors are compounds that react with the hydrazino, oxyamino or carbonyl group of the modified oligonucleotide to form a fluorogenic or chromogenic group for analysis. Such groups are preferred due to the absence of background noise in the resulting assay. Preferred conjugates include those containing a hydrazone linkage.

In embodiments where X is a hydrazino or oxyamino group, the second component can be modified to possess an epoxide, α-bromocarbonyl, maleimide, maleic anhydride, isothiocyanate or isocyanate group. Such second components can be prepared by methods provided herein or by other methods well known to those of skill in the art. For example, reaction of pentafluorophenyl 4-isothiocyanatobenzoate with an amino or hydroxy group of a second component, such as a protein or oligosaccharide, results in formation of an isothiocyanato modified second component. Reaction of the hydrazino or oxyamino group of the modified oligonucleotide with the epoxide, α-bromocarbonyl, maleimide, maleic anhydride, isothiocyanate or isocyanate group of the second component results in covalent attachment of the oligonucleotide to the second component to form the conjugates provided herein.

In certain embodiments herein, the oligonucleotide conjugates are selected with the proviso that the covalent linkage is not an acyl hydrazone (—C(O)NHNH=). In preferred embodiments, the oligonucleotide conjugates are prepared from modified oligonucleotides of formula (II) where $P^2$ is not a phosphoramidate. In other embodiments, the oligonucleotide conjugates are selected with the proviso that the second component is not a protein, particularly a glycoprotein, more particularly an immunoglobulin.

The modified oligonucleotides provided herein also can be conjugated to ligands such as growth factors, membrane-active bacterial proteins and asialoglycoproteins as delivery strategies for antisense therapy and gene therapy (see, e.g., Perales et al. (1994) *Eur. J. Biochem.* 226:255; Cristiano et al. (1996) *Cancer Gene Ther.* 3:4; Hoganson et al. (1998) *Hum. Gene Ther.* 9:2565; Gottschalk et al. (1995) *Gene Ther.* 2:498; Lu et al. (1994) *J. Nucl. Med.* 35:269). Oligonucleotide-antigen conjugates can be used as immunomodulators in regulating airway eosinophilia in bronchial asthma (Shirota et al. (2000) *J. Immunol.* 164:5575). Oligonucleotide probes conjugated to fluorescent molecules are used in fluorescence in situ hybridization (FISH) for chromosome classification and the detection of chromosome aberrations (Pinkel et al. (1986) *Proc. Natl. Acad. Sci. USA* 83:2934). Oligonucleotide conjugates are also used to study the mechanics of DNA hybridization, and to investigate protein-DNA contacts of DNA binding proteins (Lannutti et al. (1996) *Biochemistry* 35:9821; Brown et al. (1997) *Curr. Opin. Biotechnol.* 8:45).

Importantly, in certain embodiments, the immobilized oligonucleotides or oligonucleotide conjugates provided herein can be formed under aqueous conditions without the need for additional reagents, such as a reducing agent.

Methods for the attachment of hydrazino modified, oxyamino modified or carbonyl modified oligonucleotides of formula (II), (IX) or (XI) to appropriately modified surfaces, as described herein, are provided. The attachment is via a covalent hydrazone or oxime bond formed from the hydrazino, oxyamino, or carbonyl group of the modified oligonucleotide and a complementary carbonyl, oxyamino or hydrazino modified surface provided herein (see, FIG. 2).

Methods for the conjugation of a first component oligonucleotide to second components, including, but not limited to, biopolymers as defined herein, macromolecules as defined herein, polymers including, but not limited to, polyamines, polyamides, polyethers and polyethylene glycols, and other compounds of interest herein for use in assays, kits, diagnostic arrays, and the like, including, but not limited to, intercalators, vitamins, reporter molecules, cholesterols, phospholipids, biotin, phenazine, phenanthridine, anthraquinone, acridine, fluoresceins, rhodamines, coumarins, dyes, antibodies, haptens, antigens, enzymes, and detection reagents including, but not limited to, fluorophores, metals including, but not limited to, gold, metal chelates, chromophores, fluorophore precursors and chromophore precursors, that possess or are modified to possess a hydrazino, oxyamino or carbonyl group that is complementary to the carbonyl, oxyamino or hydrazino group of the oligonucleotide of formula (II) for formation of hydrazone or oxime linkage, are provided. Fluorophore precursors and chromophore precursors are compounds that react with the hydrazino, oxyamino or carbonyl group of the modified oligonucleotide to form a fluorogenic or chromogenic group for analysis. In particular, methods for conjugation of a hydrazino, oxyamino, or carbonyl modified oligonucleotide of formula (II), (IX) or (XI) with an appropriately modified second component are provided. The conjugation is achieved through a covalent hydrazone or oxime bond formed from the hydrazino, oxyamino or carbonyl group of the modified oligonucleotide first component and a second component possessing a complementary carbonyl, oxyamino or hydrazino group.

In all embodiments herein, it is preferred that one, more preferably both, of the reactive partners (e.g., the hydrazino, oxyamino or carbonyl groups) are aromatic or heteroaromatic. Thus, in preferred embodiments, the compounds of formula (I), (VIII) or (X) will be aryl or heteroaryl hydrazino or oxyamino derivatives, or aryl or heteroaryl carbonyl derivatives. In more preferred embodiments, the coupling partner (e.g., the modified solid surface or the second component) will also possess an aryl or heteroaryl hydrazino or oxyamino group, or an aryl or heteroaryl carbonyl group. Hydrazone and oxime linkages formed from these preferred groups are more stable than the corresponding aliphatic hydrazone and oxime linkages, and thus are more preferred in certain applications.

DESCRIPTION OF THE FIGURES

FIG. 22 shows the synthesis of an ethidium bromide derivative provided herein.

DETAILED DESCRIPTION OF PREFERRED EMBODIMENTS

Definitions

Unless defined otherwise, all technical and scientific terms used herein have the same meaning as is commonly understood by one of skill in the art to which this invention belongs. All patents, patent applications and publications referred to throughout the disclosure herein are incorporated by reference in their entirety. In the event that there are a plurality of definitions for a term herein, those in this section prevail.

Figure 1:
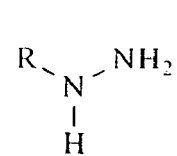
FIG. 1 illustrates hydrazino derivatives provided herein.
Figure 1:
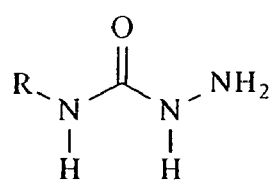
Figure 1:
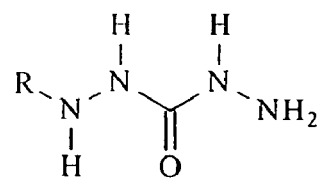
Figure 1:
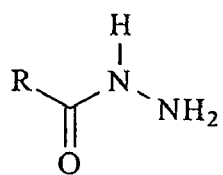
Figure 1:
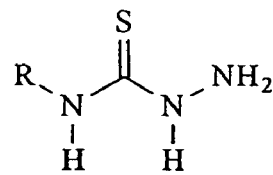
Figure 1:
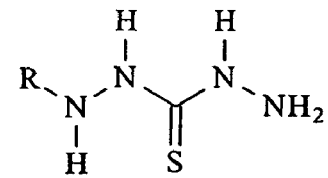
Figure 1:
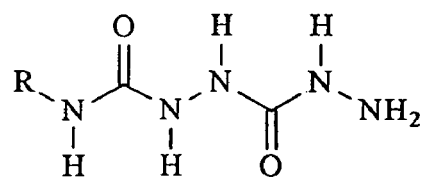
Figure 1:
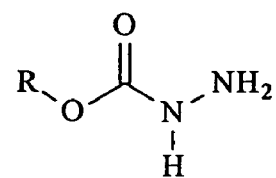
Figure 2:
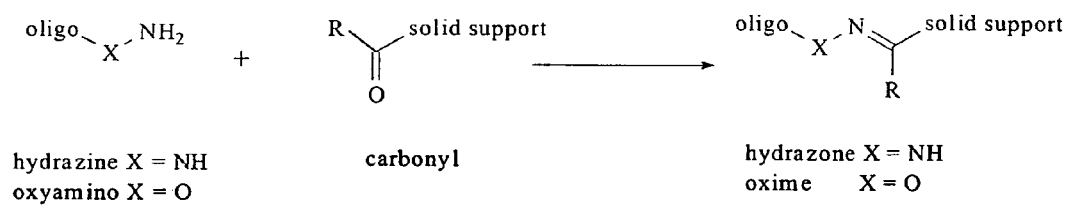
FIG. 2 illustrates the immobilization of a hydrazino or oxyamino modified oligonucleotide on a carbonyl modified solid support.

As used herein, "hydrazino groups" include, but are not limited to, hydrazines, hydrazides, semicarbazides, carbazides, thiosemicarbazides, thiocarbazides, hydrazine carboxylates and carbonic acid hydrazines (see, e.g., FIG. 1).

As used herein, hydrazone linkages include, but are not limited to, hydrazones, acyl hydrazones, semicarbazones, carbazones, thiosemicarbazones, thiocarbazones, hydrazone carboxylates and carbonic acid hydrazones.

As used herein, an oxyamino group has the formula —O—$NH_2$. An oxime has the formula —O—N=R.

As used herein, a protected hydrazino or a protected oxyamino group refers to a hydrazino or oxyamino group that has been derivatized as a salt of the hydrazino or oxyamino group, including but not limited to, mineral acids salts, such as but not limited to hydrochlorides and sulfates, and salts of organic acids, such as but not limited to acetates, lactates, malates, tartrates, citrates, ascorbates, succinates, butyrates, valerates and fumarates; or with any amino or hydrazino protecting group known to those of skill in the art (see, e.g., Greene et al. (1999) *Protective Groups in Organic Synthesis* (*3rd Ed.*) (J. Wiley Sons, Inc.)). Preferred amino and hydrazino protecting groups herein include, but are not limited to, amino or hydrazino protecting groups useful in the synthesis of oligonucleotides, more preferably monomethoxytrityl (MMT), dimethoxytrityl (DMT), 9-fluorenylmethoxycarbonyl (FMOC), acetyl, trifluoroacetyl, benzoyl, or a hydrazone or oxime that is cleaved under mild acidic conditions (e.g., 100 mM acetate, pH 4.5-5.5) including, but not limited to, a hydrazone or oxime formed from a lower aliphatic aldehyde or ketone, preferably from acetone, propanal, cyclohexanone or 2-butanone.

As used herein, an oligonucleotide is a nucleic acid, including, but not limited to, a ribonucleic acid (RNA), a deoxyribonucleic acid (DNA), and analogs thereof such as a protein nucleic acid (PNA), of any length, including chromosomes and genomic material, such as PCR products or sequencing reaction products, preferably DNA including double and single stranded forms. Single stranded forms of the oligonucleotides are also provided.

As used herein, a conjugate is a compound containing two components covalently linked together. For example, a first component, e.g., an oligonucleotide, is conjugated through a covalent hydrazone linkage to a second component, as defined herein, to form a conjugate.

As used herein, carbonyl derivatives include, but are not limited to, ketones and aldehydes.

As used herein, complementary reactive groups are those that, when reacted together, form a covalent linkage, including, but not limited to, a hydrazone or oxime linkage. Thus, a hydrazino group, as defined herein, is complementary to a carbonyl derivative. An oxyamino group is also complementary to a carbonyl derivative.

As used herein, "phosphorous based coupling group" refers to any phosphorous-containing group known to those of skill in the art to be useful in oligonucleotide synthesis including, but not limited to, phosphorodithioate, phosphorothioate, phosphoramidate, phosphonate, phosphiodiester, phosphotriester, thiophosphoramidate, thionoalkylphosphonate, thionoalkylphosphotriester or boranophosphate. As is appreciated by those of skill in the art, a number of chemistries, including, but not limited to, phosphoramidite, phosphonamide, H-phosphonate and phosphotriester chemistries, have been developed for the stepwise solid phase synthesis of oligonucleotides (DNA or RNA) and modified analogs (i.e., 2' modified RNA, methylphosphonates, 3'-5' phosphoramidites, and phosophorothioates). All phosphorous based coupling groups known to those of skill in the art are contemplated for use in the reagents and methods provided herein. See, e.g., Glen Research Catalog of Products for DNA Research, Glen Reserach, Sterling, Va. Exemplary phosphorous based coupling groups herein include β-cyanoethyl-N, N-diisopropylphosphoramidites.

As used herein, a biopolymer is any compound found in nature, or derivatives thereof, made up of monomeric units. Biopolymers include, but are not limited to, oligonucleotides, peptides, peptide nucleic acids (PNAs), glycoproteins and oligosaccharides. Thus, the monomeric units include, but are not limited to, nucleotides, nucleosides, amino acids, PNA monomers, monosaccharides, and derivatives thereof.

As used herein, a macromolecule refers to a molecule of colloidal size (i.e., of high molecular weight), including, but not limited to, proteins, polynucleic acids, polysaccharides and carbohydrates.

As used herein, a reporter molecule refers to a molecule, such as an enzyme or indicator, which is capable of generating a detectable signal (e.g., by colorimetric, chemiluminescent, bioluminescent, fluorescent, or potentiometric means) when contacted with a suitable substrate under appropriate reaction conditions. Exemplary reporter enzymes include, but are not limited to, alkaline phosphatase, horseradish peroxidase, β-galactosidase, aryl esterase, sulfatase and urease.

As used herein, a nucleobase is a heterocyclic moiety that is found in naturally occurring oligonucleotides, including ribonucleic acids (RNA) and deoxyribonucleic acids (DNA), and analogs thereof, including deaza analogs. Preferred nucleobases include, but are not limited to, cytosines, uracils, adenines, guanines and thymines, and analogs thereof including deaza analogs.

As used herein, a fluorophore refers to a fluorescent compound. Fluorescence is a physical process in which light is emitted from the compound following absorption of radiation. Generally, the emitted light is of lower energy and longer wavelength than that absorbed. Preferred fluorophores herein are those whose fluorescence can be detected using standard techniques.

As used herein, a derivative of a compound includes a salt, ester, enol ether, enol ester, solvate or hydrate thereof that can be prepared by those of skill in this art using known methods for such derivatization. Salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethylbenzimidazole, diethylamine and other alkylamines, piperazine and tris (hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids. Enol ethers include, but are not limited to, derivatives of formula C=C(OR) where R is hydrogen, alkyl, alkenyl, alkynyl, aryl, heteroaryl, aralkyl, heteroaralkyl, cycloalkyl ar heterocyclyl. Enol esters include, but are not limited to, derivatives of formula C=C(OC(O)R) where R is hydrogen, alkyl, alkenyl, alkynyl, aryl, heteroaryl, aralkyl, heteroaralkyl, cycloalkyl ar heterocyclyl. Solvates and hydrates are complexes of a compound with one or more solvent or water molecule, preferably 1 to about 100, more preferably 1 to about 10, most preferably one to about 2, 3 or 4, solvent or water molecules.

It is to be understood that the compounds provided herein can contain chiral centers. Such chiral centers can be of either the (R) or (S) configuration, or can be a mixture thereof. Thus, the compounds provided herein may be enantiomerically pure, or be stereoisomeric or diastereomeric mixtures. In the case of amino acid residues, such residues may be of either the L- or D-form. The preferred configuration for naturally occurring amino acid residues is L.

As used herein, alkyl, alkenyl and alkynyl carbon chains, if not specified, contain from 1 to 20 carbons, preferably 1 to 16 carbons, and are straight or branched. Alkenyl carbon chains of from 2 to 20 carbons preferably contain 1 to 8 double bonds, and the alkenyl carbon chains of 1 to 16 carbons preferably contain 1 to 5 double bonds. Alkynyl carbon chains of from 2 to 20 carbons preferably contain 1 to 8 triple bonds, and the alkynyl carbon chains of 2 to 16 carbons preferably contain 1 to 5 triple bonds. Exemplary alkyl, alkenyl and alkynyl groups herein include, but are not limited to, methyl, ethyl, propyl, isopropyl, isobutyl, n-butyl, sec-butyl, tert-butyl, isopentyl, neopentyl, tert-penytyl and isohexyl. The alkyl, alkenyl and alkynyl groups, unless otherwise specified, can be optionally substituted, with one or more groups, preferably alkyl group substituents that can be the same or different. As used herein, lower alkyl, lower alkenyl, and lower alkynyl refer to carbon chains having less than about 6 carbons. As used herein, "alk(en)(yn)yl" refers to an alkyl group containing at least one double bond and at least one triple bond.

As used herein, an "alkyl group substituent" includes halo, haloalkyl, preferably halo lower alkyl, aryl, hydroxy, alkoxy, aryloxy, alkyloxy, alkylthio, arylthio, aralkyloxy, aralkylthio, carboxy alkoxycarbonyl, oxo and cycloalkyl.

As used herein, "aryl" refers to cyclic groups containing from 5 to 19 carbon atoms. Aryl groups include, but are not limited to groups, such as fluorenyl, substituted fluorenyl, phenyl, substituted phenyl, naphthyl and substituted naphthyl, in which the substituent is lower alkyl, halogen, or lower alkoxy.

As used herein, an "aryl group substituent" includes alkyl, cycloalkyl, cycloalkylalkyl, aryl, heteroaryl optionally substituted with 1 or more, preferably 1 to 3, substituents selected from halo, halo alkyl and alkyl, aralkyl, heteroaralkyl, alkenyl containing 1 to 2 double bonds, alkynyl containing 1 to 2 triple bonds, alk(en)(yn)yl groups, halo, pseudohalo, cyano, hydroxy, haloalkyl and polyhaloalkyl, preferably halo lower alkyl, especially trifluoromethyl, formyl, alkylcarbonyl, arylcarbonyl that is optionally substituted with 1 or more, preferably 1 to 3, substituents selected from halo, halo alkyl and alkyl, heteroarylcarbonyl, carboxy, alkoxycarbonyl, aryloxycarbonyl, aminocarbonyl, alkylaminocarbonyl, dialkylaminocarbonyl, arylaminocarbonyl, diarylaminocarbonyl, aralkylaminocarbonyl, alkoxy, aryloxy, perfluoroalkoxy, alkenyloxy, alkynyloxy, arylalkoxy, aminoalkyl, alkylaminoalkyl, dialkylaminoalkyl, arylaminoalkyl, amino, alkylamino, dialkylamino, arylamino, alkylarylamino, alkylcarbonylamino, arylcarbonylamino, azido, nitro, mercapto, alkylthio, arylthio, perfluoroalkylthio, thiocyano, isothiocyano, alkylsulfinyl, alkylsulfonyl, arylsulfinyl, arylsulfonyl, aminosulfonyl, alkylaminosulfonyl, dialkylaminosulfonyl and arylaminosulfonyl.

As used herein, "aralkyl" refers to an alkyl group in which one of the hydrogen atoms of the alkyl is replaced by an aryl group.

As used herein, "heteroaralkyl" refers to an alkyl group in which one of the hydrogen atoms of the alkyl is replaced by a heteroaryl group.

As used herein, "cycloalkyl" refers to a saturated mono- or multicyclic ring system, preferably of 3 to 10 carbon atoms, more preferably 3 to 6 carbon atoms; cycloalkenyl and cycloalkynyl refer to mono- or multicyclic ring systems that respectively include at least one double bond and at least one triple bond. Cycloalkenyl and cycloalkynyl groups can preferably contain 3 to 10 carbon atoms, with cycloalkenyl groups more preferably containing 4 to 7 carbon atoms and cycloalkynyl groups more preferably containing 8 to 10 carbon atoms. The ring systems of the cycloalkyl, cycloalkenyl and cycloalkynyl groups can be composed of one ring or two or more rings which can be joined together in a fused, bridged or spiro-connected fashion, and can be optionally substituted with one or more alkyl group substituents. "Cycloalk(en)(yn)yl" refers to a cylcoalkyl group containing at least one double bond and at least one triple bond.

As used herein, "heteroaryl" refers to a monocyclic or multicyclic ring system, preferably of about 5 to about 15 members where one or more, more preferably 1 to 3 of the atoms in the ring system is a heteroatom, that is, an element other than carbon, for example, nitrogen, oxygen and sulfur atoms. The heteroaryl can be optionally substituted with one or more, preferably 1 to 3, aryl group substituents. The heteroaryl group can be optionally fused to a benzene ring. Exemplary heteroaryl groups include, for example, furyl, imidazinyl, pyrrolidinyl, pyrimidinyl, tetrazolyl, thienyl, pyridyl, pyrrolyl, N-methylpyrrolyl, quinolinyl and isoquinolinyl, with pyridyl and quinolinyl being preferred.

As used herein, "heterocyclic" refers to a monocyclic or multicyclic ring system, preferably of 3 to 10 members, more preferably 4 to 7 members, even more preferably 5 to 6 members, where one or more, preferably 1 to 3 of the atoms in the ring system is a heteroatom, that is, an element other than carbon, for example, nitrogen, oxygen and sulfur atoms. The heterocycle can be optionally substituted with one or more, preferably 1 to 3 aryl group substituents. Preferred substituents of the heterocyclic group include hydroxy, amino, alkoxy containing 1 to 4 carbon atoms, halo lower alkyl, including trihalomethyl, such as trifluoromethyl, and halogen. As used herein, the term heterocycle includes reference to heteroaryl.

As used herein, the nomenclature alkyl, alkoxy, carbonyl, etc. are used as is generally understood by those of skill in this art. For example, as used herein alkyl refers to saturated carbon chains that contain one or more carbons; the chains are straight or branched or include cyclic portions or be cyclic.

As used herein, alicyclic refers to aryl groups that are cyclic.

For purposes herein, where the number of any given substituent is not specified (e.g., "haloalkyl"), there can be one or more substituents present. For example, "haloalkyl" includes one or more of the same or different halogens. As another example, "$C_{1-3}$alkoxyphenyl" can include one or more of the same or different alkoxy groups containing one, two or three carbons.

As used herein, "halogen" or "halide" refers to F, Cl, Br or I.

As used herein, pseudohalides are compounds that behave substantially similar to halides. Such compounds can be used in the same manner and treated in the same manner as halides ($X^-$, in which X is a halogen, such as Cl or Br). Pseudohalides include, but are not limited to, cyanide, cyanate, thiocyanate, selenocyanate, trifluoromethoxy, trifluoromethyl and azide.

As used herein, "haloalkyl" refers to a lower alkyl radical in which one or more of the hydrogen atoms are replaced by halogen including, but not limited to, chloromethyl, trifluoromethyl, 1-chloro-2-fluoroethyl and the like.

As used herein, "haloalkoxy" refers to RO— in which R is a haloalkyl group.

As used herein, "sulfinyl" or "thionyl" refers to —S(O)—.
As used herein, "sulfonyl" or "sulfuryl" refers to —S(O)$_2$—.
As used herein, "sulfo" refers to —S(O)$_3$—.

As used herein, "carboxy" refers to a divalent radical, —C(O)O—.

As used herein, "aminocarbonyl" refers to —C(O)NH$_2$.

As used herein, "alkylaminocarbonyl" refers to —C(O)NHR in which R is hydrogen or alkyl, preferably lower alkyl. As used herein "dialkylaminocarbonyl" as used herein refers to —C(O)NR'R in which R' and R are independently selected from hydrogen or alkyl, preferably lower alkyl; "carboxamide" refers to groups of formula —NR'COR.

As used herein, "diarylaminocarbonyl" refers to —C(O)NRR' in which R and R' are independently selected from aryl, preferably lower aryl, more preferably phenyl.

As used herein, "aralkylaminocarbonyl" refers to —C(O)NRR' in which one of R and R' is aryl, preferably lower aryl, more preferably phenyl, and the other of R and R' is alkyl, preferably lower alkyl.

As used herein, "arylaminocarbonyl" refers to —C(O)NHR in which R is aryl, preferably lower aryl, more preferably phenyl.

As used herein, "alkoxycarbonyl" refers to —C(O)OR in which R is alkyl, preferably lower alkyl.

As used herein, "aryloxycarbonyl" refers to —C(O)OR in which R is aryl, preferably lower aryl, more preferably phenyl.

As used herein, "alkoxy" and "alkylthio" refer to RO— and RS—, in which R is alkyl, preferably lower alkyl.

As used herein, "aryloxy" and "arylthio" refer to RO— and RS—, in which R is aryl, preferably lower aryl, more preferably phenyl.

As used herein, "alkylene" refers to a straight, branched or cyclic, preferably straight or branched, bivalent aliphatic hydrocarbon group, preferably having from 1 to about 20 carbon atoms, more preferably 1 to 12 carbons, even more preferably lower alkylene. The alkylene group is optionally substituted with one or more "alkyl group substituents." There can be optionally inserted along the alkylene group one or more oxygen, sulphur or substituted or unsubstituted nitrogen atoms, where the nitrogen substituent is alkyl as previously described. Exemplary alkylene groups include methylene (—CH$_2$—), ethylene (—CH$_2$CH$_2$—), propylene (—(CH$_2$)$_3$—), cyclohexylene (—C$_6$H$_{10}$—), methylenedioxy (—O—CH$_2$—O—) and ethylenedioxy (—O—(CH$_2$)$_2$—O—). The term "lower alkylene" refers to alkylene groups having 1 to 6 carbons. Preferred alkylene groups are lower alkylene, with alkylene of 1 to 3 carbon atoms being particularly preferred.

As used herein, "alkenylene" refers to a straight, branched or cyclic, preferably straight or branched, bivalent aliphatic hydrocarbon group, preferably having from 2 to about 20 carbon atoms and at least one double bond, more preferably 1 to 12 carbons, even more preferably lower alkenylene. The alkenylene group is optionally substituted with one or more "alkyl group substituents." There can be optionally inserted along the alkenylene group one or more oxygen, sulphur or substituted or unsubstituted nitrogen atoms, where the nitrogen substituent is alkyl as previously described. Exemplary alkenylene groups include —CH═CH—CH═CH— and —CH═CH—CH$_2$—. The term "lower alkenylene" refers to alkenylene groups having 2 to 6 carbons. Preferred alkenylene groups are lower alkenylene, with alkenylene of 3 to 4 carbon atoms being particularly preferred.

As used herein, "alkynylene" refers to a straight, branched or cyclic, preferably straight or branched, bivalent aliphatic hydrocarbon group, preferably having from 2 to about 20 carbon atoms and at least one triple bond, more preferably 1 to 12 carbons, even more preferably lower alkynylene. The alkynylene group is optionally substituted with one or more "alkyl group substituents." There can be optionally inserted along the alkynylene group one or more oxygen, sulphur or substituted or unsubstituted nitrogen atoms, where the nitrogen substituent is alkyl as previously described. Exemplary alkynylene groups include —C≡C—C≡C—, —C≡C— and —C≡C—CH$_2$—. The term "lower alkynylene" refers to alkynylene groups having 2 to 6 carbons. Preferred alkynylene groups are lower alkynylene, with alkynylene of 3 to 4 carbon atoms being particularly preferred.

As used herein, "alk(en)(yn)ylene" refers to a straight, branched or cyclic, preferably straight or branched, bivalent aliphatic hydrocarbon group, preferably having from 2 to about 20 carbon atoms and at least one triple bond, and at least one double bond; more preferably 1 to 12 carbons, even more preferably lower alk(en)(yn)ylene. The alk(en)(yn)ylene group is optionally substituted with one or more "alkyl group substituents." There can be optionally inserted along the alkynylene group one or more oxygen, sulphur or substituted or unsubstituted nitrogen atoms, where the nitrogen substituent is alkyl as previously described. Exemplary alk(en)(yn)ylene groups include —C≡C—(CH$_2$)$_n$—C≡C—, where n is 1 or 2. The term. "lower alk(en)(yn)ylene" refers to alk(en)(yn)ylene groups having up to 6 carbons. Preferred alk(en)(yn)ylene groups are lower alk(en)(yn)ylene, with alk(en)(yn)ylene of 4 carbon atoms being particularly preferred.

As used herein, "arylene" refers to a monocyclic or polycyclic, preferably monocyclic, bivalent aromatic group, preferably having from 5 to about 20 carbon atoms and at least one aromatic ring, more preferably 5 to 12 carbons, even more preferably lower arylene. The arylene group is optionally substituted with one or more "alkyl group substituents." There can be optionally inserted around the arylene group one or more oxygen, sulphur or substituted or unsubstituted nitrogen atoms, where the nitrogen substituent is alkyl as previously described. Exemplary arylene groups include 1,2-, 1,3- and 1,4-phenylene. The term "lower arylene" refers to arylene groups having 5 or 6 carbons. Preferred arylene groups are lower arylene.

As used herein, "heteroarylene" refers to a bivalent monocyclic or multicyclic ring system, preferably of about 5 to about 15 members where one or more, more preferably 1 to 3 of the atoms in the ring system is a heteroatom, that is, an element other than carbon, for example, nitrogen, oxygen and sulfur atoms. The heteroarylene group are optionally substituted with one or more, preferably 1 to 3, aryl group substituents.

As used herein, "alkylidene" refers to a bivalent group, such as ═CR'R", which is attached to one atom of another group, forming a double bond. Exemplary alkylidene groups are methylidene (═CH$_2$) and ethylidene (═CHCH$_3$). As used herein, "aralkylidene" refers to an alkylidene group in which either R' or R" is and aryl group.

As used herein, "amido" refers to the bivalent group —C(O)NH—. "Thioamido" refers to the bivalent group —C(S)NH—. "Oxyamido" refers to the bivalent group —OC(O)NH—. "Thiaamido" refers to the bivalent group —SC(O)NH—. "Dithiaamido" refers to the bivalent group —SC(S)NH—. "Ureido" refers to the bivalent group —HNC(O)NH—. "Thioureido" refers to the bivalent group —HNC(S)NH—.

As used herein, "semicarbazide" refers to —NHC(O)NHNH—. "Carbazate" refers to the bivalent group —OC(O)NHNH—. "Isothiocarbazate" refers to the bivalent group —SC(O)NHNH—. "Thiocarbazate" refers to the bivalent group —OC(S)NHNH—. "Sulfonylhydrazide" refers to the group —SO$_2$NHNH—. "Hydrazide" refers to the bivalent group —C(O)NHNH—. "Azo" refers to the bivalent group —N═N—. "Hydrazinyl" refers to the bivalent group —NH—NH—.

As used herein, the term "amino acid" refers to α-amino acids which are racemic, or of either the D- or L-configuration. The designation "d" preceding an amino acid designation (e.g., dAla, dSer, dVal, etc.) refers to the D-isomer of the amino acid. The designation "dl" preceding an amino acid designation (e.g., dlPip) refers to a mixture of the L- and D-isomers of the amino acid.

As used herein, when any particular group, such as phenyl or pyridyl, is specified, this means that the group is unsubstituted or is substituted. Preferred substituents where not specified are halo, halo lower alkyl, and lower alkyl.

As used herein, a composition refers to any mixture of two or more products or compounds. It can be a solution, a suspension, liquid, powder, a paste, aqueous, non-aqueous or any combination thereof.

As used herein, a combination refers to any association between two or more items.

As used herein, fluid refers to any composition that can flow. Fluids thus encompass compositions that are in the form of semi-solids, pastes, solutions, aqueous mixtures, gels, lotions, creams and other such compositions.

As used herein, substantially identical to a product means sufficiently similar so that the property of interest is sufficiently unchanged so that the substantially identical product can be used in place of the product.

As used herein, the abbreviations for any protective groups, amino acids and other compounds, are, unless indicated otherwise, in accord with their common usage, recognized abbreviations, or the IUPAC-IUB Commission on Biochemical Nomenclature (see, *Biochem*. 1972, 11, 942).

A. Functional Biopolymer Immobilization and Conjugation Reagents

Reagents for immobilization and conjugation of oligonucleotides are provided. The reagents are bifunctional phosphorous containing monomers that are incorporated into an oligonucleotide during standard solid phase synthesis. The reagents possess a phosphorous based coupling group that can be coupled at the 5' or 3' terminus, preferably the 5' terminus, of an oligonucleotide. Alternatively, the reagents can be incorporated at an internal position in the oligonucleotide, thus forming an oligonucleotide analog.

Phosphorous based coupling groups for use in the reagents and methods herein include, but are not limited to, phosphoramidites, H-phosphonates and phosphotriesters. Preferred phosphorous based coupling groups are phosphoramidites. In particular, β-cyanoethyl-N,N-diisopropylphosphoramidite groups can be used in the reagents and methods provided herein. Thus, in particularly preferred embodiments herein $P^1$ is (NCCH$_2$CH$_2$O)(i-Pr$_2$N)P—O—.

The reagents also possess, in addition to the phosphorous based coupling group, a protected hydrazino, protected oxyamino, or a carbonyl moiety for formation of a hydrazone or oxime linkage with an appropriately modified surface or biopolymer. The hydrazino moiety can be an aliphatic, aromatic or heteroaromatic hydrazine, semicarbazide, carbazide, hydrazide, thiosemicarbazide, thiocarazide, carbonic acid dihydrazine or hydrazine carboxylate (see, FIG. 1). The protecting groups are salts of the hydrazino or oxyamino group, or any amino or hydrazino protecting groups known to those of skill in the art. (see, e.g., Greene et al. (1999) *Protective Groups in Organic Synthesis* (3rd Ed.) (J. Wiley Sons, Inc.)). The carbonyl moiety can be any carbonyl containing group capable of forming a hydrazone linkage with one or more of the above hydrazino moieties. Preferred carbonyl moieties include aldehydes and ketones.

For incorporation at an internal position in the oligonucleotide, the reagents provided herein also possess a hydroxyl group. The hydroxyl group provides a site for continuing the oligonucleotide synthesis. The hydroxyl group of the reagent can be a free OH group or can be appropriately protected for use in solid phase oligonucleotide synthesis. For example, the hydroxyl group can be protected as the corresponding monomethoxytrityl (MMT) ether. In these embodiments, the hydrazino or oxyamino group, if present, is protected with a group that is orthogonal to an MMT ether (i.e., that is not removed under conditions where an MMT ether is cleaved, but is removed under conditions where an MMT ether is stable). Groups that are orthogonal to an MMT ether include, but are not limited to, carbonates, including 9-fluorenylmethoxycarbonyl (FMOC) carbonates.

Alternatively, a phosphoramidite monomer containing two orthogonally-protected alcohols can be used in the oligonucleotide synthesis. One of the protecting groups is amenable to standard oligonucleotide synthesis. Following oligonucleotide synthesis incorporating the monomer at an internal position of the oligonucleotide, the orthogonal protecting group is removed to afford a free alcohol. Reaction of this alcohol with a reagent of formula (I) provides the desired hydrazino, oxyamino, or carbonyl modified oligonucleotide. In one embodiment, the protecting group amenable to oligonucleotide synthesis is am MMT ether, and the other is a protecting group that is orthogonal to an MMT ether including, but not limited to, a carbonate such as an FMOC carbonate. Phosphoramidites containing two orthogonally-protected alcohols are commercially available (see, e.g., "Asymmetric Doubler Phosphoramidite", Glen Research Corporation, Sterling, Va.).

In another alternative, a hydroxyl-substituted nucleoside, preferably possessing the hydroxy group linked to the nucleobase either directly or through a carbon chain, is incorporated into the oligonucleotide during standard synthesis. The hydroxyl group is preferably protected with a group that is orthogonal to protecting groups amenable to oligonucleotide synthesis. Such groups include, but are not limited to, carbonates such as an FMOC carbonate. Following oligonucleotide synthesis, the protecting group is removed and the resulting free alcohol is reacted with a reagent of formula (I) to provide a hydrazino, oxyamino, or carbonyl modified oligonucleotide. In one embodiment, the hydroxy substituted nucleoside is a 5'-(O-MMT)-5-substituted cytosine possessing an FMOC protected hydroxyl group on the 5-substituent.

In one embodiment, the reagents for use in the methods provided herein have formula (I):

$P^1$-M-X or a derivative thereof, as defined herein, where $P^1$ is a phosphorous based coupling group, as defined herein, preferably a phosphoramidite, more preferably $(NCCH_2CH_2O)(i\text{-}Pr_2N)P\text{—}O\text{—}$; X is a protected hydrazino group; and M is a divalent group having any combination, preferably 1-2000, more preferably 1-1000, particularly 1-100, most preferably 1-50 or 1-25 or 1-10, of the following groups, which can be combined in any order: arylene, heteroarylene, cycloalkylene, $C(R^1)_2$, $—C(R^1)=C(R^1)—$, $>C=C(R^2)(R^3)$, $>C(R^2)(R^3)$, $—C\equiv C—$, O, $S(A)_a$, $P(D)_b(R^1)$, $P(D)_b(ER^1)$, $N(R^1)$, $>N^+(R^2)(R^3)$ and C(E); where a is 0, 1 or 2; b is 0, 1, 2 or 3; A is O or $NR^1$; D is S or O; and E is S, O or $NR^1$; each $R^1$ is a monovalent group independently selected from hydrogen and $M^1\text{-}R^4$; each $M^1$ is a divalent group independently having any combination of the following groups, which groups can be combined in any order: a direct link, arylene, heteroarylene, cycloalkylene, $C(R^5)_2$, $—C(R^5)=C(R^5)—$, $>C=C(R^2)(R^3)$, $>C(R^2)(R^3)$, $—C\equiv C—$, O, $S(A)_a$, $P(D)_b(R^5)$, $P(D)_b(ER^5)$, $N(R^5)$, $N(COR^5)$, $>N^+(R^2)(R^3)$ and C(E); where a is 0, 1 or 2; b is 0, 1, 2 or 3; A is O or $NR^5$; D is S or O; and E is S, O or $NR^5$; $R^4$ and $R^5$ are each independently selected from the group among hydrogen, halo, pseudohalo, cyano, azido, nitro, $SiR^6R^7R^8$, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy and $NR^9R^{10}$; $R^9$ and $R^{10}$ are each independently selected from hydrogen, alkyl, alkenyl, alkynyl, cycloalkyl, aryl, aralkyl, heteroaryl, heteroaralkyl and heterocyclyl; $R^2$ and $R^3$ are selected from (i) or (ii) as follows: (i) $R^2$ and $R^3$ are independently selected among hydrogen, alkyl, alkenyl, alkynyl, cycloalkyl, aryl and heteroaryl; or (ii) $R^2$ and $R^3$ together form alkylene, alkenylene or cycloalkylene; $R^6$, $R^7$ and $R^8$ are each independently a monovalent group selected from hydrogen, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy and $NR^9R^{10}$; and $R^1$, $R^2$, $R^3$, $R^4$, $R^5$, $R^6$, $R^7$, $R^8$, $R^9$ and $R^{10}$ can be substituted with one or more substituents each independently selected from Z, wherein Z is selected from alkyl, alkenyl, alkynyl, aryl, cycloalkyl, cycloalkenyl, hydroxy, $S(O)_hR^{20}$, $NR^{20}R^{21}$, $COOR^{20}$, $COR^{20}$, $CONR^{20}R^{21}$, $OC(O)NR^{20}R^{21}$, $N(R^{20})C(O)R^{21}$, alkoxy, aryloxy, heteroaryl, heterocyclyl, heteroaryloxy, heterocyclyloxy, aralkyl, aralkenyl, aralkynyl, heteroaralkyl, heteroaralkenyl, heteroaralkynyl, aralkoxy, heteroaralkoxy, alkoxycarbonyl, carbamoyl, thiocarbamoyl, alkoxycarbonyl, carboxyaryl, halo, pseudohalo, haloalkyl and carboxamido; h is 0, 1 or 2; and $R^{20}$ and $R^{21}$ are each independently selected from among hydrogen, halo, pseudohalo, cyano, azido, nitro, trialkylsilyl, dialkylarylsilyl, alkyldiarylsilyl, triarylsilyl, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy, amino, amido, alkylamino, dialkylamino, alkylarylamino, diarylamino and arylamino.

In certain embodiments herein, when X is a protected hydrazine group, the X group does not substitute the nucleobase of a nucleoside, nucleotide, or analog thereof.

In another embodiment, the reagents for use in the methods provided herein have formula (I):

$P^1$-M-X or a derivative thereof, as defined herein, where $P^1$ is a phosphorous based coupling group, as defined herein, preferably a phosphoramidite, more preferably $(NCCH_2CH_2O)(i-Pr_2N)P-O-$; X is a protected oxyamino group; and M is a divalent group having any combination, preferably 1-2000, more preferably 1-1000, particularly 1-100, most preferably 1-50 or 1-25 or 1-10, of the following groups, which can be combined in any order: arylene, heteroarylene, cycloalkylene, $C(R^1)_2$, $-C(R^1)=C(R^1)-$, $>C=C(R^2)(R^3)$, $>C(R^2)(R^3)$, $-C\equiv C-$, O, $S(A)_a$, $P(D)_b(R^1)$, $P(D)_b(ER^1)$, $N(R^1)$, $>N^+(R^2)(R^3)$ and C(E); where a is 0, 1 or 2; b is 0, 1, 2 or 3; A is O or $NR^1$; D is S or O; and E is S, O or $NR^1$; each $R^1$ is a monovalent group independently selected from hydrogen and $M^1$-$R^4$; each $M^1$ is a divalent group independently having any combination of the following groups, which groups can be combined in any order: a direct link, arylene, heteroarylene, cycloalkylene, $C(R^5)_2$, $-C(R^5)=C(R^5)-$, $>C=C(R^2)(R^3)$, $>C(R^2)(R^3)$, $-C\equiv C-$, O, $S(A)_a$, $P(D)_b(R^5)$, $P(D)_b(ER^5)$, $N(R^5)$, $N(COR^5)$, $>N^+(R^2)(R^3)$ and C(E); where a is 0, 1 or 2; b is 0, 1, 2 or 3; A is O or $NR^5$; D is S or O; and E is S, O or $NR^5$; $R^4$ and $R^5$ are each independently selected among hydrogen, halo, pseudohalo, cyano, azido, nitro, $SiR^6R^7R^8$, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy and $NR^9R^{10}$; $R^9$ and $R^{10}$ are each independently selected from hydrogen, alkyl, alkenyl, alkynyl, cycloalkyl, aryl, aralkyl, heteroaryl, heteroaralkyl and heterocyclyl; $R^2$ and $R^3$ are selected from (i) or (ii) as follows: (i) $R^2$ and $R^3$ are independently selected from among hydrogen, alkyl, alkenyl, alkynyl, cycloalkyl, aryl and heteroaryl; or (ii) $R^2$ and $R^3$ together form alkylene, alkenylene or cycloalkylene; $R^6$, $R^7$ and $R^8$ are each independently a monovalent group selected from hydrogen, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy and $NR^9R^{10}$; and $R^1$, $R^2$, $R^3$, $R^4$, $R^5$, $R^6$, $R^7$, $R^8$, $R^9$ and $R^{10}$ can be substituted with one or more substituents each independently selected from Z, wherein Z is selected from alkyl, alkenyl, alkynyl, aryl, cycloalkyl, cycloalkenyl, hydroxy, $S(O)_hR^{20}$, $NR^{20}R^{21}$, $COOR^{20}$, $COR^{20}$, $CONR^{20}R^{21}$, $OC(O)NR^{20}R^{21}$, $N(R^{20})C(O)R^{21}$, alkoxy, aryloxy, heteroaryl, heterocyclyl, heteroaryloxy, heterocyclyloxy, aralkyl, aralkenyl, aralkynyl, heteroaralkyl, heteroaralkenyl, heteroaralkynyl, aralkoxy, heteroaralkoxy, alkoxycarbonyl, carbamoyl, thiocarbamoyl, alkoxycarbonyl, carboxyaryl, halo, pseudohalo, haloalkyl and carboxamido; h is 0, 1 or 2; and $R^{20}$ and $R^{21}$ are each independently selected from among hydrogen, halo, pseudohalo, cyano, azido, nitro, trialkylsilyl, dialkylarylsilyl, alkyldiarylsilyl, triarylsilyl, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy, amino, amido, alkylamino, dialkylamino, alkylarylamino, diarylamino and arylamino.

In certain embodiments herein, when X is a protected oxyamino group, the X group does not substitute the 2', 3' or 5', particularly the 2', position of a nucleoside, nucleotide, or analog thereof. In other embodiments, when X is a protected oxyamino group, M is selected with the proviso that it is not tetra(ethyleneoxy) (i.e., $(CH_2CH_2O)_4$, TEG). In certain embodiments, when X is a protected oxyamino group, the X group does not substitute the nucleobase of a nucleoside, nucleotide, or analog thereof.

In another embodiment, the reagents for use in the methods provided herein have formula (I):

$P^1$-M-X or a derivative thereof, as defined herein, where $P^1$ is a phosphorous based coupling group, as defined herein, preferably a phosphoramidite, more preferably $(NCCH_2CH_2O)(i-Pr_2N)P-O-$; X is a carbonyl group; and M is a divalent group having any combination, preferably 1-2000, more preferably 1-1000, particularly 1-100, most preferably 1-50 or 1-25 or 1-10, of the following groups, which can be combined in any order: arylene, heteroarylene, cycloalkylene, $C(R^1)_2$, $-C(R^1)=C(R^1)-$, $>C=C(R^2)(R^3)$, $>C(R^2)(R^3)$, $-C\equiv C-$, O, $S(A)_a$, $P(D)_b(R^1)$, $P(D)_b(ER^1)$, $N(R^1)$, $>N^+(R^2)(R^3)$ and C(E); where a is 0, 1 or 2; b is 0, 1, 2 or 3; A is O or $NR^1$; D is S or O; and E is S, O or $NR^1$; each $R^1$ is a monovalent group independently selected from hydrogen and $M^1$-$R^4$; each $M^1$ is a divalent group independently having any combination of the following groups, which groups can be combined in any order: a direct link, arylene, heteroarylene, cycloalkylene, $C(R^5)_2$, $-C(R^5)=C(R^5)-$, $>C=C(R^2)(R^3)$, $>C(R^2)(R^3)$, $-C\equiv C-$, O, $S(A)_a$, $P(D)_b(R^5)$, $P(D)_b(ER^5)$, $N(R^5)$, $N(COR^5)$, $>N^+(R^2)(R^3)$ and C(E); where a is 0, 1 or 2; b is 0, 1, 2 or 3; A is O or $NR^5$; D is S or O; and E is S, O or $NR^5$; $R^4$ and $R^5$ are each independently selected from among hydrogen, halo, pseudohalo, cyano, azido; nitro, $SiR^6R^7R^8$, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy and $NR^9R^{10}$; $R^9$ and $R^{10}$ are each independently selected from hydrogen, alkyl, alkenyl, alkynyl, cycloalkyl, aryl, aralkyl, heteroaryl, heteroaralkyl and heterocyclyl; $R^2$ and $R^3$ are selected from (i) or (ii) as follows: (i) $R^2$ and $R^3$ are independently selected from among hydrogen, alkyl, alkenyl, alkynyl, cycloalkyl, aryl and heteroaryl; or (ii) $R^2$ and $R^3$ together form alkylene, alkenylene or cycloalkylene; $R^6$, $R^7$ and $R^8$ are each independently a monovalent group selected from hydrogen, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy and $NR^9R^{10}$; and $R^1$, $R^2$, $R^3$, $R^4$, $R^5$, $R^6$, $R^7$, $R^8$, $R^9$ and $R^{10}$ can be substituted with one or more substituents each independently selected from Z, wherein Z is selected from alkyl, alkenyl, alkynyl, aryl, cycloalkyl, cycloalkenyl, hydroxy, $S(O)R^{20}$, $NR^{20}R^{21}$, $COOR^{20}$, $COR^{20}$, $CONR^{20}R^{21}$, $OC(O)NR^{20}R^{21}$, $N(R^{20})C(O)R^{21}$, alkoxy, aryloxy, heteroaryl, heterocyclyl, heteroaryloxy, heterocyclyloxy, aralkyl, aralkenyl, aralkynyl, heteroaralkyl, heteroaralkenyl, heteroaralkynyl, aralkoxy, heteroaralkoxy, alkoxycarbonyl, carbamoyl, thiocarbamoyl, alkoxycarbonyl, carboxyaryl, halo, pseudohalo, haloalkyl and carboxamido; h is 0, 1 or 2; and $R^{20}$ and $R^{21}$ are each independently selected from among hydrogen, halo, pseudohalo, cyano, azido, nitro, trialkylsilyl, dialkylarylsilyl, alkyldiarylsilyl, triarylsilyl, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy, amino, amido, alkylamino, dialkylamino, alkylarylamino, diarylamino and arylamino.

In certain embodiments, when X is a carbonyl group, particularly an aldehyde group, the X group does not substitute the nucleobase of a nucleoside, nucleotide, or analog thereof.

In certain embodiments, the reagents for use in the methods provided herein are phosphoramites that have formula (I):

$$P^1\text{-M-X}$$

or a derivative thereof, wherein $P^1$ is $(NCCH_2CH_2O)(i\text{-}Pr_2N)P\text{—}O\text{—}$; X is a protected hydrazino, protected oxyamino, or a carbonyl group; and M is as defined above.

M preferably has 1-2000, more preferably 1-1000, particularly 1-100, most preferably 1-50 or 1-25 or 1-10 of the groups as defined above. In certain embodiments, M has 1-50, preferably 1-25, more preferably 1-10 of the following groups, which can be combined in any order: arylene, heteroarylene, $C(R^5)_2$, O, $S(A)_a$, $N(R^5)$, $N(COR^5)$ and $C(E)$; where a is 0, 1 or 2; A is O or $NR^5$; and E is S, O or $NR^5$; where $R^5$ is as defined above. In more preferred embodiments, M has 1-10 of the following groups, which can be combined in any order: heteroarylene, $C(R^5)_2$, $N(R^5)$ and $C(E)$; where E is S, O or $NR^5$; where $R^5$ is as defined above. In other embodiments, M has 1-10 of the following groups, which can be combined in any order: arylene, $C(R^5)_2$, $N(R^5)$ and $C(E)$; where E is S, O or $NR^5$; where $R^5$ is as defined above. $R^5$ is preferably hydrogen; and E is preferably oxygen. In these embodiments, the heteroarylene groups of M are preferably monocyclic or fused bicyclic divalent groups, more preferably monocyclic divalent groups, including, but not limited to, thienylene, furylene, pyrrolylene including 2,3-, 2,4- and 2,5-pyrrolylene, pyridylene including 2,3-, 2,4-, 2,5- and 2,6-pyridylene, triazinylene including 1,3,5-triazinylene, triazolylene including 1,2,4- and 1,2,3-triazolylene or pyrimidylene including 2,4-, 2,5- and 2,6-pyrimidylene groups. The arylene groups of M are preferably divalent monocyclic, bicyclic or tricyclic groups, including, but not limited to, 1,2-, 1,3- and 1,4-phenylene, and naphthylene.

In other embodiments, M is a chain of repeating monomer units, preferably 1-2000 monomer units, more preferably 1-1000, particularly 1-100, most preferably 1-50 or 1-25 or 1-10, including, but not limited to, ethylene oxide, propylene oxide, methacrylamide, or ethylene glycol. Thus, in certain embodiments, M is a polyethylene glycol (PEG), polypropylene glycol (PPG) or acrylate chain. In particular embodiments, M is a diethyleneglycol, triethyleneglycol or tetraethyleneglycol moiety.

In other embodiments, M contains a cleavable linkage, including, but not limited to, a disulfide, an ester, an enzyme specific peptide, a photocleavable linkage, such as nitroaromatic group, or an acid labile group. Reagents of formula (I) and modified oligonucleotides of formula (II) containing such M groups have applications in capture assay methods where the analyte is captured by the modified oligonucleotide, the conjugate isolated, and the M group cleaved to provide an isolated analyte. See, e.g., Niemeyer et al. (1994) *Nucl. Acids Res.* 22(25):5530-5539.

X is preferably —$C(O)R^{30}$, —Y—$N(R^{31})$—$Y^1$—$N(R^{32})$—$Y^2$ or —O—$N(R^{30})$—$Y^2$; where $R^{30}$, $R^{31}$ and $R^{32}$ are each independently hydrogen, alkyl, alkenyl, alkynyl, aryl, heteroaryl, aralkyl, aralkenyl, aralkynyl, heteroaralkyl, heteroaralkenyl, heteroaralkynyl, heterocyclyl or cycloalkyl; Y and $Y^1$ are selected as in (i) or (ii) as follows:

(i) Y is a direct link, and $Y^1$ is a direct link, $C(O)N(R^{35})$, $N(R^{35})C(O)N(R^{36})$, $C(S)N(R^{35})$, $N(R^{35})C(S)N(R^{36})$ or $C(O)N(R^{35})N(R^{36})C(O)N(R^{37})$; or (ii) Y is C(O) or OC(O), and $Y^1$ is a direct link;

where $R^{35}$, $R^{36}$ and $R^{37}$ are each independently selected from among hydrogen, alkyl, alkenyl, alkynyl, aryl, heteroaryl, aralkyl, aralkenyl, aralkynyl, heteroaralkyl, heteroaralkenyl, heteroaralkynyl, heterocyclyl and cylcoalkyl; and $Y^2$ is a salt of the hydrazino or oxyamino group, including but not limited to, mineral acids salts, such as but not limited to hydrochlorides and sulfates, and salts of organic acids, such as but not limited to acetates, lactates, malates, tartrates, citrates, ascorbates, succinates, butyrates, valerates and fumarates, or any amino or hydrazino protecting group (see, e.g., Greene et al. (1999) *Protective Groups in Organic Synthesis* (3rd Ed.) (J. Wiley Sons, Inc.));

where $R^{30}$, $R^{31}$, $R^{32}$, $R^{35}$, $R^{36}$, $R^{37}$ and $Y^2$ are unsubstituted or substituted with one or more substituents each independently selected from Z, wherein Z is selected from alkyl, alkenyl, alkynyl, aryl, cycloalkyl, cycloalkenyl, hydroxy, $S(O)_hR^{20}$, $NR^{20}R^{21}$, $COOR^{20}$, $COR^{20}$, $CONR^{20}R^{21}$, $OC(O)NR^{20}R^{21}$, $N(R^{20})C(O)R^{21}$, alkoxy, aryloxy, heteroaryl, heterocyclyl, heteroaryloxy, heterocyclyloxy, aralkyl, aralkenyl, aralkynyl, heteroaralkyl, heteroaralkenyl, heteroaralkynyl, aralkoxy, heteroaralkoxy, alkoxycarbonyl, carbamoyl, thiocarbamoyl, alkoxycarbonyl, carboxyaryl, halo, pseudohalo, haloalkyl and carboxamido; h is 0, 1 or 2; and $R^{20}$ and $R^{21}$ are each independently selected from among hydrogen, halo, pseudohalo, cyano, azido, nitro, trialkylsilyl, dialkylarylsilyl, alkyldiarylsilyl, triarylsilyl, alkyl, alkenyl, alkynyl, haloalkyl, haloalkoxy, aryl, aralkyl; aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy, amino, amido, alkylamino, dialkylamino, alkylarylamino, diarylamino and arylamino.

In certain embodiments herein, $Y^2$ is selected from any amino or hydrazino protecting group, preferably an amino or hydrazino protecting group useful in the synthesis of oligonucleotides, more preferably monomethoxytrityl (MMT), dimethoxytrityl (DMT), 9-fluorenylmethoxycarbonyl (FMOC), acetyl, trifluoroacetyl, benzoyl, or a hydrazone or oxime that is cleaved under mild acidic conditions (e.g., 100 mM acetate, pH 4.5-5.5) including, but not limited to, a hydrazone or oxime formed from a lower aliphatic aldehyde or ketone, preferably from acetone, propanal, cyclohexanone or 2-butanone. In other embodiments, particularly when X is a protected oxyamino group, the protecting group is not a phthalimidyl group.

In another embodiment, the reagents for use in the methods provided herein have formula (VIII):

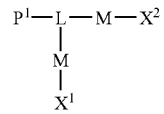

or a derivative thereof, where $P^1$, L, $X^1$ and $X^2$ are selected as above; and each M is independently selected as above. $X^1$ is preferably a protected hydrazino group and $X^2$ is preferably an orthogonally protected amino group.

In another embodiment, the reagents for use in the methods provided herein have formula (X):

$$P^1\text{—}S^1\text{—}B^1\text{-M-X},$$

or a derivative thereof, where $P^1$, $S^1$, $B^1$, M and X are selected as above. In these embodiments, $B^1$ is preferably a cytosine derivative that is substituted with -M-X at the position ortho to the amino substituent (see, e.g., FIGS. 13, 14 and 15). X is preferably a carbonyl group, more preferably an aldehyde group, or is a protected hydroxyl group.

The monomeric reagents provided herein are added to the growing oligonucleotide chain as the coupling reagent in a standard automated solid phase oligonucleotide synthesis. In the case of terminal modification, wherein purification of the final product using a lipophilic handle is required, the amino or hydrazino protecting group is DMT, or a similar moiety that is amenable to solid phase oligonucleotide synthesis. The final protected hydrazino or protected oxyamino substituted product is deprotected following high performance liquid chromatography (HPLC) purification.

1. Hydrazino Derivatives

In one preferred embodiment, the reagents for use in the methods provided herein contain a phosphorous based coupling group, as defined herein, and a hydrazino group (see, FIG. 1). Thus, in this embodiment, the compounds of formula (I) have formula (III):

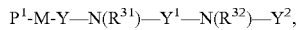

or a derivative thereof, where $P^1$ is a phosphorous based coupling group, preferably a phosphoramidite, H-phosphonate or phosphotriester, more preferably a phosphoramidite, most preferably $(NCCH_2CH_2O)(i-Pr_2N)P-O-$;

M is a divalent group having any combination, preferably 1-2000, more preferably 1-1000, particularly 1-100, most preferably 1-50 or 1-25 or 1-10, of the following groups, which can be combined in any order: arylene, heteroarylene, cycloalkylene, $C(R^1)_2$, $-C(R^1)=C(R^1)-$, $>C=C(R^2)(R^3)$, $>C(R^2)(R^3)$, $-C\equiv C-$, O, $S(A)_a$, $P(D)_b(R^1)$, $P(D)_b(ER^1)$, $N(R^1)$, $>N^+(R^2)(R^3)$ and C(E); where a is 0, 1 or 2; b is 0, 1, 2 or 3; A is O or $NR^1$; D is S or O; and E is S, O or $NR^1$; each $R^1$ is a monovalent group independently selected from hydrogen and $M^1-R^4$; each $M^1$ is a divalent group independently having any combination of the following groups, which groups can be combined in any order: a direct link, arylene, heteroarylene, cycloalkylene, $C(R^5)_2$, $-C(R^5)=C(R^5)-$, $>C=C(R^2)(R^3)$, $>C(R^2)(R^3)$, $-C\equiv C-$, O, $S(A)_a$, $P(D)_b(R^5)$, $P(D)_b(ER^5)$, $N(R^5)$, $N(COR^5)$, $>N^+(R^2)(R^3)$ and C(E); where a is 0, 1 or 2; b is 0, 1, 2 or 3; A is O or $NR^5$; D is S or O; and E is S, O or $NR^5$; $R^4$ and $R^5$ are each independently selected from among hydrogen, halo, pseudohalo, cyano, azido, nitro, $SiR^6R^7R^8$, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy and $NR^9R^{10}$; $R^9$ and $R^{10}$ are each independently selected from hydrogen, alkyl, alkenyl, alkynyl, cycloalkyl, aryl, aralkyl, heteroaryl, heteroaralkyl and heterocyclyl; $R^2$ and $R^3$ are selected from (i) or (ii) as follows: (i) $R^2$ and $R^3$ are independently selected from among hydrogen, alkyl, alkenyl, alkynyl, cycloalkyl, aryl and heteroaryl; or (ii) $R^2$ and $R^3$ together form alkylene, alkenylene or cycloalkylene; $R^6$, $R^7$ and $R^8$ are each independently a monovalent group selected from hydrogen, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy and $NR^9R^{10}$;

Y and $Y^1$ are selected as in (i) or (ii) as follows:

(i) Y is a direct link, and $Y^1$ is a direct link, $C(O)N(R^{35})$, $N(R^{35})C(O)N(R^{36})$, $C(S)N(R^{35})$, $N(R^{35})C(S)N(R^{36})$ or $C(O)N(R^{35})N(R^{36})C(O)N(R^{37})$; or (ii) Y is C(O) or OC(O), and $Y^1$ is a direct link;

where $R^{35}$, $R^{36}$ and $R^{37}$ are each independently selected from among hydrogen, alkyl, alkenyl, alkynyl, aryl, heteroaryl, aralkyl, aralkenyl, aralkynyl, heteroaralkyl, heteroaralkenyl, heteroaralkynyl, heterocyclyl and cylcoalkyl;

$Y^2$ is a salt of the hydrazino group, including but not limited to, mineral acids salts, such as but not limited to hydrochlorides and sulfates, and salts of organic acids, such as but not limited to acetates, lactates, malates, tartrates, citrates, ascorbates, succinates, butyrates, valerates and fumarates, or any amino or hydrazino protecting group, preferably an amino or hydrazino protecting group useful in the synthesis of oligonucleotides, more preferably monomethoxytrityl (MMT), dimethoxytrityl (DMT), 9-fluorenylmethoxycarbonyl (FMOC), acetyl, trifluoroacetyl (TFA), benzoyl, or a hydrazone that is cleaved under mild acidic conditions (e.g., 100 mM acetate, pH 4.5-5.5) including, but not limited to, a hydrazone formed from a lower aliphatic aldehyde or ketone, preferably from acetone or 2-butanone; and $R^{31}$ and $R^{32}$ are each independently hydrogen, alkyl, alkenyl, alkynyl, aryl, heteroaryl, aralkyl, aralkenyl, aralkynyl, heteroaralkyl, heteroaralkenyl, heteroaralkynyl, heterocyclyl or cycloalkyl;

where $R^1$, $R^2$, $R^3$, $R^4$, $R^5$, $R^6$, $R^7$, $R^8$, $R^9$, $R^{10}$, $R^{31}$, $R^{32}$, $R^{35}$, $R^{36}$, $R^{37}$ and $Y^2$ are unsubstituted or substituted with one or more substituents each independently selected from Z, as defined above.

In certain embodiments, when Y and $Y^1$ are each a direct link and the compound of formula (III) has a protected hydrazine group, the protected hydrazine group does not substitute the nucleobase of a nucleoside, nucleotide, or analog thereof.

In preferred embodiments, $R^{31}$, $R^{32}$, $R^{35}$, $R^{36}$ and $R^{37}$ are hydrogen or lower alkyl, more preferably hydrogen. In these embodiments, the compounds of formula (III) have formula (IV):

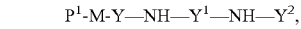

or a derivative thereof, where Y and $Y^1$ are selected from (i) or (ii) as follows:

(i) Y is a direct link, and $Y^1$ is a direct link, C(O)NH, NHC(O)NH, C(S)NH, NHC(S)NH or C(O)NHNHC(O)NH; or (ii) Y is C(O) or OC(O), and $Y^1$ is a direct link;

and $P^1$, M and $Y^2$ are selected as above.

In a preferred embodiment, the compounds for use in the methods provided herein are of formula (IV) where M has 1-50, preferably 1-25, more preferably 1-10 of the following groups, which can be combined in any order: arylene, heteroarylene, $C(R^5)_2$, O, $S(A)_a$, $N(R^5)$, $N(COR^5)$ and C(E); where a is 0, 1 or 2; A is O or $NR^5$; and E is S, O or $NR^5$; where $R^5$ is selected as above. In more preferred embodiments, M has 1-10 of the following groups, which can be combined in any order: heteroarylene, $C(R^5)_2$, $N(R^5)$ and C(E); where E is S, O or $NR^5$; where $R^5$ is selected as above. $R^5$ is preferably hydrogen; and E is preferably oxygen.

In certain embodiments herein, the group attached to Y is a heteroarylene group, preferably a nitrogen-containing heteroarylene group, preferably a pyrrolylene including 2,3-, 2,4- and 2,5-pyrrolylene, pyridylene including 2,3-, 2,4-, 2,5- and 2,6-pyridylene, triazinylene including 1,3,5-triazinylene, triazolylene including 1,2,4- and 1,2,3-triazolylene or pyrimidylene including 2,4-, 2,5- and 2,6-pyrimidylene group, more preferably a pyridylene group, most preferably a 2,5- pyridylene group. Thus, in these more preferred embodiments, M includes 2,5-pyridylene attached to Y, preferably Y is at the 2-position of the pyridylene group, and 1-9 of the following groups, which can be combined in any order: $CH_2$, NH and C(O).

In more preferred embodiments, M has the formula:

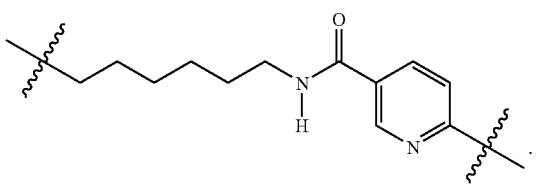

The presently most preferred compounds of formula (IV) are N-dimethoxytrityl-N'-{5-[8-(2-cyanoethyl-N,N-diisopropylphosphoramidyloxy)-2-aza-1-oxooct-1-yl]pyrid-2-yl}hydrazine or N-(9-fluorenylmethoxycarbonyl)-N'-[8-(2-cyanoethyl-N,N-diisopropylphosphoramidyloxy)-2-aza-1-thiooct-1-yl]hydrazine, having the structure:

O; and E is S, O or $NR^5$; $R^4$ and $R^5$ are each independently selected from among hydrogen, halo, pseudohalo, cyano, azido, nitro, $SiR^6R^7R^8$, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy and $NR^9R^{10}$; $R^9$ and $R^{10}$ are each independently selected from hydrogen, alkyl, alkenyl, alkynyl, cycloalkyl, aryl, aralkyl, heteroaryl, heteroaralkyl and heterocyclyl; $R^2$ and $R^3$ are selected from (i) or (ii) as follows: (i) $R^2$ and $R^3$ are independently selected from among hydrogen, alkyl, alkenyl, alkynyl, cycloalkyl, aryl and heteroaryl; or (ii) $R^2$ and $R^3$ together form alkylene, alkenylene or cycloalkylene; $R^6$, $R^7$ and $R^8$ are each independently a monovalent group selected from hydrogen, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy and $NR^9R^{10}$;

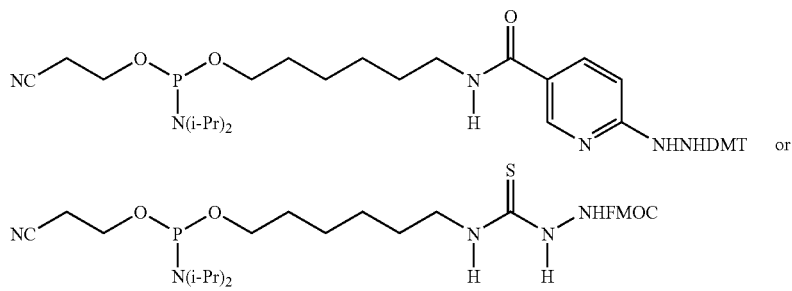

2. Carbonyl Derivatives

In another preferred embodiment, the reagents for use in the methods provided herein contain a phosphorous based coupling group, as defined herein, and a carbonyl group. Thus, in this embodiment, the compounds of formula (I) have formula (V):

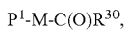

or a derivative thereof, where $P^1$ is a phosphorous based coupling group, preferably a phosphoramidite, H-phosphonate or phosphotriester, more preferably a phosphoramidite, most preferably $(NCCH_2CH_2O)(i-Pr_2N)P-O-$;

M is a divalent group having any combination, preferably 1-2000, more preferably 1-1000, particularly 1-100, most preferably 1-50 or 1-25 or 1-10, of the following groups, which can be combined in any order: arylene, heteroarylene, cycloalkylene, $C(R^1)_2$, $-C(R^1)=C(R^1)-$, $>C=C(R^2)(R^3)$, $>C(R^2)(R^3)$, $-C\equiv C-$, O, $S(A)_a$, $P(D)_b(R^1)$, $P(D)_b(ER^1)$, $N(R^1)$, $>N^+(R^2)(R^3)$ and C(E); where a is 0, 1 or 2; b is 0, 1, 2 or 3; A is O or $NR^1$; D is S or O; and E is S, O or $NR^1$; each $R^1$ is a monovalent group independently selected from hydrogen and $M^1-R^4$; each $M^1$ is a divalent group independently having any combination of the following groups, which groups can be combined in any order: a direct link, arylene, heteroarylene, cycloalkylene, $C(R^5)_2$, $-C(R^5)=C(R^5)-$, $>C=C(R^2)(R^3)$, $>C(R^2)(R^3)$, $-C\equiv C-$, O, $S(A)_a$, $P(D)_b(R^5)$, $P(D)_b(ER^5)$, $N(R^5)$, $N(COR^5)$, $>N^+(R^2)(R^3)$ and C(E); where a is 0, 1 or 2; b is 0, 1, 2 or 3; A is O or $NR^5$; D is S or $R^{30}$ is hydrogen, alkyl, alkenyl, alkynyl, aryl, heteroaryl, aralkyl, aralkenyl, aralkynyl, heteroaralkyl, heteroaralkenyl, heteroaralkynyl, heterocyclyl or cycloalkyl;

where $R^1$, $R^2$, $R^3$, $R^4$, $R^5$, $R^6$, $R^7$, $R^8$, $R^9$, $R^{10}$ and $R^{30}$ are unsubstituted or substituted with one or more substituents each independently selected from Z, as defined above.

In certain embodiments, particularly when $R^{30}$ is hydrogen, the carbonyl group does not substitute the nucleobase of a nucleoside, nucleotide, or analog thereof.

In preferred embodiments, $R^{30}$ is hydrogen or lower alkyl, more preferably hydrogen or methyl, most preferably hydrogen. In these embodiments, the compounds of formula (V) have formulae (VI):

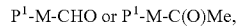

or a derivative thereof, where $P^1$ and M are selected as above.

In a preferred embodiment, the compounds for use in the methods provided herein are of formula (VI) where M has 1-50, preferably 1-25, more preferably 1-10 of the following groups, which can be combined in any order: arylene, heteroarylene, $C(R^5)_2$, O, $S(A)_a$, $N(R^5)$, $N(COR^5)$ and C(E); where a is 0, 1 or 2; A is O or $NR^5$; and E is S, O or $NR^5$; where $R^5$ is selected as above. In more preferred embodiments, M has 1-10 of the following groups, which can be combined in any order: arylene, $C(R^5)_2$, $N(R^5)$ and C(E); where E is S, O or $NR^1$; where $R^5$ is selected as above. $R^5$ is preferably hydrogen; and E is preferably oxygen. In certain embodiments herein, the group attached to CHO or C(O)Me is a arylene group, preferably a monocyclic arylene group, more preferably phenylene. Thus, in these more preferred embodiments, M includes phenylene attached to CHO or C(O)Me, and 1-9 of the following groups, which can be combined in any order: $CH_2$, NH and C(O).

In more preferred embodiments, M has the formula:

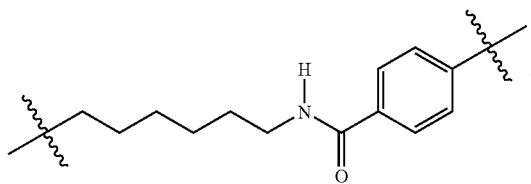

The presently most preferred compounds of formulae (VI) are 4-[8-(2-cyanoethyl-N,N-diisopropylphosphoramidyloxy)-2-aza-1-oxooct-1-yl]benzaldehyde, 4-[8-(2-cyanoethyl-N,N-diisopropylphosphoramidyloxy)-2-aza-1-oxooct-1-yl]acetophenone and N-[6-(2-cyanoethyl-N,N-diisopropylphosphoramidyloxy)hexyl]4-oxopentanamide, having the structures:

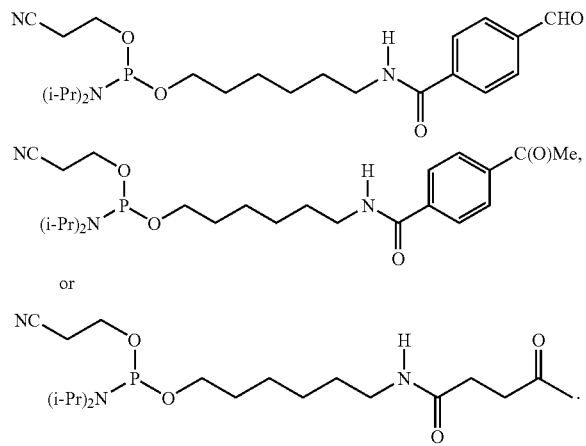

3. Oxyamino Derivatives

In one preferred embodiment, the reagents for use in the methods provided herein contain a phosphorous based coupling group, as defined herein, and an oxyamino group. The oxyamino group is preferably protected as described above. Thus, in this embodiment, the compounds of formula (I) have formula (VII):

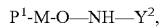

or a derivative thereof, where $P^1$ is a phosphorous based coupling group, preferably a phosphoramidite, H-phosphonate or phosphotriester, more preferably a phosphoramidite, most preferably $(NCCH_2CH_2O)(i-Pr_2N)P$—O—; and M is a divalent group having any combination, preferably 1-2000, more preferably 1-1000, particularly 1-100, most preferably 1-50 or 1-25 or 1-10, of the following groups, which can be combined in any order: arylene, heteroarylene, cycloalkylene, $C(R^1)_2$, —$C(R^1)$=$C(R^1)$—, >C=$C(R^2)(R^3)$, >$C(R^2)(R^3)$, —C≡C—, O, $S(A)_a$, $P(D)_b(R^1)$, $P(D)_b(ER^1)$, $N(R^1)$, >$N^+(R^2)(R^3)$ and C(E); where a is 0, 1 or 2; b is 0, 1, 2 or 3; A is O or $NR^1$; D is S or O; and E is S, O or $NR^1$; each $R^1$ is a monovalent group independently selected from hydrogen and $M^1$-$R^4$; each $M^1$ is a divalent group independently having any combination of the following groups, which groups can be combined in any order: a direct link, arylene, heteroarylene, cycloalkylene, $C(R^5)_2$, —$C(R^5)$=$C(R^5)$—, >C=$C(R^2)(R^3)$, >$C(R^2)(R^3)$, —C≡C—, O, $S(A)_a$, $P(D)_b(R^5)$, $P(D)_b(ER^5)$, $N(R^5)$, $N(COR^5)$, >$N^+(R^2)(R^3)$ and C(E); where a is 0, 1 or 2; b is 0, 1, 2 or 3; A is O or $NR^5$; D is S or O; and E is S, O or $NR^5$; $R^4$ and $R^5$ are each independently selected from the among hydrogen, halo, pseudohalo, cyano, azido, nitro, $SiR^6R^7R^8$, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy and $NR^9R^{10}$; $R^9$ and $R^{10}$ are each independently selected from hydrogen, alkyl, alkenyl, alkynyl, cycloalkyl, aryl, aralkyl, heteroaryl, heteroaralkyl and heterocyclyl; $R^2$ and $R^3$ are selected from (i) or (ii) as follows: (i) $R^2$ and $R^3$ are independently selected from the among hydrogen, alkyl, alkenyl, alkynyl, cycloalkyl, aryl and heteroaryl; or (ii) $R^2$ and $R^3$ together form alkylene, alkenylene or cycloalkylene; $R^6$, $R^7$ and $R^8$ are each independently a monovalent group selected from hydrogen, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy and $NR^9R^{10}$;

$Y^2$ is a salt of the oxyamino group, including but not limited to, mineral acids salts, such as but not limited to hydrochlorides and sulfates, and salts of organic acids, such as but not limited to acetates, lactates, malates, tartrates, citrates, ascorbates, succinates, butyrates, valerates and fumarates, or any amino protecting group, preferably an amino protecting group useful in the synthesis of oligonucleotides, more preferably monomethoxytrityl (MMT), dimethoxytrityl (DMT), 9-fluorenylmethoxycarbonyl (FMOC), acetyl, trifluoroacetyl (TFA), benzoyl, or an oxime that is cleaved under mild acidic conditions (e q, 100 mM acetate, pH 4.5-5.5) including, but not limited to, an oxime formed from a lower aliphatic aldehyde or ketone, preferably from acetone or 2-butanone;

where $R^1$, $R^2$, $R^3$, $R^4$, $R^5$, $R^6$, $R^7$, $R^8$, $R^9$, $R^{10}$ and $Y^2$ are unsubstituted or substituted with one or more substituents each independently selected from Z, as defined above;

with the proviso that M is not tetra(ethyleneoxy) (i.e., $(CH_2CH_2O)_4$, TEG).

In certain embodiments, the protected oxyamino group does not substitute the nucleobase of a nucleoside, nucleotide, or analog thereof. In other embodiments, the compounds have formula (VII) where the protected oxyamino group does not substitute the 2', 3' or 5', particularly the 2', position of a nucleoside, nucleotide, or analog thereof. In certain embodiments, the protected oxyamino group does not substitute the nucleobase of a nucleoside, nucleotide, or analog thereof.

In a preferred embodiment, the compounds for use in the methods provided herein are of formula (VII) where M has 1-50, preferably 1-25, more preferably 1-10 of the following groups, which can be combined in any order: arylene, heteroarylene, $C(R^5)_2$, O, $S(A)_a$, $N(R^5)$, $N(COR^5)$ and C(E); where a is 0, 1 or 2; A is O or $NR^5$; and E is S, O or $NR^5$; where $R^5$ is selected as above. In more preferred embodiments, M has 1-10 of the following groups, which can be combined in any order: heteroarylene, $C(R^5)_2$, $N(R^5)$ and C(E); where E is S, O or $NR^5$; where $R^5$ is selected as above. $R^5$ is preferably hydrogen; and E is preferably oxygen. In certain embodiments herein, the group attached to the oxygen of the oxyamino group is an arylene or heteroarylene group, preferably a nitrogen-containing heteroarylene group, more preferably pyridylene. Thus, in these more preferred embodiments, M includes pyridylene attached to the oxygen of the oxyamino group and 1-9 of the following groups, which can be combined in any order: CH$_2$, NH and C(O).

In more preferred embodiments, M has the formula:

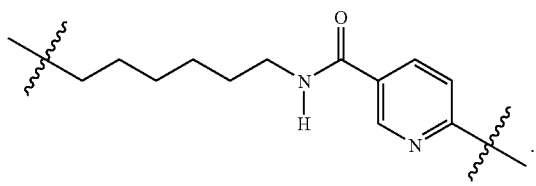

The presently most preferred compound of formula (VII) is N-monomethoxytrityl-O-{5-[8-(2-cyanoethyl-N,N-diisopropylphosphoramidyloxy)-2-aza-1-oxooct-1-yl]pyrid-2-yl}oxyamine, having the structure:

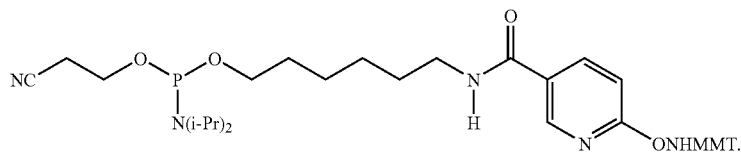

4. Phosphoramidites for Conjugation of an Oligonucleotide with Two Other Components In another embodiment, the reagents for use in the methods provided herein have formula (VIII):

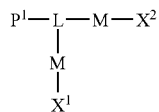

or a derivative thereof, where P$^1$, L, X$^1$ and X$^2$ are selected as above; and each M is independently selected as above.

In preferred embodiments, the reagents of formula (VIII) are those where X$^1$ is a protected hydrazino group and X$^2$ is an orthogonally protected amino group. Alternatively, X$^2$ is, in certain embodiments, an amino group that is conjugated to a fluorophore F*, such as an ethidium bromide derivative or analog.

In certain embodiments, each M is preferably an alkylene group, more preferably a lower alkylene group. In other embodiments, each M preferably has a heteroarylene group, more preferably a 2,5-pyridylene group, and 1-9 of the following groups, which can be combined in any order: C(R$^1$)$_2$, N(R$^1$) and C(E), where R$^1$ and E are selected as above. R$^1$ is preferably hydrogen and E is preferably oxygen.

L is preferably a trivalent group of formula C$_n$H$_{2n-1}$, where n is about 2 to about 10, more preferably about 2 to about 6, most preferably about 3 to about 5 or 6, and optionally can possess one or more, preferably 1-10, more preferably 1 or 2, of the following groups, which can be combined in any order: N(R$^1$) and C(E), where R$^1$ and E are selected as above. In more preferred embodiments, the group:

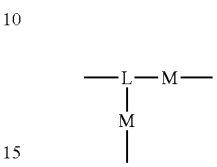

has either of the formulae:

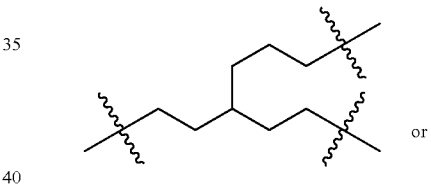

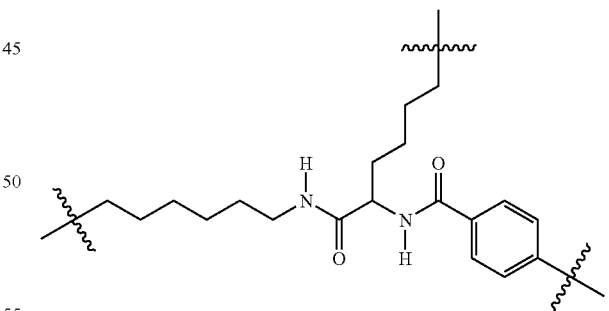

Thus, in these more preferred embodiments, the compound of formula (VIII) has either of the formulae:

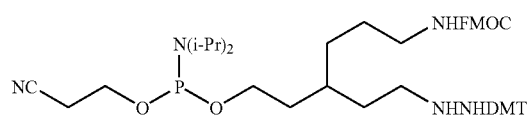

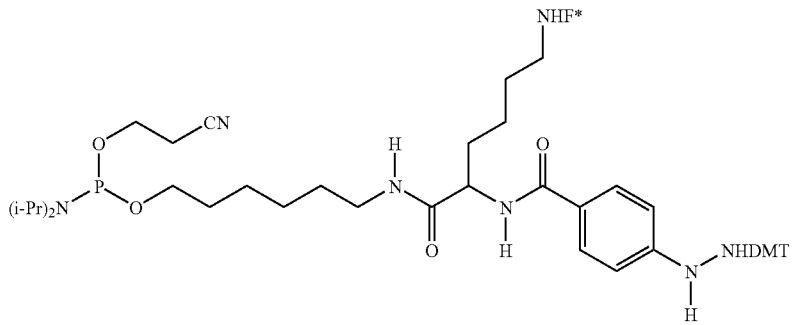

where F* is a fluorophore, such a an ethidium bromide derivative or analog.

5. Phosphoramidites for Incorporation at an Internal Position of an Oligonucleotide In another embodiment, the reagents for use in the methods provided herein have formula (X):

or a derivative thereof, where $P^1$, $S^1$, $B^1$, M and X are selected as above. In these embodiments, $B^1$ is preferably a cytosine derivative that is substituted with -M-X at the position ortho to the amino substituent (see, e.g., FIGS. 13, 14 and 15). X is preferably a carbonyl group, more preferably an aldehyde group, or is a protected hydroxyl group.

In more preferred embodiments, the reagents are of formula (X) where M includes an alkynyl group. Thus, in these embodiments, M has any combination, preferably 1 to 100, more preferably 1 to 50, most preferably 1 to 10, of the following groups: —C≡C—, $C(R^1)_2$, $N(R^1)$, arylene and heteroarylene, which groups can be combined in any order. In certain embodiments, $R^1$ is hydrogen and M has —C≡C— and 1 to 9 of the following groups: $CH_2$, NH and arylene, preferably phenylene.

In more preferred embodiments, the compounds are of formula (X) where M is —C≡C—$CH_2$— or —C≡C—$CH_2$—NH-(1,4-phenylene). Thus, in these more preferred embodiments, the compounds of formula (X) have the structures:

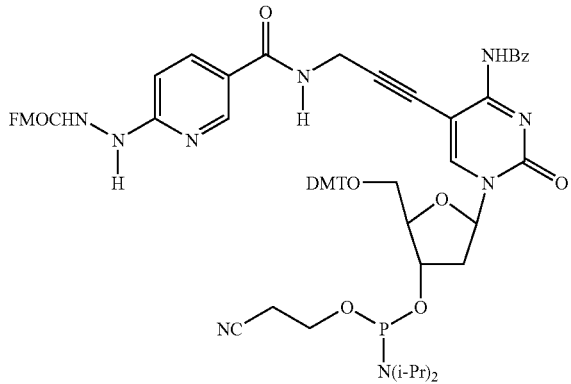

or

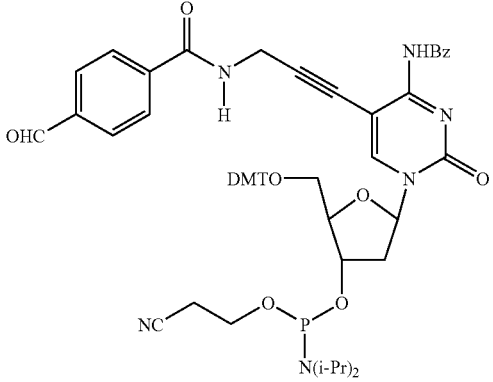

6. Methods of Preparation of the Phosphoramidites

Methods of preparation of the phosphoramidites provided herein are also provided. The methods involve the steps of (i) derivatizing a carboxylic acid selected from an ω-carbonyl, an ω-protected hydrazino, and an ω-protected oxyamino substituted carboxylic acid as the corresponding active ester, including, but not limited to, aryl, heteroaryl, succinimidyl, maleimidyl, phthalimidyl and naphthimidyl, preferably succinimidyl, esters by reacting the carboxylic acid with the appropriate aryl, heteroaryl, succinimidyl, maleimidyl, phthalimidyl or naphthimidyl alcohol, preferably N-hydroxysuccinimide, under dehydrating conditions, including, but not limited to, in the presence of a carbodiimide, such as dicyclohexylcarbodiimide; (ii) reacting the resulting active ester with an α,ω-aminoalcohol, preferably 1-amino-6-hydroxyhexane, to provide an ω-hydroxyamide; and (iii) derivatizing the ω-hydroxy group as the corresponding phosphoramidite by reaction with an active phorphorylating compound, including, but not limited to, diisopropyl pyrrolidinyl phosphoryl chloride or 2-cyanoethyl-N,N,N',N'-tetraisopropylphosphorodiamidite, preferably 2-cyanoethyl-N,N,N',N'-tetraisopropylphosphorodiamidite. Preferred ω-carbonyl carboxylic acids include 4-formylbenzoic acid, levulinic acid and 4-carboxyacetophenone. Preferred ω-protected hydrazino carboxylic acids include 6-(N'-dimethoxytrityl)hydrazinonicotinic acid. Preferred ω-protected oxyamino carboxylic acids include 6-(N-dimethoxytrityl)oxyaminonicotinic acid.

B. Modified Oligonucleotides, Immobilized Oligonucleotides and Oligonucleotide Conjugates

1. Modified Oligonucleotides

Provided herein are modified oligonucleotides that possess a hydrazino group (see, FIG. 1), an oxyamino group, or a carbonyl group. These modified oligonucleotides are synthesized directly during standard solid phase synthesis without the need for post synthetic modification to produce the hydrazino, oxyamino, or carbonyl group. The modified oligonucleotides can be immobilized or conjugated through the formation of covalent hydrazone or oxime bonds. Such hydrazone or oxime bonds can be formed by reaction of the hydrazino, oxyamino or carbonyl modified oligonucleotides with appropriately derivatized solid surfaces, as described herein; or second components, including, but not limited to, biopolymers as defined herein, macromolecules as defined herein, polymers including, but not limited to, polyamines, polyamides, polyethers and polyethylene glycols, and other compounds of interest herein for use in assays, kits, diagnostic arrays, and the like, including, but not limited to, intercalators, vitamins, reporter molecules, cholesterols, phospholipids, biotin, phenazine, phenanthridine, anthraquinone, acridine, fluoresceins, rhodamines, coumarins, dyes, antibodies, haptens, antigens, enzymes, and detection reagents including, but not limited to, fluorophores, metals including, but not limited to, gold, metal chelates, chromophores, fluorophore precursors and chromophore precursors, that are modified to possess a hydrazino, oxyamino or carbonyl group that is complementary to the carbonyl, oxyamino or hydrazino group of the oligonucleotide of formula (II) for formation of hydrazone or oxime linkage. Fluorophore precursors and chromophore precursors are compounds that react with the hydrazino, oxyamino or carbonyl group of the modified oligonucleotide to form a fluorogenic or chromogenic group for analysis. Fluorophore precursors and chromophore precursors are well know to those of skill in the art, and include, but are not limited to, 3-(4-carboxybenzoyl) quinoline-2-carboxaldehyde (CBQCA) and 3-(2-furoyl) quinoline-2-carboxaldehyde (FQ), sold by Molecular Probes, Inc. (Eugene, Oreg.). Importantly, the reaction to form the immobilized oligonucleotide or oligonucleotide conjugate can be performed under aqueous conditions without the need for catalysis.

The modified oligonucleotides provided herein have formula (II):

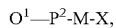

or a derivative thereof, where $O^1$ is a first component that is an oligonucleotide or analog thereof, such as a protein nucleic acid (PNA); $P^2$ is a phosphorous linking group resulting from the coupling of a compound of formula (I) with the oligonucleotide or analog thereof, preferably a phosphodiester group; and M and X are as defined above for the hydrazino, oxyamino, and carbonyl derivatives of phosphoramidites.

In certain embodiments, the oligonucleotide analogs of formula (II) are selected with the proviso that if X is CHO, then M is not undecylenecarbonylaminomethylene (n-$C_{11}H_{22}C(O)NHCH_2$) or $C_{1-20}$alkylene. In other embodiments, the oligonucleotide analogs are of formula (II) where X is not an oxyamino or protected oxyamino group. In further embodiments, the oligonucleotide analogs are of formula (II) where X is not a hydrazide (—C(O)—$NHNH_2$) group. In particular embodiments, the oligonucleotide analogs of formula (II) are selected with the proviso that if X is —$NHNH_2$, then M is not —$CH(CH_2OH)(CH_2)_6NHCO$-5-pyrid-2-ylene.

In other embodiments, the oligonucleotide analogs of formula (II) are selected with the proviso that $P^2$ is not a phosphoramidate group.

Thus, in more preferred embodiments, the modified oligonucleotides have formulae:

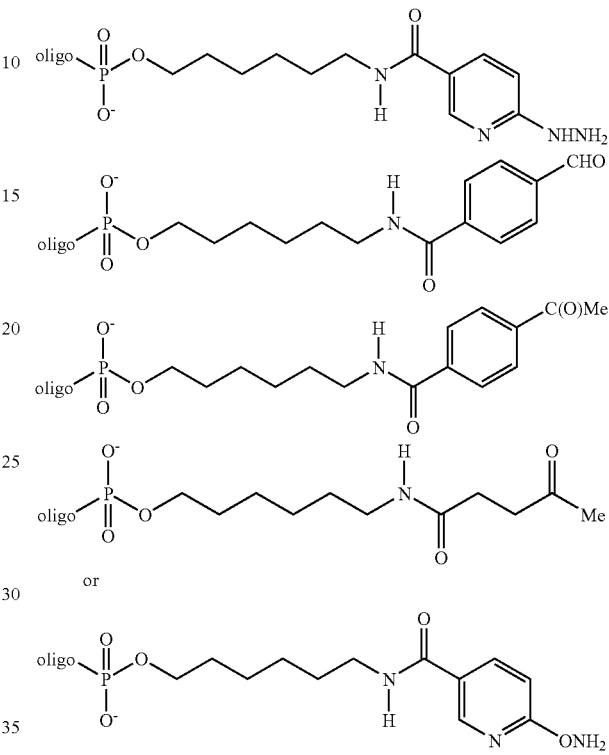

In another embodiment, provided herein are oligonucleotide analogs of formula (IX):

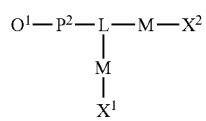

or a derivative thereof, where $O^1$, $P^2$, L, $X^1$ and $X^2$ are selected as above; and each M is independently selected as above. In these embodiments, $X^1$ also includes the free hydrazino and oxyamino groups resulting from deprotection. $X^2$ also includes the free amino or hydroxy group resulting from deprotection.

In preferred embodiments, the modified oligonucleotides have formula (IX) where $X^1$ is protected or unprotected hydrazino and $X^2$ is protected or unprotected amino. In other embodiments herein, $X^2$ is an amino group that is conjugated to a fluorophore F*, such as an ethidium bromide analog or derivative.

In more preferred embodiments, the modified oligonucleotides have formula (IX) where $X^1$ is —$NHNH_2$ and $X^2$ is —$NH_2$ or —NHF*. In these embodiments, each M is preferably an alkylene group, more preferably a lower alkylene group. In other embodiments, each M preferably has a heteroarylene group, more preferably a 2,5-pyridylene group, and 1-9 of the following groups, which can be combined in any order: C(R$^1$)$_2$, N(R$^1$) and C(E), where R$^1$ and E are selected as above. R$^1$ is preferably hydrogen and E is preferably oxygen.

L is preferably a trivalent group of formula C$_n$H$_{2n-1}$, where n is about 2 to about 10, more preferably about 2 to about 6, most preferably about 3 to about 5 or 6, and optionally can possess one or more, preferably 1-10, more preferably 1 or 2, of the following groups, which can be combined in any order: N(R$^1$) and C(E), where R$^1$ and E are selected as above. In more preferred embodiments, the group:

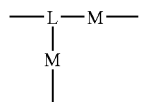

has the formula:

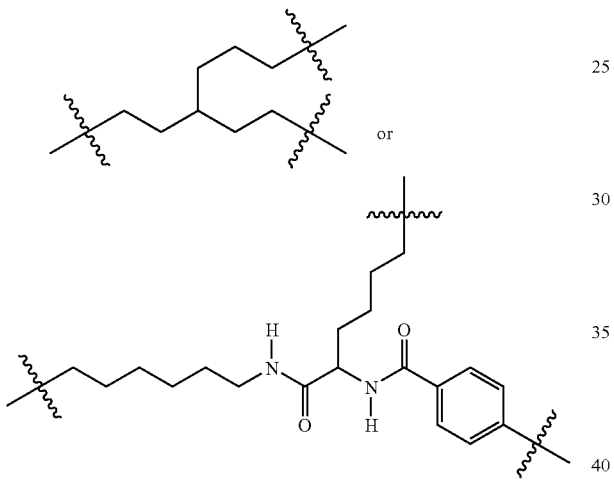

Thus, in these more preferred embodiments, the modified oligonucleotide of formula (IX) has the structure:

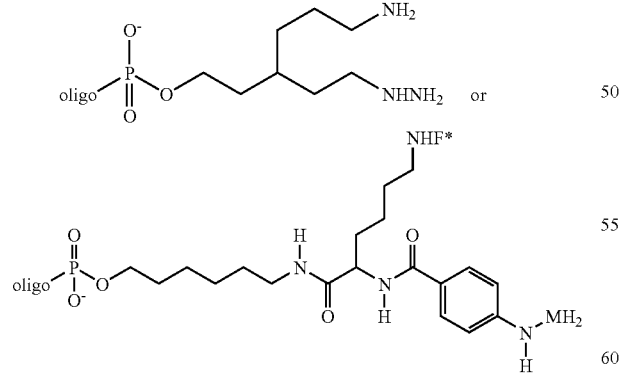

where F* is a fluorophore, such as an ethidium bromide analog or derivative.

In another embodiment, oligonucleotide analogs of formula (XI) are provided:

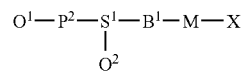

or a derivative thereof, where O$^1$, P$^2$, S$^1$, B$^1$, M and X are selected as above; and O$^2$ is an oligonucleotide, or analog thereof such as a PNA. In these embodiments, X also includes the free hydrazino and oxyamino groups resulting from deprotection.

Figure 13:
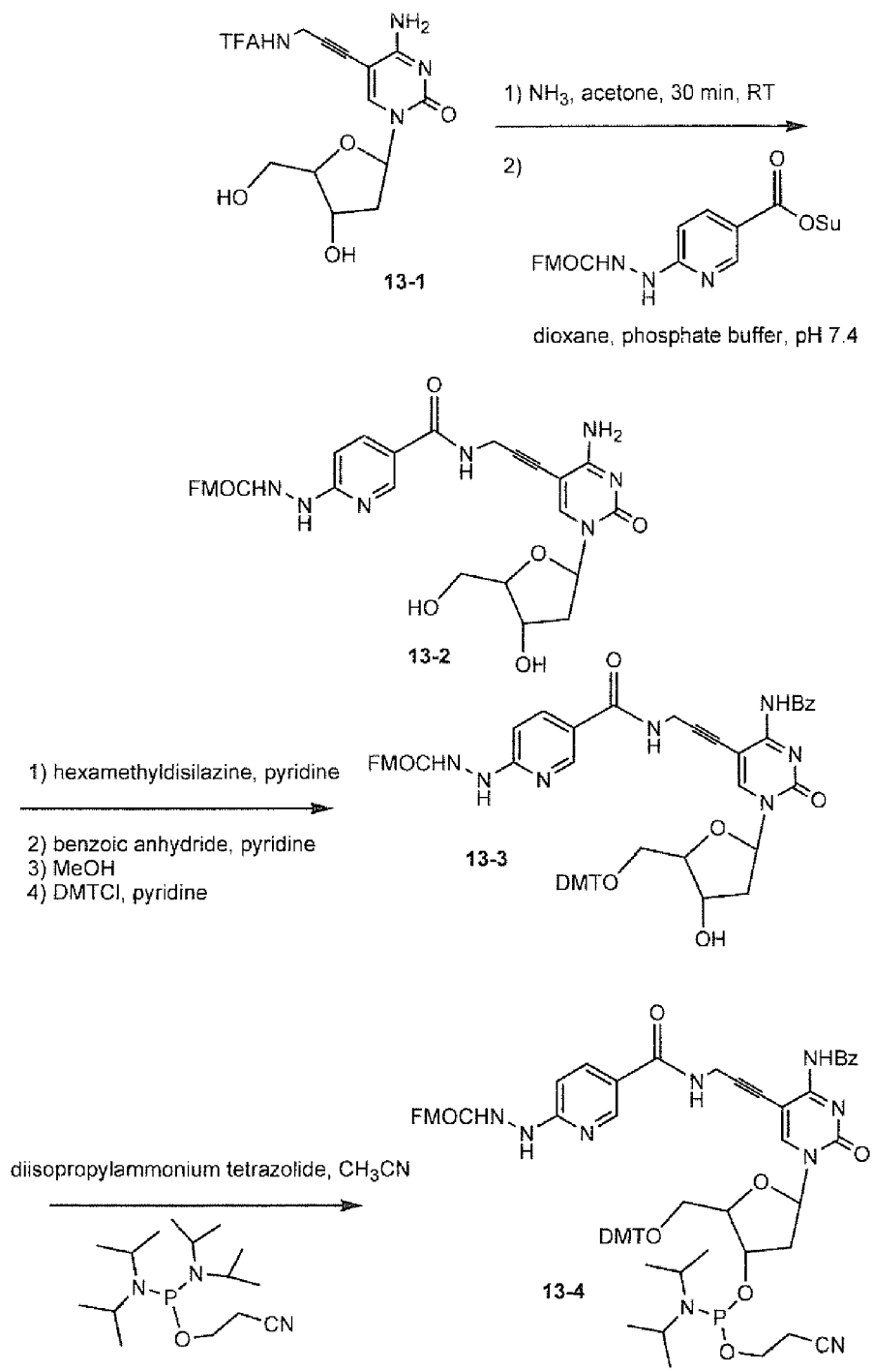
FIG. 13 shows the synthesis of a fluorenylmethoxycarbonyl (FMOC)-protected hydrazino nucleoside amidite provided herein for incorporation at an internal position of an oligonucleotide.
Figure 14:
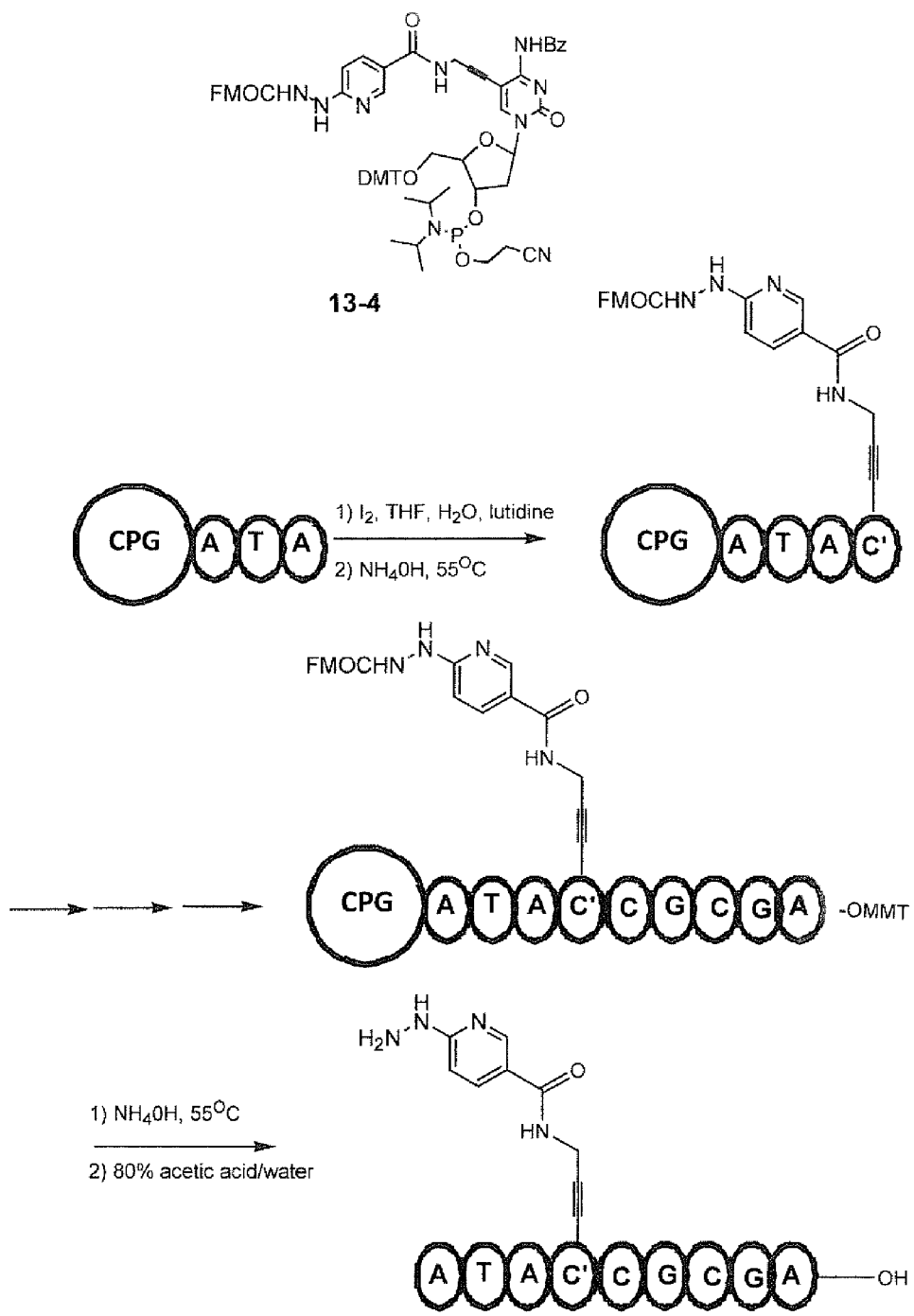
FIG. 14 illustrates incorporation of the FMOC-protected hydrazino nucleoside amidite of FIG. 16 into an oligonucleotide during solid phase synthesis and cleavage of the hydrazino modified oligonucleotide from the solid surface.
Figure 15A:
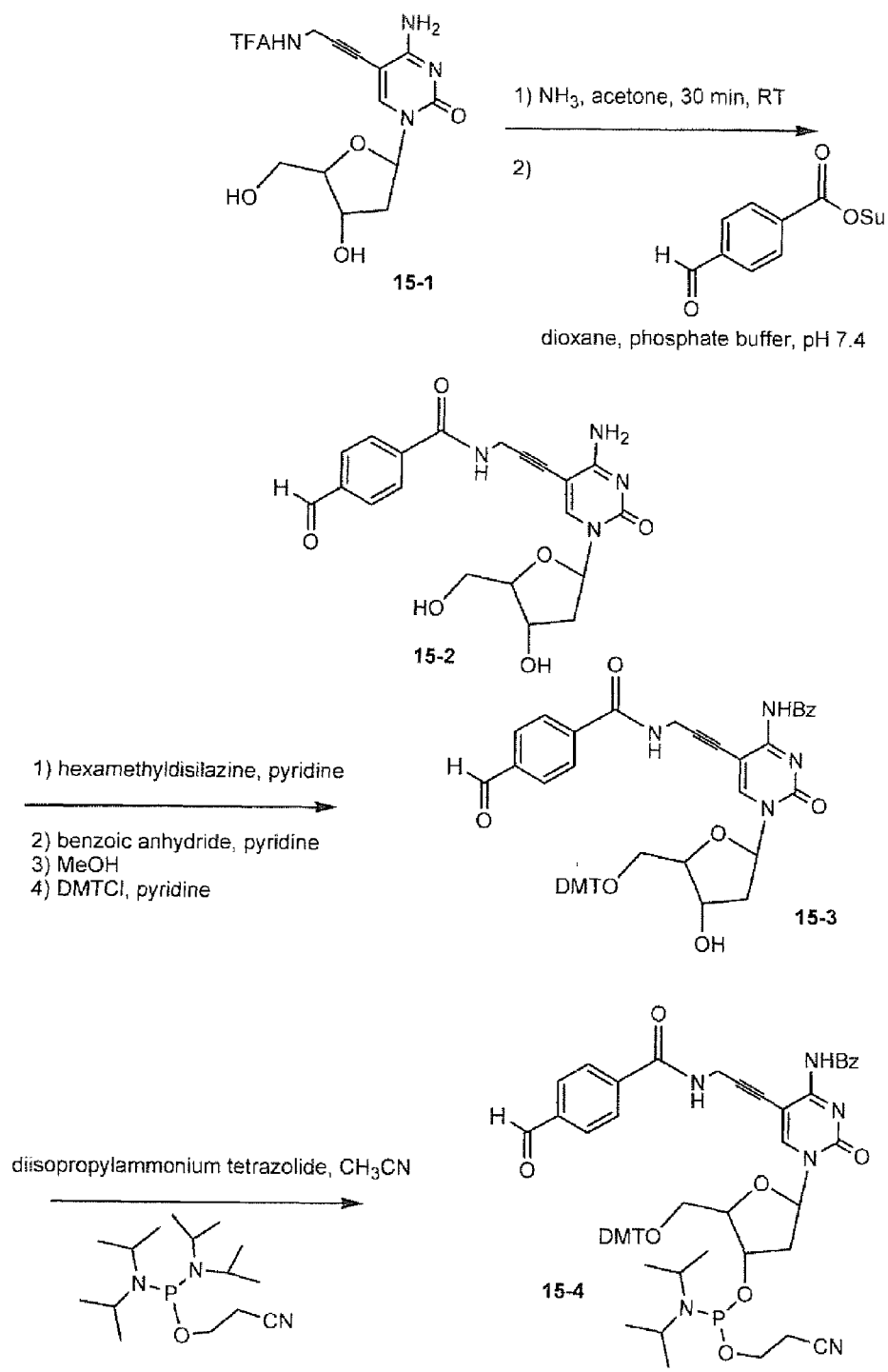
FIG. 15 illustrates the synthesis and incorporation of an aldehyde-substituted nucleoside amidite provided herein at an internal position of an oligonucleotide during solid phase synthesis and subsequent cleavage of the aldehyde modified oligonucleotide from the solid surface.
Figure 15B:
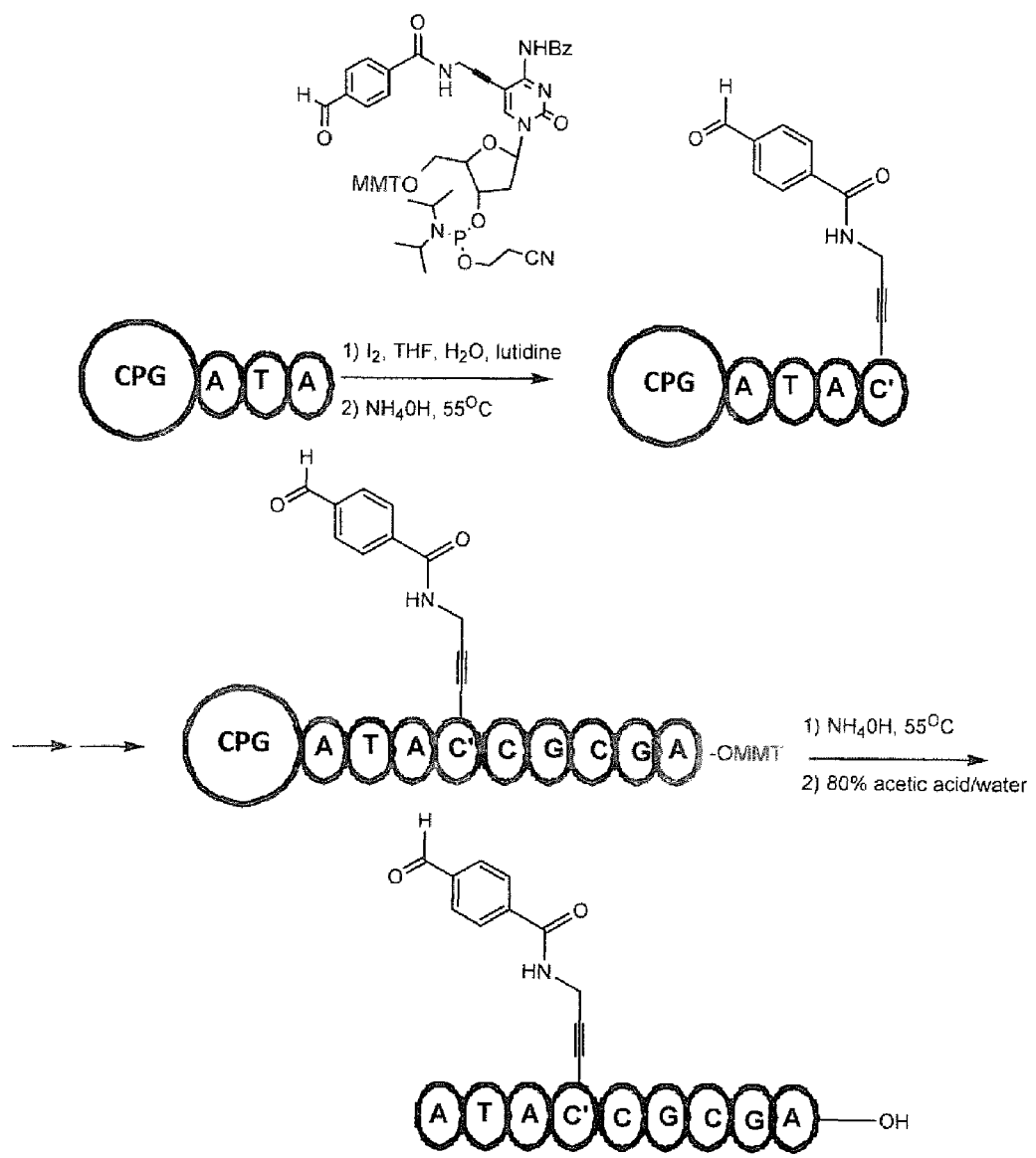

In these embodiments, B$^1$ is preferably a cytosine derivative that is substituted with -M-X at the position ortho to the amino substituent (see, e.g., FIGS. 13, 14 and 15). X is preferably a carbonyl group, more preferably an aldehyde group, or is a hydroxyl group. The hydroxyl group is reacted with a reagent of formula (I) to provide certain of the hydrazino, oxyamino or carbonyl modified oligonucleotides provided herein.

In more preferred embodiments, M includes an alkynyl group. Thus, in these embodiments, M has any combination, preferably 1 to 100, more preferably 1 to 50, most preferably 1 to 10, of the following groups: —C≡C—, C(R$^1$)$_2$, N(R$^1$), arylene and heteroarylene, which groups can be combined in any order. In certain embodiments, R$^1$ is hydrogen and M has —C≡C— and 1 to 9 of the following groups: CH$_2$, NH and arylene, preferably phenylene.

In more preferred embodiments, M is —C≡C—CH$_2$— or —C≡C—CH$_2$—NH-(1,4-phenylene). Thus, in these more preferred embodiments, the modified oligonucleotides of formula (XI) have the structure:

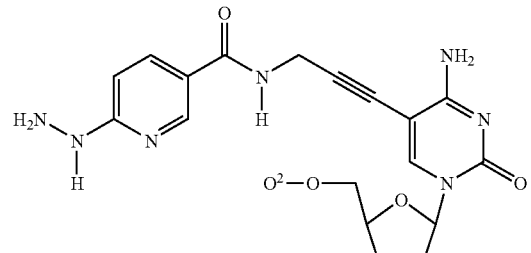

or

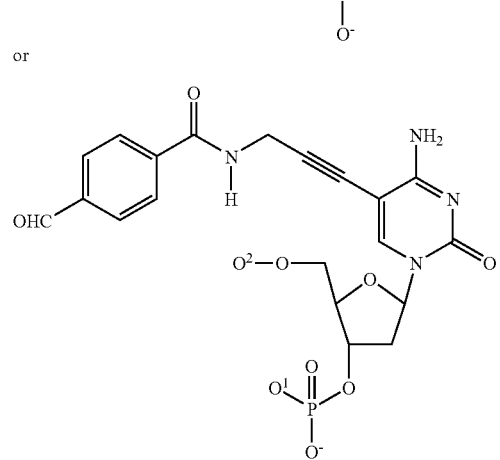

where O$^1$ and O$^2$ are selected as above.

Methods of preparation of the modified oligonucleotides provided herein are also provided. The methods involve the steps of: (i) synthesizing an oligonucleotide on a solid phase synthesizer wherein at least one of the monomers is a phosphoramidite provided herein; and (ii) removing the hydrazino or oxyamino protecting group; and (iii) cleaving the modified oligonucleotide from the solid surface. Steps (ii) and (iii) are performed in either order.

2. Immobilized Oligonucleotides

Oligonucleotides immobilized through a hydrazone or oxime linkage to a solid surface are provided. The oligonucleotides have formula (II) or (XI) and are modified with a hydrazino, oxyamino, or carbonyl moiety; or have formula (IX) and are modified with a hydrazino or oxyamino moiety, and an amino or hydroxy group. Reaction of the modified oligonucleotide with an appropriately functionalized solid surface provides an immobilized oligonucleotide for use in diagnostic probe assays, DNA amplification by solid phase polymerase chain reactions (PCR), molecular computing (see, e.g., Adleman (1994) *Science* 266:1021-1024; Kari (1997) *Mathematical Intelligencer* 19:9-22; Frutos et al. (1997) *Nucleic Acids Res.* 25:4748; Smith et al. (1998) *J. Comp. Biol.* 5:255; Liu et al. (1998) *J. Comp. Biol.* 5:267; Frutos et al. (1998) *J. Am. Chem. Soc.* 120:10277; Wang et al. (1999) *Biosystems* 52:189-191; Liu et al. (1999) *Biosystems* 52:25-33; Liu et al. (2000) *Nature* 403:175-179; European Patent Application Publication No. EP 0 772 135; Reed et al. (June 2000) *Scientific American*: 86-93), molecular addressing (Niemeyer et al. (1994) *Nucl. Acids Res.* 22(25):5530-5539), DNA sequencing by mass spectrometry (see, e.g., U.S. Pat. Nos. 6,074,823 and 5,547,835) and in studying the molecular electronics of DNA (see, e.g., U.S. Pat. Nos. 6,071,699, 6,066,448, 5,952,172 and 5,824,473).

Importantly, in certain embodiments, the reaction to form the immobilized oligonucleotide can be performed under aqueous conditions without the need for additional reagents, such as a reducing agent.

Appropriately modified solid surfaces can be prepared by the methods provided herein and possess carbonyl, oxyamino, or hydrazino groups complementary to the modified oligonucleotide. Reaction of the modified oligonucleotide with the modified solid surface results in covalent attachment of the oligonucleotide to the solid surface through a hydrazone or oxime linkage.

In embodiments where X or $X^1$ of the modified oligonucleotide is a hydrazino or oxyamino group, the solid surface can be modified to possess an epoxide, α-bromocarbonyl, maleimide, maleic anhydride, isothiocyanate or isocyanate group. Such solid surfaces can be prepared by methods provided herein or other methods well known to those of skill in the art. For example, reaction of pentafluorophenyl 4-isothiocyanatobenzoate with an amino or hydroxy solid surface results in formation of an isothiocyanato modified solid surface. Some of these surfaces are commercially available from, e.g., Pierce (Rockford, Ill.), SINTEF Applied Chemistry (Trondheim, Norway), Rapp Polymere Gmbh (Tubingen, Germany), and Dyno Particles AS (Trondheim, Norway). Reaction of the hydrazino or oxyamino group of the modified oligonucleotide with the epoxide, α-bromocarbonyl, maleimide, maleic anhydride, isothiocyanate or isocyanate group of the solid surface results in covalent attachment of the oligonucleotide to the solid surface.

In certain embodiments, particularly where X is an oxyamino group, the immobilized oligonucleotides are selected such that the solid surface is not modified with an aldehyde or epoxide group.

Figure 21:
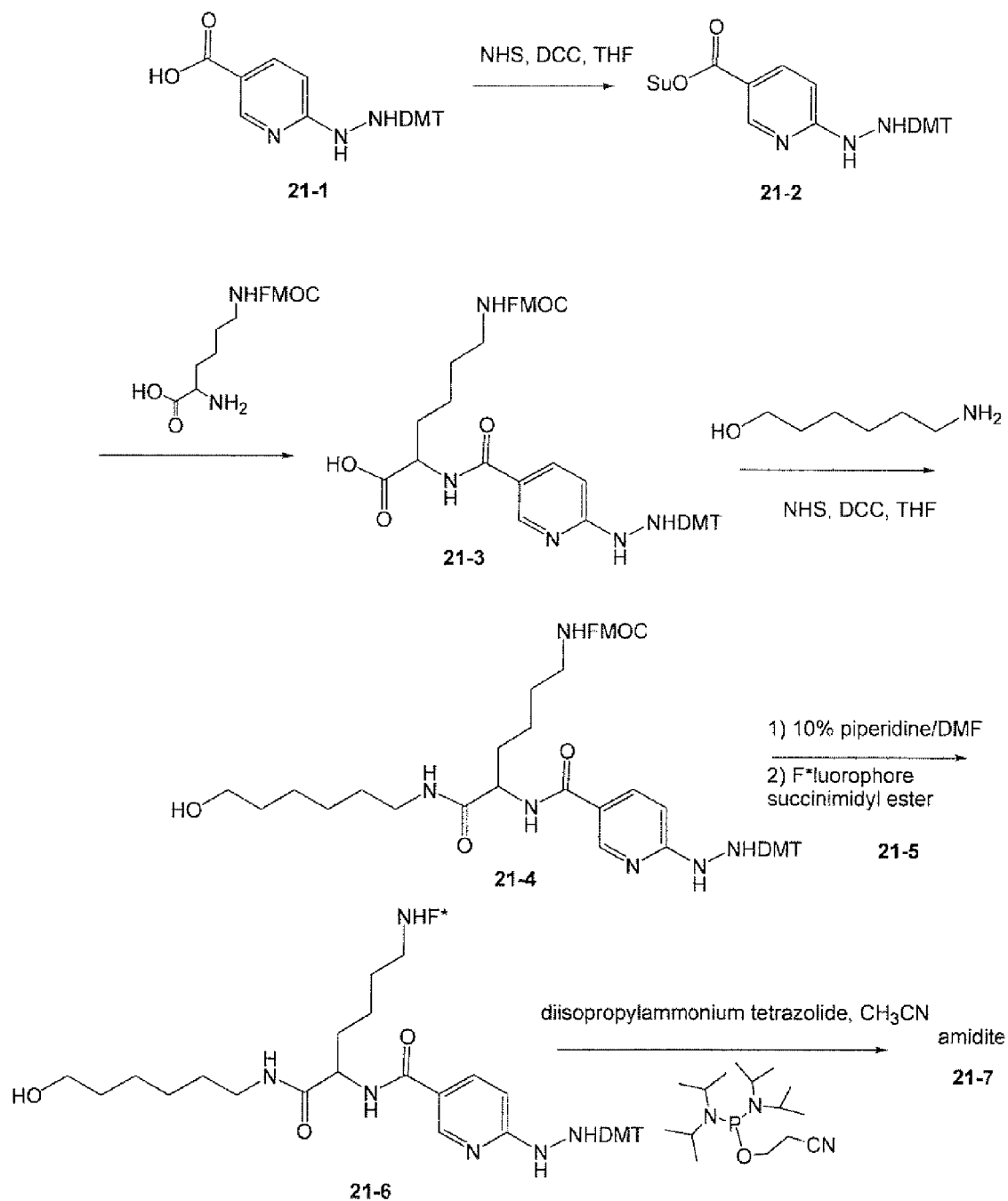
FIG. 21 illustrates the synthesis of a fluorophore containing hydrazino amidite.

In embodiments where the modified oligonucleotide is of formula (IX), the $X^2$ group provides a site for conjugation of a second component to the immobilized oligonucleotide. As shown in FIG. 21, the conjucation partner, F*, in these embodiments is preferably a compound that does not appreciably fluoresce, including, but not limited to, an ethidium bromide derivative. Intercalation of F* into the oligonucleotide duplex leads to enhanced fluorescence of F*.

3. Oligonucleotide Conjugates

Oligonucleotide first components conjugated to second components, including, but not limited to, biopolymers as defined herein, macromolecules as defined herein, polymers including, but not limited to, polyamines, polyamides, polyethers and polyethylene glycols, and other compounds of interest herein for use in assays, kits, diagnostic arrays, and the like, including, but not limited to, intercalators, vitamins, reporter molecules, cholesterols, phospholipids, biotin, phenazine, phenanthridine, anthraquinone, acridine, fluoresceins, rhodamines, coumarins, dyes, antibodies, haptens, antigens, enzymes, and detection reagents including, but not limited to, fluorophores, metals including, but not limited to, gold, metal chelates, chromophores, fluorophore precursors and chromophore precursors, that are modified to possess a hydrazino, oxyamino or carbonyl group that is complementary to the carbonyl, oxyamino or hydrazino group of the modified oligonucleotide of formula (II) for formation of hydrazone or oxime linkages are provided. Fluorophore precursors and chromophore precursors are compounds that react with the hydrazino, oxyamino or carbonyl group of the modified oligonucleotide to form a fluorogenic or chromogenic group for analysis.

As will be appreciated by those of skill in the art, oligonucleotide-enzyme conjugates will find particular use in molecular addressing and known diagnostic assays.

Reaction of a modified oligonucleotide of formula (II), (IX) or (XI) with an appropriately modified second component provides a hydrazone or oxime linked conjugate. Thus, in one embodiment, a hydrazino modified oligonucleotide of formula (II), (IX) or (XI) reacts with a carbonyl containing second component, or a second component modified to possess a carbonyl group, such as an aldehyde or a ketone, to afford the conjugate provided herein. In another embodiment, a carbonyl modified oligonucleotide of formula (II), (IX) or (XI) is reacted with a second component containing a hydrazino group, or modified to contain a hydrazino group, to afford the conjugate provided herein. In other embodiments, the modified oligonucleotide possesses an oxyamino or carbonyl group, and the second component possesses a complementary carbonyl or oxyamino group, or is modified to possess a complementary carbonyl or oxyamino group, to afford an oxime linked conjugate.

Importantly, in certain embodiments, the reaction to form the oligonucleotide conjugate can be performed under aqueous conditions without the need for additional reagents, such as a reducing agent.

Kaneko et al. ((1991) *Bioconj. Chem.* 2:133) describes the preparation of pyridyldisulfide-substituted hydrazone derived crosslinkers in their study to identify acid-labile bonds for crosslinking of adriamycin to monoclonal antibodies, and release of the adriamycin following localization and internalization of the drug/protein conjugate. The hydrazones formed from aliphatic hydrazides were the optimal bond for this purpose as this hydrazone was stable at neutral pH but hydrolyzed at the acidic pH (4.5) in the endosome. In testing various hydrazine ($NHNH_2$) derivatives, it was found that hydrazones formed from aromatic hydrazines, aliphatic semicarbazides and aliphatic thiosemicarbazides (see, FIG.

1) are unsuitable for these purposes since the hydrazones were completely stable over the pH range 4.5-7.5.

Schwartz et al. (U.S. Pat. Nos. 5,206,370, 5,420,285 and 5,753,520, and European Patent Specification No. EP 0 384 769 B1) describe the synthesis and protein-modifying properties of a series of aromatic hydrazides, hydrazines and thiosemicarbazides. The hydrazine and thiosemicarbazide-modified conjugates are used to bind metals, e.g., technetium and rhenium, to macromolecules for use in diagnosis and treatment of diseases (see, also, Abrams et al. ((1990) *J. Nucl. Med.* 31:2022) and Schwartz et al. ((1991) *Bioconj. Chem.* 2:333). The construction or application of these bifunctional crosslinking reagents to modification of oligonucleotides for immobilization to solid surfaces nor conjugation of oligonucleotides with biopolymers, polymers or other compounds of biological interest is not described.

C. Hydrazino, Oxyamino and Carbonyl Modified Surfaces and Second Components

Provided herein are reagents and methods for modification of solid surfaces and second components for use in the methods provided herein. In particular, the modified solid surfaces and second components are useful for the immobilization of the oligonucleotide first components provided herein, and in the conjugation of such first components, respectively.

It is to be understood that the reagents described below are interchangeable in certain applications. For example, a dihydrazine reagent for modification of oligosaccharides also can be used in the modification of solid surfaces to provide a hydrazino solid surface. Many of the other reagents provided below can be used in the preparation of either modified solid surfaces or in the modification of second components for conjugation with the modified oligonucleotides provided herein.

1. Modified Surfaces

Hydrazino, oxyamino and carbonyl modified surfaces are provided. The surfaces provided herein include, but are not limited to, glasses including glasses including controlled pore glass, plastics including polyethylenes, polycarbonates, polypropylenes, polyamides such as Nylon® and polyacrylamides, and polyvinyldenedifluorides, latexes, rubbers, celluloses including nitrocelluloses and diazatized celluloses, latexes, metals including platinum, nickel, zinc, tin, palladium, steel, gold, silver, aluminum, silicon and copper, silicas, agaroses including Sephadex®, dextrans including Sepharose®, natural sponges, polystyrenes including polystyrene crosslinked with divinylbenzene, polystyrenes radiation grafted onto perfluorinated polymers such as Teflon® see, e.g., Maeji et al. (1994) *Reactive Polymers* 22:203-212; and Berg et al. (1989) *J. Am. Chem. Soc.* 111:8024-8026), oxides of metals and metalloids such as Pt—PtO, Si—SiO, Au—AuO, $TiO_2$, Cu—CuO, and the like, and compound semiconductors, such as lithium niobate, gallium arsenide and indium-phosphide. Other solid surfaces for use herein are well known to those of skill in the art. See, e.g., U.S. Pat. Nos. 4,507,230, 4,006,117, 5,389,449, 5,556,752, 4,683,202 and 5,744,305; International Patent Application Publication Nos. WO 00/04382, WO 00/04390 and WO 00/04389; Merrifield (1964) *Biochemistry* 3:1385-1390; Berg et al. (1990) in *Innovation Perspect. Solid Phase Synth. Collect. Pap.*, Int. Symp., 1st, Epton, Roger (Ed), pp. 453-459; Berg et al. (1989) in *Pept. Proc. Eur. Pept. Symp.*, 20th, Jung, G. et al. (Eds), pp. 196-198; Berg et al. (1989) *J. Am. Chem. Soc.* 111:8024-8026; Kent et al. (1979) *Isr. J. Chem.* 17:243-247; Kent et al. (1978) *J. Org. Chem.* 43:2845-2852; Mitchell et al. (1976) *Tetrahedron Lett.* 42:3795-3798; and Hermanson et al. (1992) *Immobilized Affinity Ligand Techniques*, Academic Press, Inc., San Diego.

Synthetic solid surfaces include those made from polymers and co-polymers such as polyvinylalcohols, acrylates and acrylic acids such as polyethylene-co-acrylic acid, polyethylene-co-methacrylic acid, polyethylene-co-ethylacrylate, polyethylene-co-methyl acrylate, polypropylene-co-acrylic acid, polypropylene-co-methyl-acrylic acid, polypropylene-co-ethylacrylate, polypropylene-co-methyl acrylate, polyethylene-co-vinyl acetate, polypropylene-co-vinyl acetate, and those containing acid anhydride groups such as polyethylene-co-maleic anhydride, polypropylene-co-maleic anhydride and the like. Liposomes also have been used as solid surfaces for affinity purifications (see, e.g., Powell et al. (1989) *Biotechnol. Bioeng.* 33:173).

For example, U.S. Pat. No. 5,403,750, describes the preparation of polyurethane-based polymers. U.S. Pat. No. 4,241,537 describes a plant growth medium containing a hydrophilic polyurethane gel composition prepared from chain-extended polyols; random copolymerization is preferred with up to 50% propylene oxide units so that the prepolymer will be a liquid at room temperature. U.S. Pat. No. 3,939,123 describes lightly crosslinked polyurethane polymers of isocyanate terminated prepolymers comprised of poly(ethyleneoxy)glycols with up to 35% of a poly(propyleneoxy)glycol or a poly(butyleneoxy)glycol. In producing these polymers, an organic polyamine is used as a crosslinking agent. Other solid surfaces and preparation thereof are described in U.S. Pat. Nos. 4,177,038, 4,175,183, 4,439,585, 4,485,227, 4,569,981, 5,092,992, 5,334,640, and 5,328,603.

U.S. Pat. No. 4,162,355 describes a polymer suitable for use in affinity chromatography, which is a polymer of an aminimide and a vinyl compound having at least one pendant halo-methyl group. An amine ligand, which affords sites for binding in affinity chromatography is coupled to the polymer by reaction with a portion of the pendant halo-methyl groups and the remainder of the pendant halo-methyl groups are reacted with an amine containing a pendant hydrophilic group. A method of coating a substrate with this polymer is also described. An exemplary aminimide is 1,1-dimethyl-1-(2-hydroxyoctyl)amine methacrylimide and vinyl compound is a chloromethyl styrene.

U.S. Pat. No. 4,171,412 describes specific matrices based on hydrophilic polymeric gels, preferably of a macroporous character, which carry covalently bonded D-aminoacids or peptides which contain D-aminoacid units. The basic carrier is prepared by copolymerization of hydroxyalkyl esters or hydroxyalkylamides of acrylic and methacrylic acid with crosslinking acrylate or methacrylate comonomers are modified by the reaction with diamines, aminoacids or dicarboxylic acids and the resulting carboxyterminal or aminoterminal groups are condensed with D-analogs of aminoacids or peptides. The peptide containing D-aminoacids also can be synthesized stepwise on the surface of the carrier.

U.S. Pat. No. 4,178,439 describes a cationic ion exchanger and a method for preparation thereof. U.S. Pat. No. 4,180,524 describes chemical syntheses on a silica support.

The solid supports can be identifiable or addressable, including electronic tags, such as by including encodable or pre-encoded electronic tags or bar codes in or on or associate with the supports (see, e.g., U.S. Pat. No. 6,025,129; U.S. Pat. No. 6,017,496; U.S. Pat. No. 5,972,639; U.S. Pat. No. 5,961,923; U.S. Pat. No. 5,925,562; U.S. Pat. No. 5,874,214; U.S. Pat. No. 5,751,629; U.S. Pat. No. 5,741,462), or chemical tags (see, U.S. Pat. No. 5,432,018; U.S. Pat. No. 5,547,839), or as arrays or other such addressing methods. Electronic tags include radio-frequency tags, such as IRORI MICRO-KANS® and MICROTUBES® microreactors (see, U.S. Pat. No. 6,025,129; U.S. Pat. No. 6,017,496; U.S. Pat. No. 5,972,639; U.S. Pat. No. 5,961,923; U.S. Pat. No. 5,925,562; U.S. Pat. No. 5,874,214; U.S. Pat. No. 5,751,629; U.S. Pat. No. 5,741,462; International PCT application No. WO98/31732; International PCT application No. WO98/15825; and, see, also U.S. Pat. No. 6,087,186).

Immobilized Artificial Membranes (IAMs; see, e.g., U.S. Pat. Nos. 4,931,498 and 4,927,879) also can be used. IAMs mimic cell membrane environments and can be used to bind molecules that preferentially associate with cell membranes (see, e.g., Pidgeon et al. (1990) *Enzyme Microb. Technol.* 12:149).

The solid surfaces can take the form of beads, capillaries, flat supports such as glass fiber filters, multiwell plates, thin films, membranes, wafers, combs, pins, beads in pits of flat surfaces such as wafers (e.g., silicon wafers), with or without filter plates, pellets, disks, continuous surfaces such as a microtiter dish or well, hollow fibers, needles, solid fibers, slides, chips, sheets, containers or meshes. The solid surfaces can be formed in arrays for combinatorial synthesis or analysis, or for formation of a combinatorial library. Other supports for use herein include papers coated with functionalized or functionalizable matrix materials.

The solid surface is modified to possess a hydrazino, oxyamino, or carbonyl group that is complementary to the hydrazino, oxyamino or carbonyl moiety of the oligonucleotide of formula (II) for formation of a hydrazone or oxime linkage.

The hydrazino or oxyamino modified surfaces are prepared from commercially available or known solid supports such as those described above, or incorporated into monomers for direct modification of surfaces, e.g., trialkoxysilane or monomers for inclusion in polymers or copolymers. Reaction of the support with, e.g., 5-succinimidyloxycarbonylpyrid-2yl acetone hydrazone having the formula:

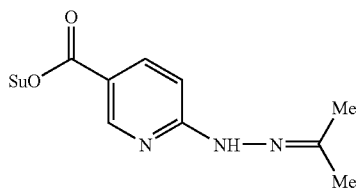

or the corresponding oxyamino compound having the formula:

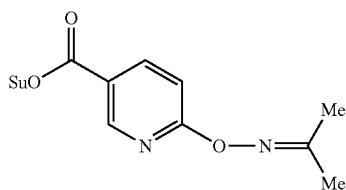

forms a hydrazone or oxime modified solid surface. Alternatively, the hydrazone or oxime succinimidyl esters shown above are reacted with an amino-substituted silane, such as 3-aminopropyltriethoxysilane, to form a silyl hydrazone or oxime. Reaction of the silyl group with a solid surface forms a hydrazone or oxime modified solid surface. Hydrolysis of the hydrazone or oxime group under mild acidic conditions (e.g., 0.1 M acetate, pH 4.7) affords the hydrazino or oxyamino modified surfaces provided herein. See, co-pending, co-owned U.S. provisional application Ser. No. 60/191,186, the disclosure of which is incorporated herein by reference in its entirety.

In one embodiment, hydrazino modified gold surfaces are prepared by reaction with a dihydrazino-dithiol compound of formula X-M-S—S-M-X, where each S is sulfur, each X is independently a protected or unprotected hydrazino group, and each M is independently selected as above. In preferred embodiments, the compound is symmetrical and has the formula $(X-M-S—)_2$. In these embodiments, M preferably has any combination, preferably 1 to 100, more preferably 1 to 50, most preferably 1 to 10, of the following groups: arylene, heteroarylene, C(E), N($R^1$) and C($R^1$)$_2$, where E and $R^1$ are selected as above, which groups can be combined in any order. $R^1$ is preferably hydrogen and E is preferably oxygen. In more preferred embodiments, M has 1 to 10 of the following groups: pyridylene, NH, C(O) and CH$_2$, which groups can be combined in any order. M is most preferably derived from cysteamine. Briefly, reaction of cysteamine dimer (i.e., $(H_2NCH_2CH_2S)_2$) with succinimidyl 2-BOC-hydrazino-5-pyridylcarboxylate provides, after deprotection, the dihydrazino-dithiol:

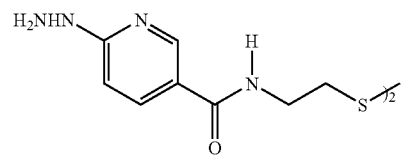

Reaction of this dithiol with a gold surface results in cleavage of the dithiol bond to form a hydrazino modified gold surface (i.e., Au—S—CH$_2$CH$_2$—NHC(O)-pyr-NHNH$_2$).

Carbonyl modified surfaces are prepared from commercially available solid supports such as those described above. Reaction of the support with, e q, succinimidyl 4-formylbenzoate or 4'-succinimidyloxycarbonylacetophenone forms a carbonyl, particularly an aldehyde or methyl ketone modified solid surface. Alternatively, succinimidyl 4-formyl benzoate or 4'-succinimidyloxycarbonylacetophenone is reacted with an amino-substituted silane, such as 3-aminopropyltriethoxysilane, to form a silyl aldehyde or ketone. Reaction of the silyl group with a solid surface forms an aldehyde or ketone modified solid surface.

2. Modified Second Components

Hydrazino, oxyamino, and carbonyl modified second components can be prepared by methods provided herein, or by methods well known to those of skill in the art.

For example, an oligosaccharide can be reacted with cyanogen bromide or 1-cyano-4-dimethylaminopyridinium bromide (CDAP) to afford a cyano ether of formula R—O—CN. Reaction of this cyano ether with a hydrazino, oxyamino or carbonyl substituted amine, provided herein, affords a hydrazino, oxyamino or carbonyl substituted oligosaccharide, where the hydrazino, oxyamino or carbonyl group is linked to the oligosaccharide through a group of formula —O—C(=NH)—NH—.

In one embodiment, the hydrazino, oxyamino or carbonyl substituted amine provided herein for oligosaccharide modification has the formula:

H$_2$N-M-X, or a derivative thereof, where M and X are selected as above. In certain embodiments, the compound of formula $H_2N$-M-X is selected where M is not $C_{1-12}$alkyl.

In the above embodiments, the modified oligosaccharide has the formula:

$O^3$—O—C(=NH)—NH-M-X, where $O^3$ is an oligosaccharide; and M and X are as defined above.

Figure 12:
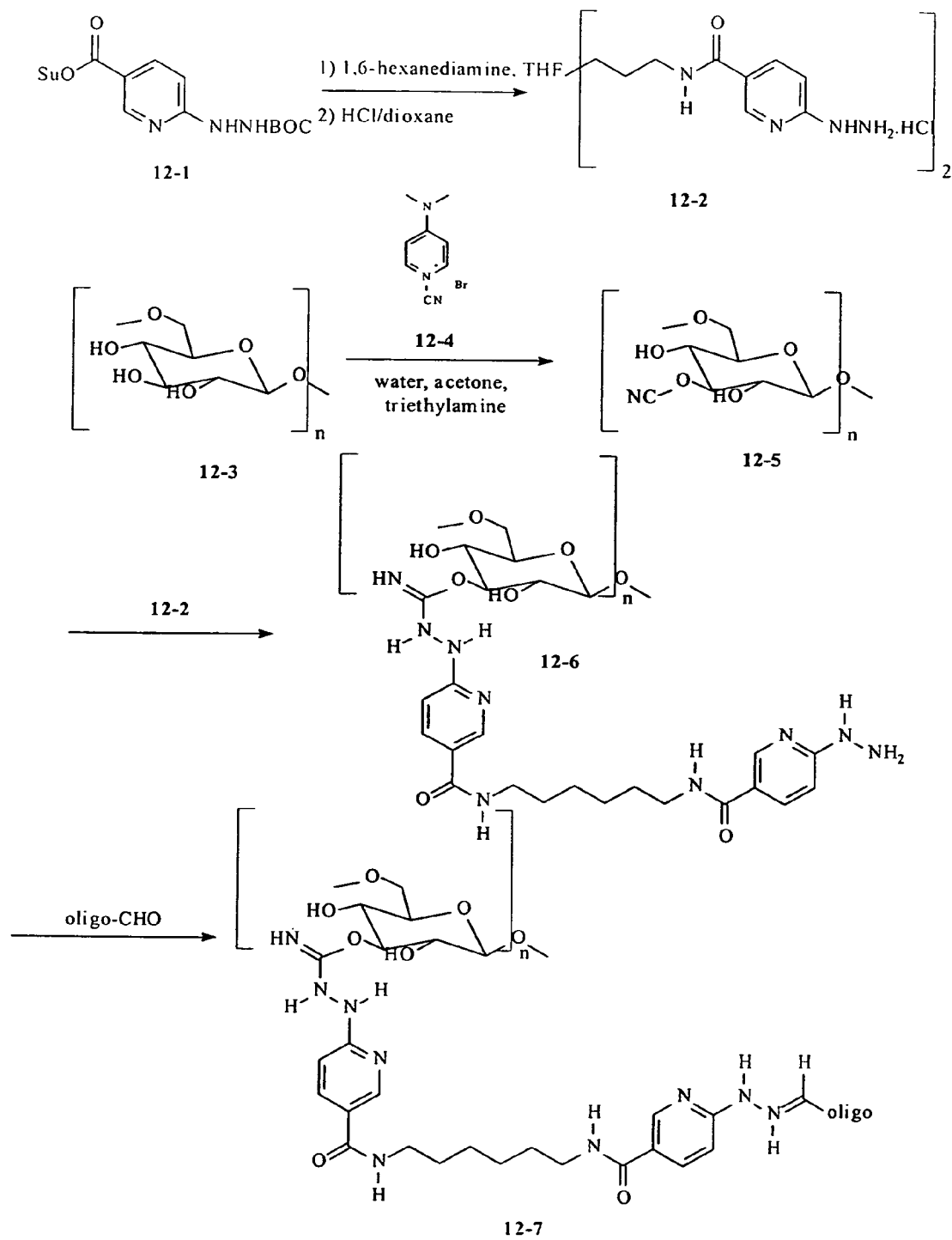
FIG. 12 shows the modification of an oligosaccharide to incorporate a hydrazino group for conjugation to an aldehyde modified oligonucleotide.

Alternatively, oligosaccharides are derivatized as their hydrazino analogs by reaction with CDAP and a dihydrazino compound (see, e.g., FIG. 12). The dihydrazino compounds have the formula:

X-M-X, or a derivative thereof, where each X is independently a hydrazino group and M is selected as above. In preferred embodiments, M has any combination, preferably 1 to 100, more preferably 1 to 50, most preferably 1 to 10, of the following groups: arylene, heteroarylene, $C(R^1)_2$, $N(R^1)$ and C(E), where $R^1$ and E are selected as above, which groups can be combined in any order. In preferred embodiments, $R^1$ is hydrogen and E is oxygen. In more preferred embodiments, M has 1 to 10 of the following groups: heteroarylene, $CH_2$, NH and C(O), which groups can be combined in any order. M most preferably is derived, in these embodiments, from reaction of 1,6-hexanediamine with two equivalents of succinimidyl N'-BOC-6-hydrazinonicotinate (see, FIG. 12). Thus, the reagent of formula X-M-X most preferably has formula:

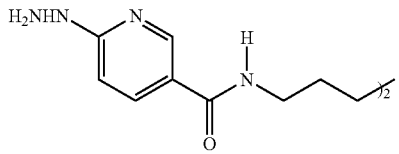

The resulting hydrazino modified oligosaccharide is then conjugated to a carbonyl modified oligonucleotide provided herein. Similarly, di(oxyamino) compounds of formula X-M-X, or a derivative thereof, where X is an oxyamino group and M is selected as above, can be used to generate oxyamino modified oligosaccharides for conjugation with carbonyl modified oligonucleotides.

Polysaccharides or glycoproteins can be oxidized with sodium periodate to yield aldehyde groups directly. These aldehyde groups can be directly labeled with hydrazine modified oligonucleotides as described herein. Lysine moieties on proteins can be modified to incorporate aldehydes using succinimidyl 4-formylbenzoate (Pierce Chemical Co.). These aldehyde containing proteins can be directly conjugated to hydrazine modified oligonucleotides.

Hydrazine groups also can be incorporated on insoluble polysaccharides such as cellulose or agarose using 1-cyano-4-dimethylaminopyridine bromide (CDAP) as described by Lees et al. ((1996) Vaccine 14:190 and (2000) Vaccine 18:1273) using a dihydrazine molecule (see, e.g., Example 16).

Modified proteins possessing hydrazino or oxyamino groups can be prepared by the methods described in U.S. Pat. Nos. 5,206,370, 5,420,285 and 5,753,520, and European Patent Specification EP 0 384 769 B1, the disclosures of which are incorporated herein by reference in their entirety. These hydrazine modified proteins can be directly conjugated to aldehyde modified oligonucleotides prepared as described herein. Carbonyl modified proteins are prepared by reaction of an aldehyde or ketone substituted succinimidyl ester with nucleophilic groups of the protein, including, but not limited to, the amino side chain of lysine. In certain embodiments, the aldehyde or ketone substituted N-hydroxysuccinic ester is, for example, succinimidyl 4-formyl- or 4-acetylbenzoate. In other embodiments, the protein is reacted with succinimidyl levulinate (succinimidyl 4-oxopentanoate) to provide a ketone substituted protein.

Methods of synthesis of hydrazino, oxyamino, and carbonyl modified oligonucleotides are provided herein.

In other embodiments herein, particularly when the modified oligonucleotide possesses a hydrazino or oxyamino group, the second component can possess an epoxide, α-bromocarbonyl, maleimide, maleic anhydride, isothiocyanate or isocyanate group. Such second components can be prepared by methods provided herein or other methods well known to those of skill in the art. For example, reaction of pentafluorophenyl 4-isothiocyanatobenzoate with an amino or hydroxy group of a second component results in formation of an isothiocyanato modified solid surface. Reaction of the hydrazino or oxyamino group of the modified oligonucleotide with the epoxide, α-bromocarbonyl, maleimide, maleic anhydride, isothiocyanate or isocyanate group of the second component results in covalent attachment of the oligonucleotide to the second component. In these embodiments, conjugation of the hydrazino modified oligonucleotide can be conducted at a lower pH that for the corresponding amino modified oligonucleotide.

D. Methods of Use of Modified Oligonucleotides

The hydrazino, oxyamino and carbonyl modified oligonucleotides or formula (II) provided herein are useful in a variety of methods, including, but not limited to, diagnostic probe assays, DNA amplification by solid phase polymerase chain reactions (PCR), molecular computing (see, e.g., Adleman (1994) Science 266:1021-1024; Kari (1997) Mathematical Intelligencer 19:9-22; Frutos et al. (1997) Nucleic Acids Res. 25:4748; Smith et al. (1998) J. Comp. Biol. 5:255; Liu et al. (1998) J. Comp. Biol. 5:267; Frutos et al. (1998) J. Am. Chem. Soc. 120:10277; Wang et al. (1999) Biosystems 52:189-191; Liu et al. (1999) Biosystems 52:25-33; Liu et al. (2000) Nature 403:175-179; European Patent Application Publication No. EP 0 772 135; Reed et al. (June 2000) Scientific American: 86-93), molecular addressing (Niemeyer et al. (1994) Nucl. Acids Res. 22(25):5530-5539), DNA sequencing by mass spectrometry (see, e.g., U.S. Pat. Nos. 6,074,823 and 5,547,835) and in studying the molecular electronics of DNA (see, e.g., U.S. Pat. Nos. 6,071,699, 6,066, 448, 5,952,172 and 5,824,473). In general, the modified oligonucleotide is immobilized as described herein for use in the above methods.

The hydrazino modified oligonucleotides prepared using the reagents of formula (I) are also useful for a variety of additional purposes, including, but not limited to:

(i) direct attachment to surfaces such as carbonyl, i.e., aldehyde or ketone, modified surfaces, as described herein; resulting in oligonucleotides attached via a hydrazone bond formed between the 5'-substituted hydrazino oligonucleotide and the carbonyl moiety on the surface; and (ii) direct attachment to any biopolymer which has been modified to include a carbonyl moiety using, for example, periodate oxidation of carbohydrates or functionalization of amino moieties using carbonyl modification reagents such as succinimidyl 4-formyl benzoate. See, e.g., Ghosh (European Patent Application Publication No. Ep 0 361 768), the disclosure of which is incorporated herein in its entirety.

In the cases wherein the final hydrazino product is required directly from standard aqueous ammonia deprotection and cleavage from the solid support, the hydrazino protecting group is a labile protecting group, including, but not limited to, FMOC, benzoyl or acetyl, that is removed during deprotection of the other oligonucleotide protecting groups. Thus direct addition of the crude reaction product to a solid surface appropriately modified with a moiety that reacts with the hydrazino function will lead to covalent modification of the surface, and non-hydrazino modified oligonucleotides and other impurities will be washed away.

E. Preparation of the Reagents

In general, the reagents of formula (I) provided herein can be prepared by methods well known to those of skill in the art, or by modification of those methods using techniques known to those of skill in the art.

For example, reagents of formula (I) where X is a carbonyl group, particularly an aldehyde or ketone group, can be prepared starting from formyl- or keto-substituted carboxylic acids and carboxylic acid derivatives. Many such formyl- or keto-substituted carboxylic acids and carboxylic acid derivatives, including 4-formylbenzoic acid and 4'-carboxyacetophenone are commercially available (see, e.g., Aldrich Chemical Co., Milwaukee, Wis.). Reaction of the succinimidyl ester or other activated ester of these carboxylic acids, prepared, e.g., from the carboxylic acid, N-hydroxysuccinimide and dicyclohexylcarbodiimide, with, e.g., an α,ω-aminoalcohol such as 6-aminohexanol, provides a formyl- or keto-substituted-ω-hydroxyamide. Derivatization of the hydroxy group of this amide as the corresponding phosphorous based coupling group, e.g., a phosphoramidite, can be achieved under standard conditions well known to those of skill in the art. For example, reaction of the alcohol with diisopropyl pyrrolidinyl phosphoryl chloride in the presence of triethylamine provides the desired N,N-diisopropylchlorophosphoramidite. Alternatively, reaction of the alcohol with 2-cyanoethyl-N,N,N',N'-tetraisopropylphosphorodiamidite in the presence of diisopropylammonium tetrazolide affords the 2-cyanoethyl-N,N-diisopropylphorphoramides provided herein.

In another example, the reagents of formula (I) where X is a hydrazino group or oxyamino group are prepared starting from hydrazino- or oxyamino-substituted carboxylic acids and carboxylic acid derivatives. Such hydrazino or oxyamino compounds are prepared by reaction of the corresponding halocarboxylic acid with, e.g., hydrazine, hydroxylamine, or derivatives thereof. Semicarbazides and thiosemicarbazides are prepared by reaction of hydrazine with the corresponding isocyanates and isothiocyanates. Carbazides and thiocarbazides can be prepared by reaction of a hydrazine derivative with phosgene or thiophosgene, or an equivalent thereof, and hydrazine. Hydrazides are prepared by reaction of an activated carboxylic acid with hydrazine. A carbonic acid dihydrazine is prepared by reaction of an isocyanate with carbonic acid dihydrazide. A hydrazine carboxylate can be prepared by reaction of an alcohol with phosgene and hydrazine.

The resulting hydrazino or oxyamino carboxylic acid is then protected. The protecting group is a salt or is any amine or hydrazine protecting group known to those of skill in the art.

Reaction of the succinimidyl ester or other activated ester of protected hydrazino or protected oxyamino carboxylic acids, prepared, e.g., from the carboxylic acid, N-hydroxysuccinimide and dicyclohexylcarbodiimide, with, e.g., an α,ω-aminoalcohol such as 6-aminohexanol, provides a formyl- or keto-substituted-ω-hydroxyamide. Derivatization of the hydroxy group of this amide as the corresponding phosphorous based coupling group, e.g., a phosphoramidite, can be achieved under standard conditions well known to those of skill in the art. For example, reaction of the alcohol with diisopropyl phosphoryl dichloride in the presence of triethylamine provides the desired N,N-diisopropylchlorophosphoramidite, whereas reaction of the alcohol with N,N-diisopropyl-O-(2-cyanoethyl)phophoramidyl chloride provides the desired N,N-diisopropyl-O-(2-cyanoethyl) phosphoramidate.

The following examples are included for illustrative purposes only and are not intended to limit the scope of the invention.

EXAMPLE 1

Preparation of an Aldehyde Phosphoramidite

Figure 3:
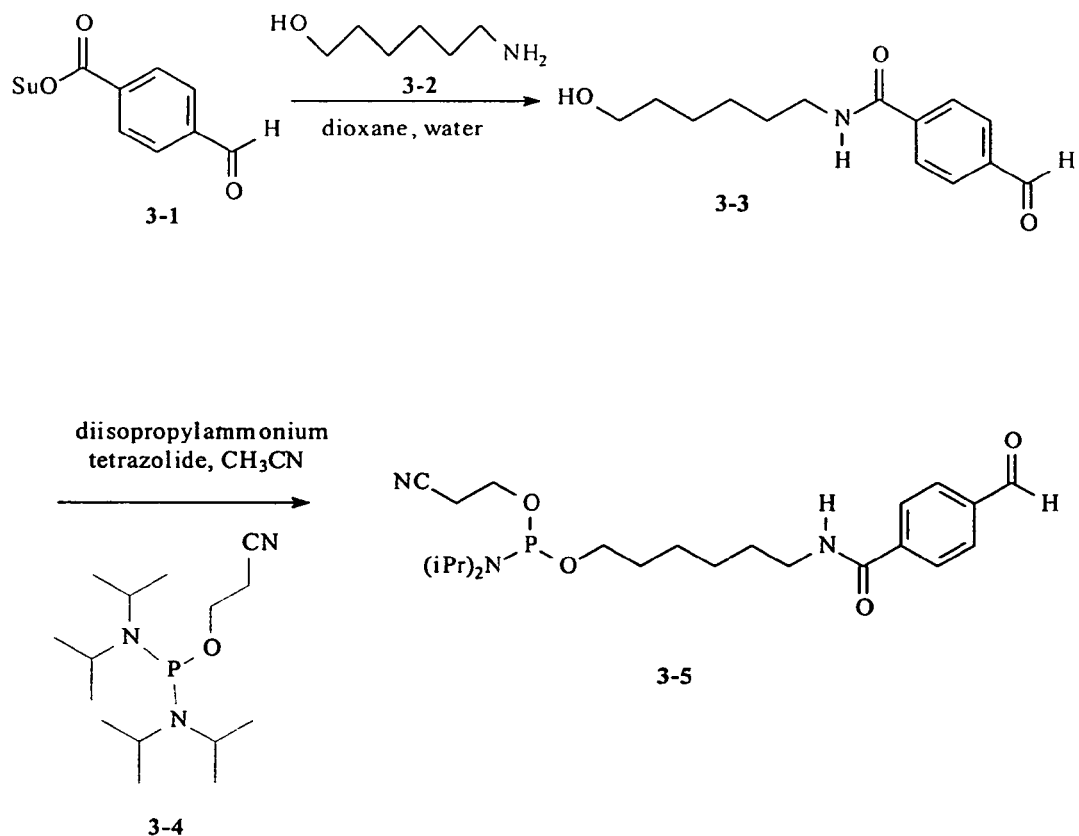
FIG. 3 shows the synthesis of a carbonyl (aldehyde) amidite monomer provided herein (see, Example 1).
Figure 4:
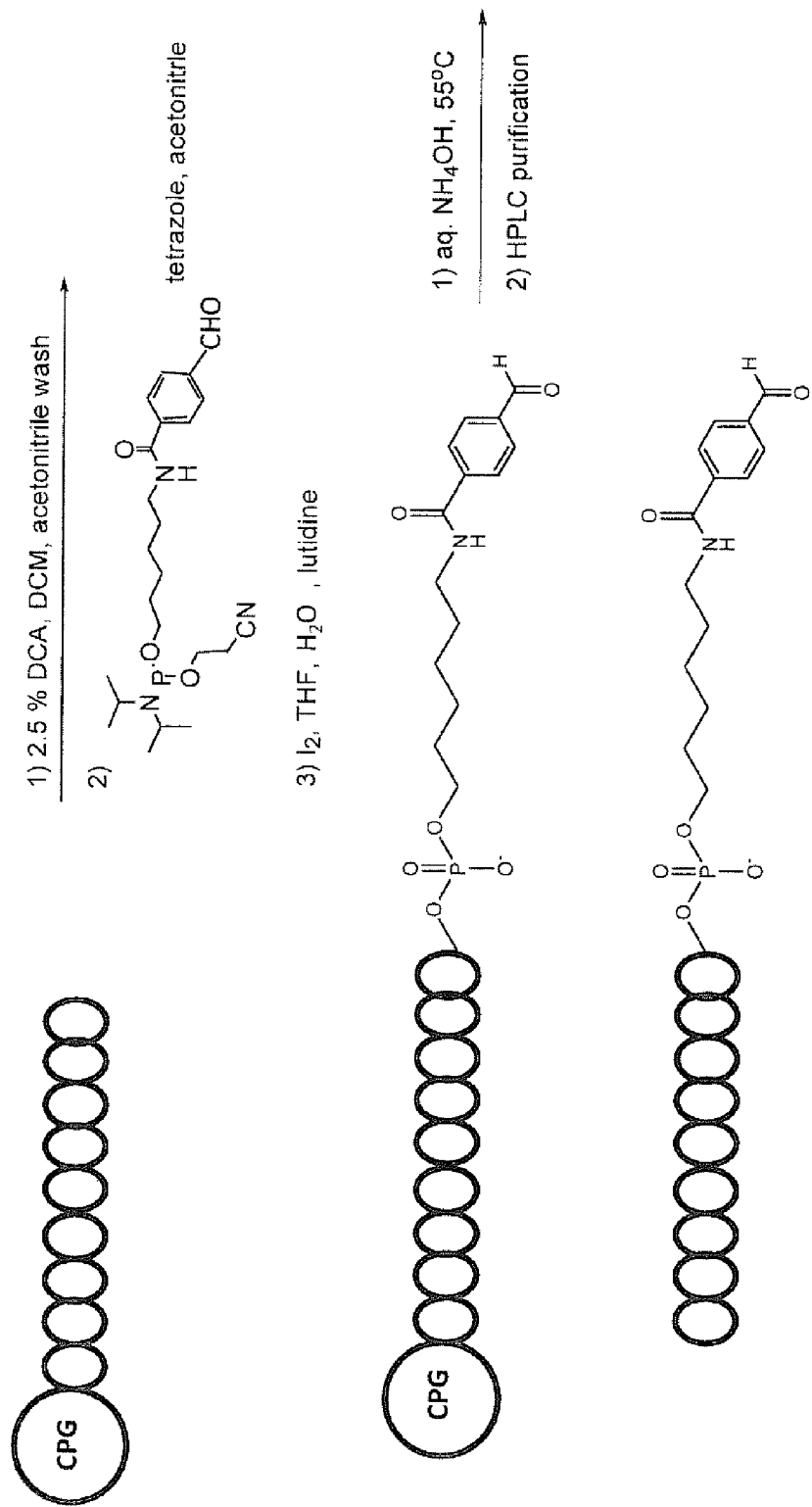
FIG. 4 illustrates incorporation of the aldehyde amidite monomer of FIG. 3 during oligonucleotide solid phase synthesis.
Figure 5:
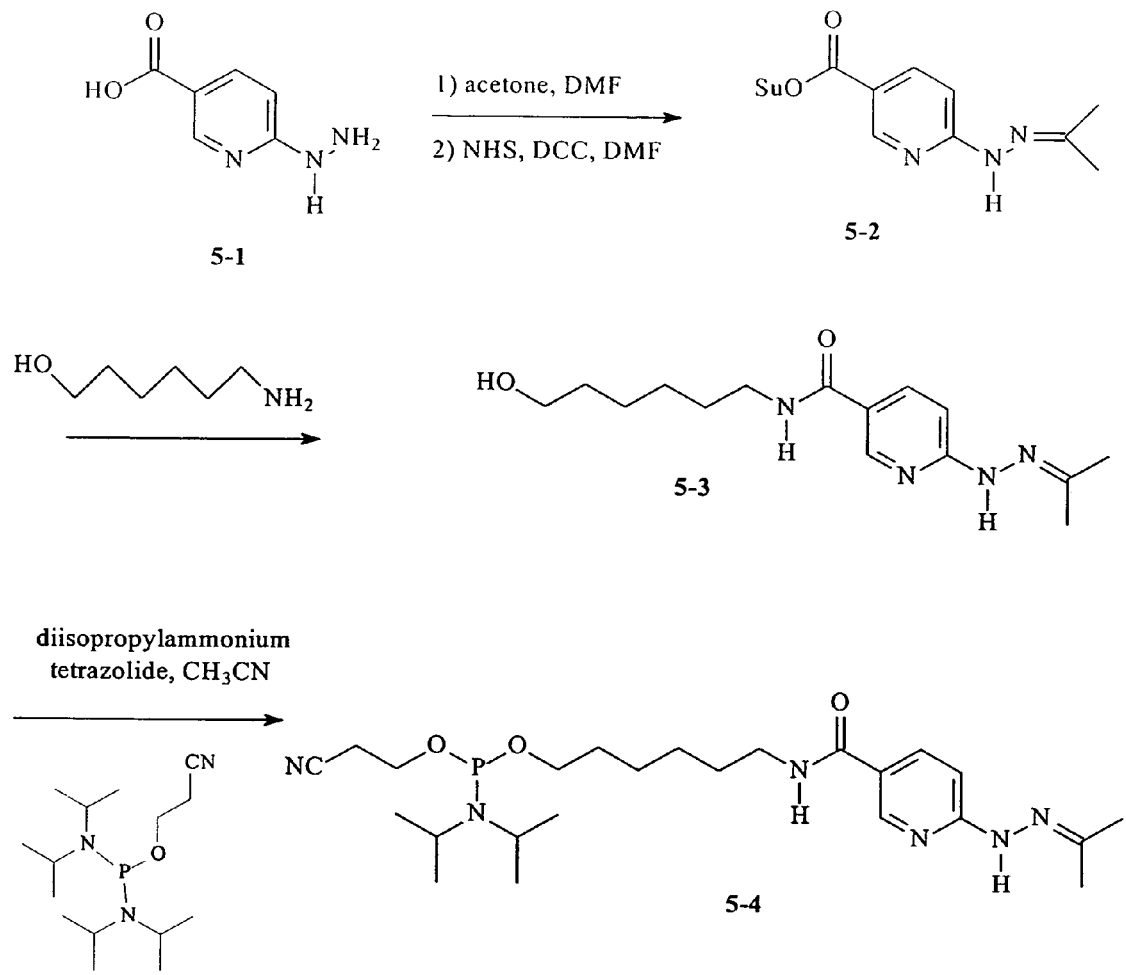
FIG. 5 illustrates the synthesis of a hydrazone phosphoramidite monomer provided herein (see, Example 3).

As shown in FIG. 3, succinimidyl 4-formylbenzoate (3-1; 6.06 g, 24.5 mmol, 1 eq.) was dissolved in dioxane (60 mL). To this, a solution of 6-aminohexanol (3-2; 3 g, 25.7 mmol, 1.05 eq.) in $H_2O$ (10 mL) was added dropwise. Thin layer chromatography indicated that the reaction is complete after 3 hours stirring at room temperature. The reaction mixture was concentrated and the residue was suspended in ethyl acetate. The product was isolated by filtration. The product was recrystallized from ethyl acetate. The mother liquor was concentrated and a second crop of produce was isolated by filtration to give a total of 3.4 grams of desired aldehyde alcohol 3-3.

Alcohol (3-3; 3.3 g, 13 mmol, 1 eq.) was evaporated from pyridine (4×20 mL) and suspended in dry $CH_2Cl_2$ (40 mL). Diisopropylammonium tetrazolide (1.1 g, 6.6 mmol, 0.5 eq.) was added to the reaction mixture neat. Amidite (3-4; 4.4 mL, 15 mmol, 1.1 eq.) was added dropwise over 10 minutes. The reaction mixture was heterogeneous with a slight yellow color. Thin layer chromatography indicated the reaction was complete after 1.5 hours (ethyl acetate/hexanes/triethylamine 6:3:1). The reaction mixture was washed with 5% $NaHCO_3$ (2×10 mL), followed by $H_2O$ (1×10 mL), and brine (1×10 mL), then dried with $Na_2SO_4$, filtered and concentrated, and the residue was purified by silica gel chromatography (14 in×2 in, ethyl acetate/hexanes/triethylamine 6/3.9/0.1). Fractions containing product were combined and concentrated. Desired amidite 3-5 was evaporated from toluene (4×40 mL) followed by acetonitrile (4×40 mL). Yield: 5.38 g.

EXAMPLE 2

Incorporation of an Aldehyde Amidite on the 5'-Terminus of Oligonucleotide During Solid Phase Synthesis A 25 mer phosphodiester DNA oligonucleotide with sequence 5' ttt-ttt-tag-cct-aac-tga-tgc-cat-g 3' was synthesized on a PerSeptive Expedite 8909 instrument using the standard protocol. A small amount of beads were removed for use as a precursor (DMT-off) standard. A 0.1 M solution of the aldehyde phosphoramidite from Example 1 was prepared by dissolving the solid in dry acetonitrile (less than 20 ppm water). The aldehyde amidite was coupled to the 5' end of the oligonucleotide by syringe using a manual syringe coupling technique. The coupling time was 15 minutes.

The modified oligonucleotide and the precursor standard were deprotected with concentrated ammonium hydroxide for 15 hours at 55° C. Following the deprotection, the ammonium hydroxide solution was transferred from the cpg and dried in a speed vac concentrator. Each crude sample was analyzed on a 15% acrylamide denaturing gel (0.5 mm wide, 30 cm long). The addition of the aldehyde linker was apparent in the gel as a slower migrating band. A small amount of unmodified oligonucleotide was present indicating that the aldehyde coupling was only about 80-85%.

The dried oligonucleotide was resuspended in water and purified on a Waters uBondapak C18 reverse phase HPLC column (10 μm, 0.8×10 cm). Buffers used were A=50 mM TEAA (pH 7.0)/2% acetonitrile and B=acetonitrile. The gradient run was 0-50% Buffer B over 30 minutes with a flow of 2.5 mL per minute. Separation of the aldehyde labeled material was not baseline but a definitive aldehyde peak was observed eluting at the back-end of the failure material peak. Several fractions (approximately 0.2 minutes) were collected across the aldehyde peak. The fractions containing the most material were analyzed by hydrazinopyridine assay (see Example 11) and confirmed that the oligonucleotide possessed an aldehyde group. Material from the peak fraction was also analyzed by ESI mass spectroscopy and confirmed to have the correct mass. Analytical HPLC of the purified product is showed a single peak.

EXAMPLE 3

Procedure for Conversion Alcohols to Amidites

To a solution of the alcohol (1 equiv.) in dry acetonitrile is added diisopropylammonium tetrazolide (2.5 equiv.) followed by the addition of 2-cyanoethyl-N,N,N',N'-tetraisopropylphosphorodiamidite (1.2 equiv.). The reaction mixture is stirred at room temperature until complete (TLC: silica gel, ethyl acetate/hexanes/triethylamine (47.5/47.5/5)). The reaction mixture is concentrated and redissolved in a minimal amount of ethyl acetate and purified by flash chromatography (silica gel). The column is packed with ethyl acetate/hexanes/triethylamine (47.5/47.5/5) and eluted with ethyl acetate/hexanes/triethylamine (49.5/49.5/1). Fractions containing the product are combined and dried to yield the desired phosphoramidite. The purity and structure of the product is confirmed by $^1$H NMR and $^{31}$P NMR.

EXAMPLE 4

Preparation of 5'-Hydrazino-Substituted Oligonucleotide

A. Preparation of an MMT-Protected Hydrazino Phosphoramidite Monomer 8-3

Figure 8:
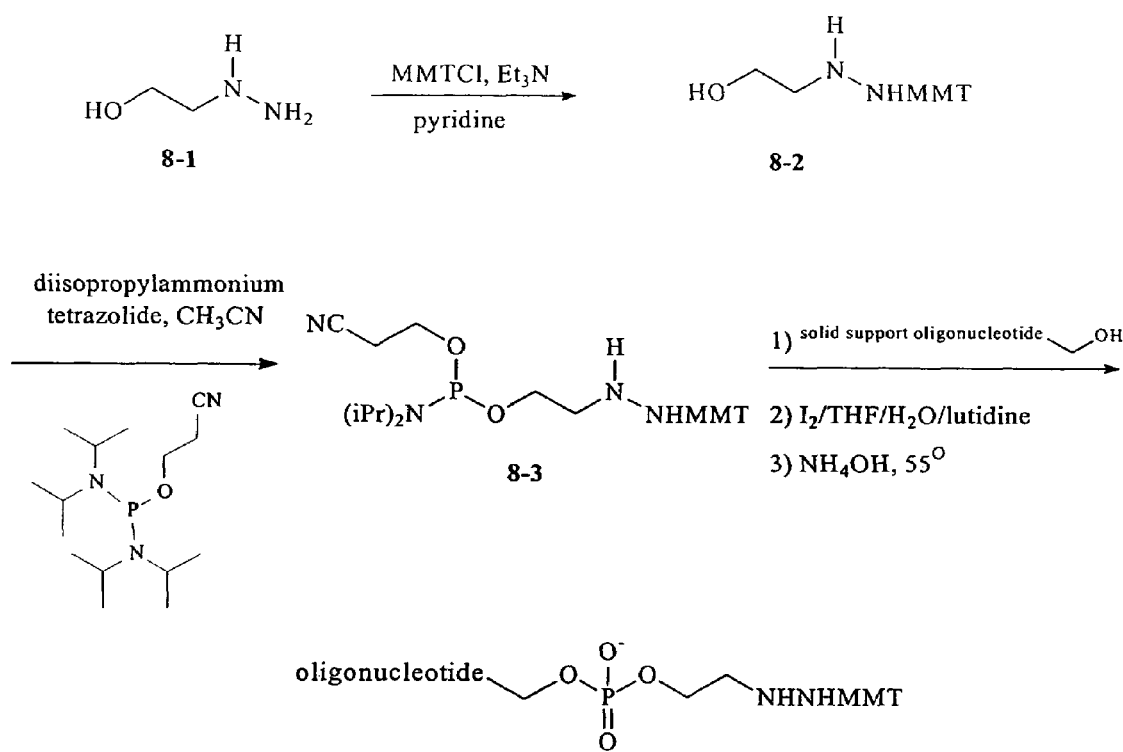
FIG. 8 shows the synthesis of an aliphatic hydrazino amidite and the incorporation thereof into an oligonucleotide using solid phase synthetic techniques.

As shown in FIG. 8, to a solution of 2-hydrazinoethanol (1 equivalent; Acros Chemical) in pyridine is added a solution of MMT-Cl (monomethoxytrityl chloride, 1.0 equivalents). The reaction mixture is stirred at room temperature until complete as analyzed by thin layer chromatography. The solvent is removed by evaporation and the residue is partitioned between ethyl acetate and 5% aqueous citric acid. The organic phase is further washed with brine, dried over magnesium sulfate, filtered and concentrated. The residue is purified by flash chromatography to give the desired alcohol 8-2.

The resulting 2-MMT-hydrazino-ethanol is converted to the corresponding amidite 8-3 using the general protocol for preparation of amidites described in Example 3.

B. Coupling of an MMT-Protected Hydrazino Phosphoramidite Monomer with an Oligonucleotide The MMT-protected hydrazino phosphoramidite monomer 8-3 from Example 4.A is then dissolved in acetonitrile and coupled to the 5' terminus of an oligonucleotide in the presence of an excess of tetrazole. The oligonucleotide is then be deprotected and cleaved from support using base, followed by purification and subsequent removal of the trityl (MMT) moiety with acid. Repurification is possible at this juncture, if required.

EXAMPLE 5

Preparation of 5'-Semicarbazido-Substituted Oligonucleotide

A. Preparation of an MMT-Protected Semicarbazido Protected Amidite

Figure 9:
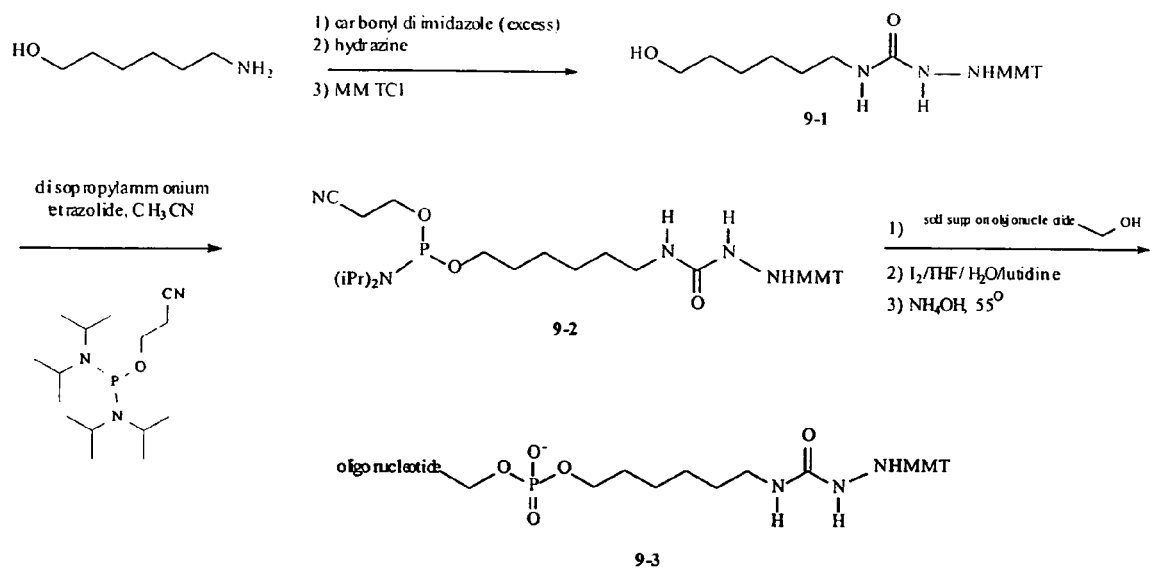
FIG. 9 shows the synthesis of an aliphatic semicarbazido amidite and the incorporation thereof into an oligonucleotide using solid phase synthetic techniques.

As shown in FIG. 9, to a solution of 6-aminohexanol (1 equivalent; Aldrich Chemical Co.) is added a solution of carbonyl diimidazole (10 equivalents; Aldrich Chemical Co.) in DMF and stirred at room temperature. The solvent is removed under vacuum and the residue is purified by flash chromatography.

To a solution of the carbonylimidazole-modified aminohexanol in dimethylformamide is added a solution of hydrazine (1 equivalent: Aldrich Chemical Co.) and the reaction is stirred at room temperature for 1 h. Subsequently a solution of MMT chloride in DMF is added and the reaction mixture stirred at room temperature until the reaction is complete as analyzed by thin layer chromatography. The solvent is removed on the rotavap under high vacuum and the product is isolated by flash chromatography to yield 9-1.

The resulting 2-MMT-protected semicarbazido-alcohol 9-1 is converted to the corresponding amidite 9-2 using the general protocol for preparation of amidites described in Example 3.

B. Coupling of MMT-Protected Semicarbazido Protected Amidite with an Oligonucleotide The reagent from Example 5.A 9-2 is then dissolved in acetonitrile and coupled to the 5' terminus of an oligonucleotide in the presence of an excess of tetrazole. The oligonucleotide is then deprotected and cleaved from support using base, followed by purification and subsequent removal of the trityl moiety with acid. Repurification would be possible at this juncture, if required.

EXAMPLE 6

Preparation of a 5'-Thiosemicarbazido-Substituted Oligonucleotide

A. Preparation of a 5'-FMOC-Thiosemicarbazido Phosphoramidite

Figure 10:
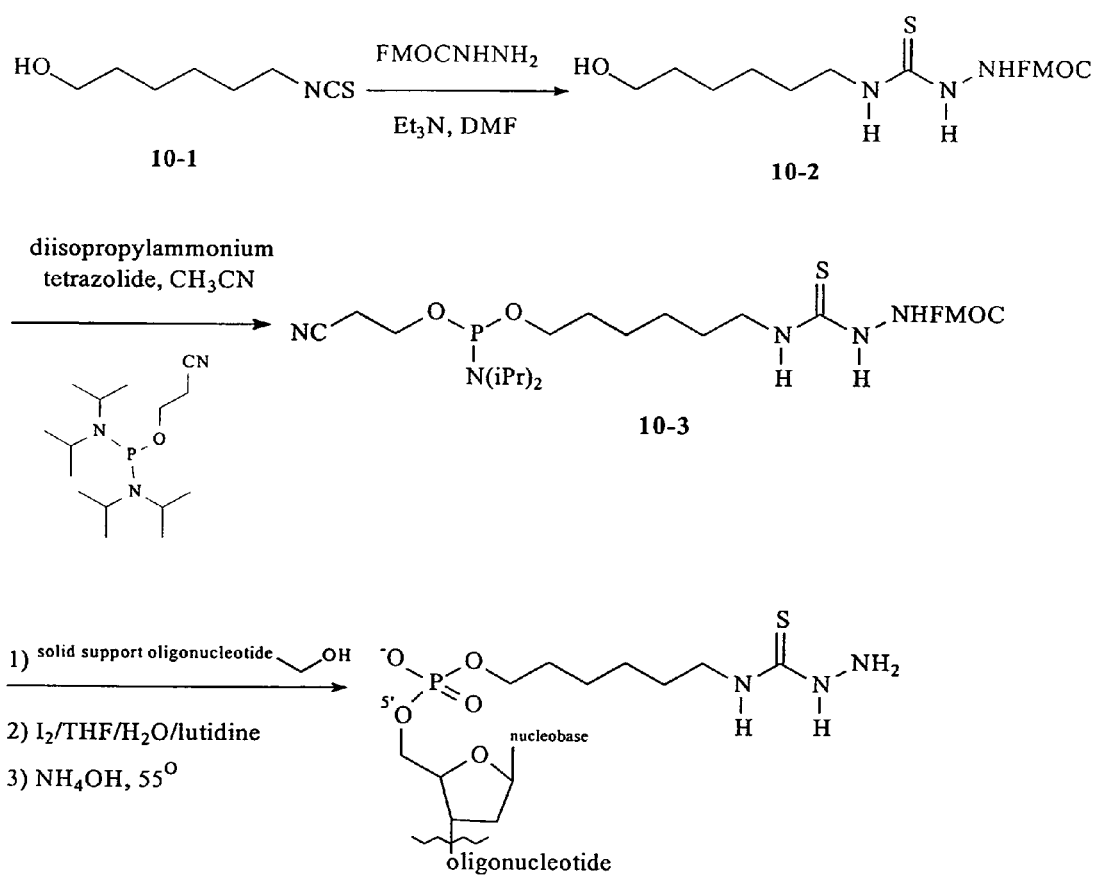
FIG. 10 shows the synthesis of an aliphatic thiosemicarbazido amidite and the incorporation thereof into an oligonucleotide using solid phase synthetic techniques.

As shown in FIG. 10, to a solution of 6-isothiocyantohexanol (10-1; prepared from 6-aminohexanol and thiophosgene according to the method of D. W. Browne and G. M. Dyson *J. Chem. Soc.* (1934) 178; Aldrich Chemical Co.) and triethylamine (1.1 equivalents) in DMF is added a solution of FMOC-hydrazine (1.0 equivalents). The reaction mixture is stirred until complete as determined by thin layer chromatography. Following removal of the solvent, the residue is partitioned between ethyl acetate and 5% citric acid. The organic phase is washed with brine, dried (magnesium sulfate), filtered and concentrated. The product is purified by flash chromatography on silica gel to yield 10-2.

The resulting FMOC-protected thiosemicarbazido-alcohol 10-2 is converted to the corresponding amidite 10-3 using the general protocol for preparation of amidites described in Example 3.

B. Coupling of 5'-FMOC-Thiosemicarbazido Phosphoramidite with an Oligonucleotide The FMOC-protected thiosemicarbazido amidite 10-3 is incorporated on the 5'-end of an oligonucleotide on the solid support using standard coupling conditions as described in Example 2 above.

EXAMPLE 7

Covalent Coupling of a 5'-Hydrazino-Substituted Oligonucleotide to a Carbonyl-Modified Polycarbonate 96 Well Plate Covalink primary amino 96 well plates (Nalgene Nunc, catalog #459439) are reacted with succinimidyl 6-hydrazinonicitinoate acetone hydrazone to immobilize lower alkyl hydrazone groups on the surface.

A 5 nM solution of a 5'-hydrazino-oligonucleotide, as prepared in Example 4, in 0.1 M acetate, pH 4.7 is prepared. The oligonucleotide solution is added to one or more wells of the above aldehyde 96 well plate. Following incubation at 25-37° C. for 2-16 h, the wells are washed with PBS/0.05% Tween® to remove unreacted oligonucleotide. The probe oligonucleotide is covalently bound to the plastic and ready for use to capture its complementary target oligonucleotide.

EXAMPLE 8

Solid Phase PCR Using an Aldehyde-Oligonucleotide Covalently Bound to the Hydrazine Modified Surface of a 96 Well Plate To a well of a carbonyl-modified 96 well plate (prepared as described in Example 7) to which a 5'-hydrazino-oligonucleotide of a length of 15-40 oligonucleotides has been covalently bound is added buffer, nucleotides, Taq polymerase, template, primer "one" and primer "two". The choice of primer "one" and primer "two" depends on the oligonucleotide being prepared and is readily ascertainable by those of skill in the art. The ratio of primer "one" to primer "two" is 1:8. Amplification is initiated. After amplification, the well is washed, thereby removing the amplicons in the liquid phase. The bound amplicons are converted to single stranded molecules by treatment with NaOH. The bound single stranded PCR product can be used for variety of purposes as described in the literature. See, e.g., Agrawal, Protocols for Oligonucleotides and Analogs, in *Methods in Molecular Biology* 20 (Humana Press, 1993).

EXAMPLE 9

Figure 17:
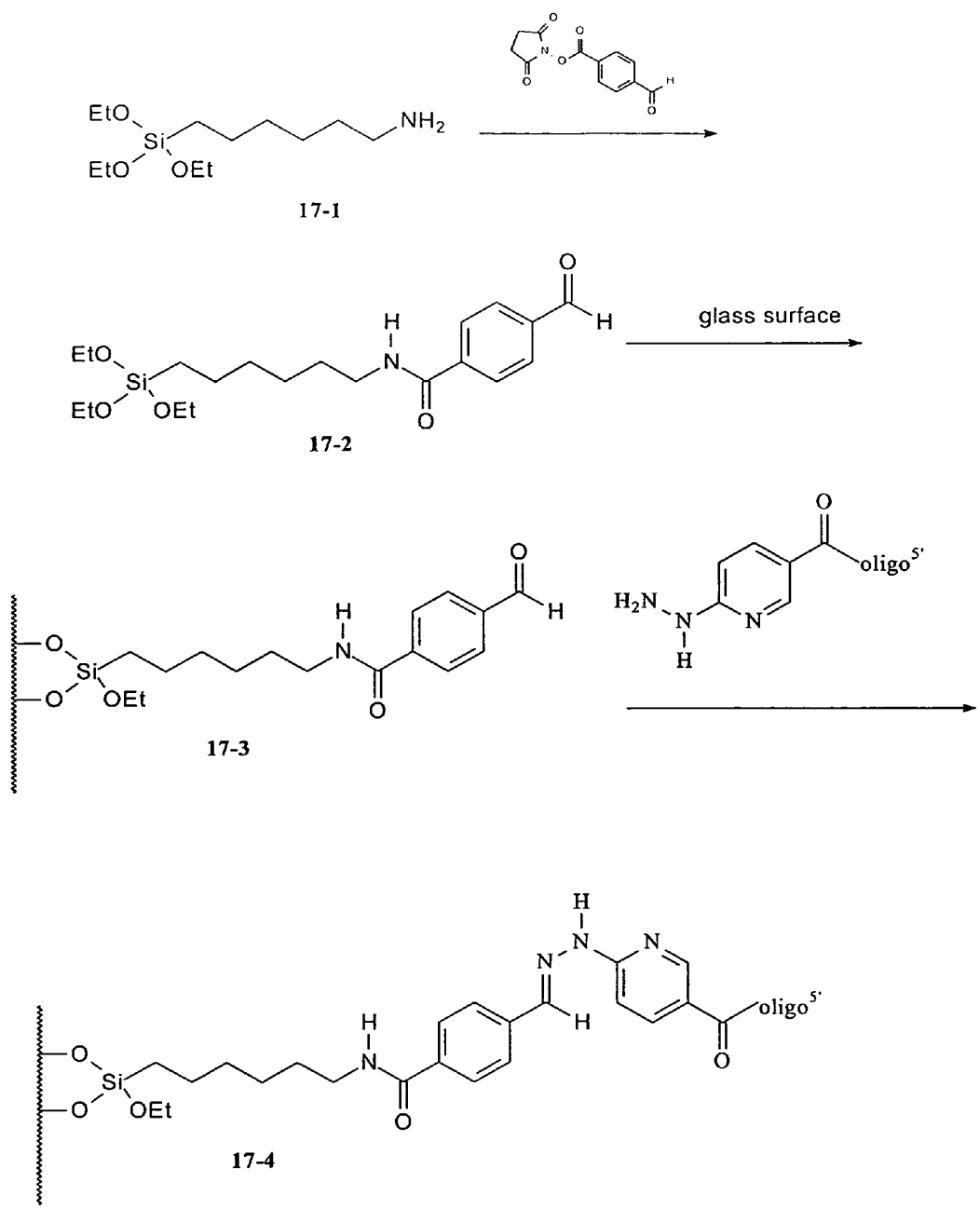
FIG. 17 illustrates the preparation of a carbonyl (e.g., aldehyde) modified solid surface and immobilization of a hydrazino modified oligonucleotide thereon.
Figure 18:
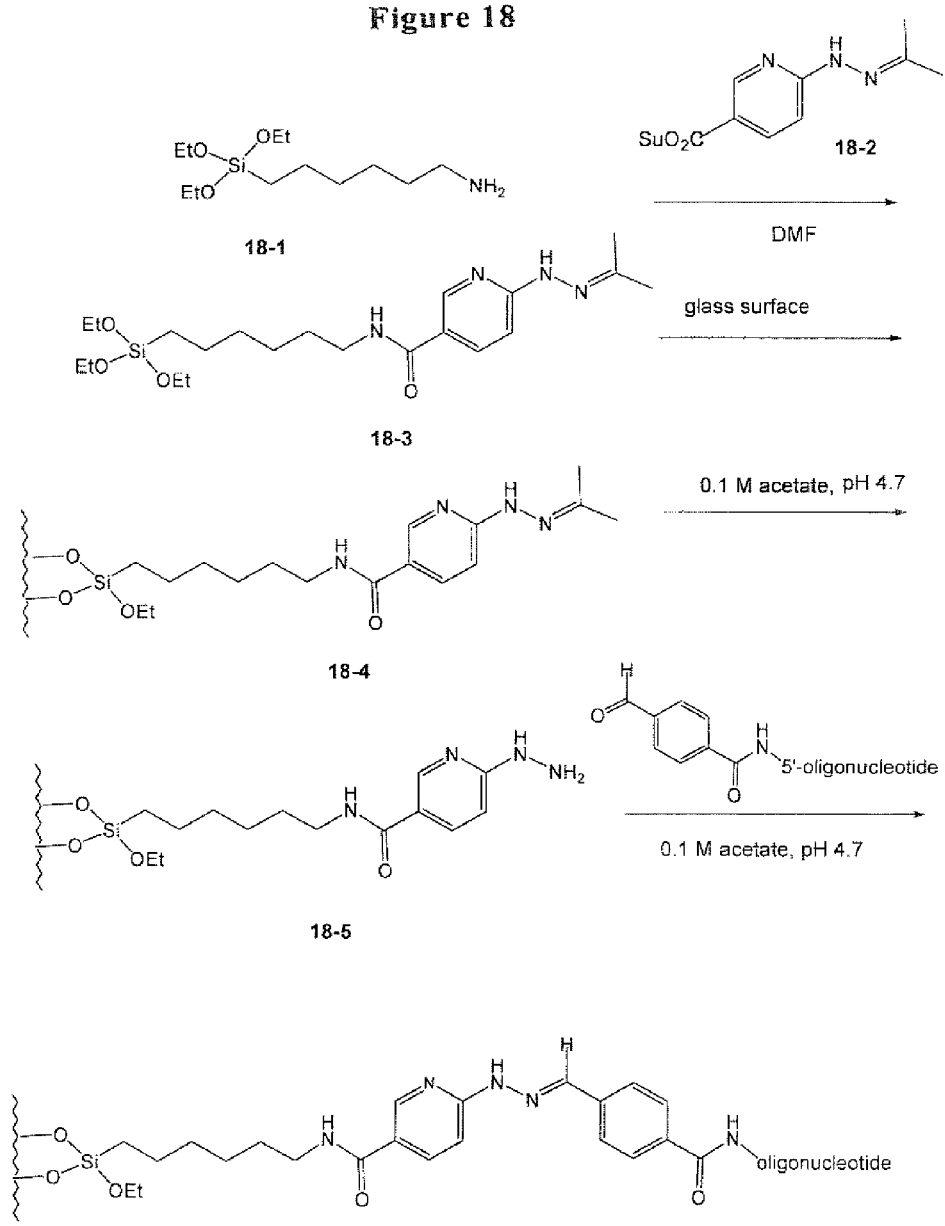
FIG. 18 illustrates the preparation of a hydrazino modified solid surface and immobilization of a carbonyl (e.g., aldehyde) modified oligonucleotide thereon.

Covalent Coupling of a 5'-Hydrazino-Substituted Oligonucleotide to a Carbonyl-Modified Silica-Based Surface As shown in FIG. 17, to a solution of 6-aminohexyltriethoxysilane (17-1; 1 equiv.; United Chemical Technologies, Bristol, Pa.) in tetrahydrofuran is added a solution of succinimidyl 4-formylbenzoate (1 equiv.) in tetrahydrofuran. The reaction mixture is allowed to incubate at room temperature until complete as monitored by silica gel chromatography. The solvent is removed under reduced pressure and the residue is chromatographed on silica gel. Fractions containing the product are pooled and concentrated to give the desired silane 17-2.

A 95% ethanol-5% water solution is adjusted to pH 4.5-5.5 with acetic acid. Silane 17-2 is added with stirring to yield a 2% final concentration. Five minutes is allowed for hydrolysis and silanol formation. The glass plates are dipped into the colution, agitated gently, and removed after 1-2 minutes. The plate is rinsed free of excess materials by dipping briefly in ethanol. Cure of the silane layer is 24 h at room temperature.

Incubation of a buffered, pH about 4 to about 9.6, solution of a 5'-hydrazino-oligonucleotide on aldehyde modified glass surface covalently couples the oligonucleotide to the surface.

EXAMPLE 10

Figure 16:
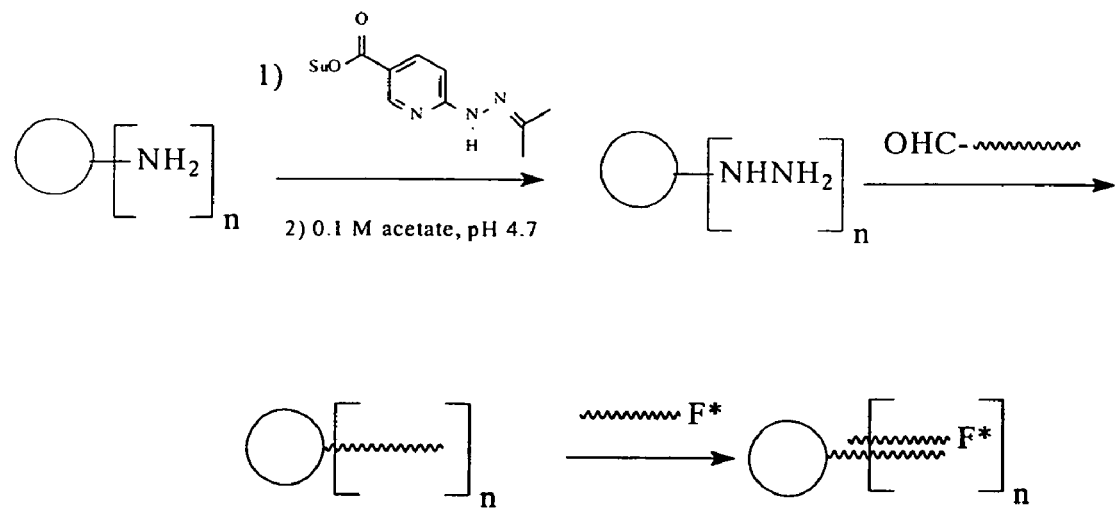
FIG. 16 illustrates the formation of hydrazino beads, immobilization of the aldehyde modified oligonucleotide of FIG. 5, and reaction of the immobilized oligonucleotide with its fluorescein modified complement 5'-fluorescein-cat ggc atc agt tac gct-3'.

Covalent Coupling of a 5'-Aldehyde-Oligonucleotide onto a Hydrazino-Modified Bead and Hybridization to its Fluorescent Complement As shown in FIG. 16, an aldehyde modified oligonucleotide is immobilized on a hydrazino modified bead. Hybridization to the oligonucleotide's fluorescent complement allows for identification of the sites of immobilization.

EXAMPLE 11

Colorimetric Assay for Analysis of Aldehyde Groups

5'-Aldehyde-modified oligonucleotide (Example 2) (3 µL of a 0.118 OD/µL solution in 0.1 M acetate, pH 4.7) was added to 0.5 mM 2-hydrazinopyridine (Aldrich Chemical Co., Milwaukee, Wis.) in 0.1 M acetate, pH4.7 (97 µL) and incubated at room temperature in the dark for 2-4 h. The absorbance of the sample was read at 360 nm (molar extinction coefficient at 360 nm for the hydrazone of 2-hydrazinopyridine and methyl 4-formylbenzoate is 18000).

EXAMPLE 12

Stability Assay Of 5'-Aldehyde Oligonucleotide i. Room Temperature Stability

Aliquots (6×0.1 Ods) of 5'-aldehyde-modified oligonucleotide (Example 2) were placed in 0.6 mL Eppendorf tubes and allowed to stand at room temperature. At specific intervals, samples were analyzed according to the assay method of Example 11. The aldehyde-modified oligonucleotide is completely stable for 45 days at ambient temperature in water.

ii. Elevated Temperature Stability

Aliquots (15×0.56 Ods) of 5'-aldehyde-modified oligonucleotide (Example 2) were dissolved in deionized water (10 µL) and were placed in 1.5 mL Eppendorf tubes. The solutions were incubated at 25° C., 55° C. and 80° C. for 6, 24, 48, 72 and 96 hours. The samples were analyzed according to the assay method of Example 11. Results indicated no loss of reactivity of the aldehyde functionality.

EXAMPLE 13

Reactivity Assay of Aldehyde Function on 5'-Aldehydo-Oligonucleotide

An aliquot of the aldehyde-oligonucleotide of Example 2 (1.0 Ods; 0.2 OD/µL) was suspended in 0.1 M acetate, pH 4.7. To the oligonucleotide solution was added transhydrazinostilbene (1 µL of a 2.5 mg/mL solution in DMF; 3 equivalents). The reaction mixture was incubated at room temperature for 2 h and analyzed by polyacrylamide electrophoresis (15% crosslink). The gel indicated complete conjugation conversion of 5'-aldehyde function to hydrazone.

EXAMPLE 14

A. Preparation of 4-Formylbenzamide Modified Beads

Amino beads (714 µL; Bangs Laboratories, Fishers, Ind.; mean diameter (0.87 µm; density of solid polymer 1.06 g/mL; surface titration 245 µeq/g; number of spheres/gram 2.736e12) were solvent exchanged by centrifugation, removal of supernatant and washing with conjugation buffer (100 mM phosphate, 150 mM NaCl, pH 7.4) three times (1.0 mL). A solution of succinimidyl 4-formyl benzoate (10 mg; 0.04 mmol) in DMF (50 µL) was added to a suspension of the beads in conjugation buffer and the reaction mixture was placed on a rotator overnight. The beads were purified by centrifugation, removal of the supernatant and washing with DI water (3×1000 µL).

B. Preparation of 6-Hydrazinonicotinamide Modified Beads

Amino beads (0.245 mL) were prepped as in Example 14A in conjugation buffer. A solution of succinimidyl 6-acetone hydrazinonicotinate hydrazone (SANH; 7 mg) in DMF (50 µL) was prepared. The beads were resuspended in conjugation buffer and SANH/DMF solution (40 µL) was added. The beads were purified by centrifugation, removal of supernatant, washed with conjugation buffer (2×1 mL) and 0.1 M acetate buffer, pH 4.7 (2×1.0 mL) to deprotect the hydrazine.

C. Conjugation of Aldehyde Modified Oligonucleotide to 6-Hydrazinonicotinamide Beads To a suspension 6-hydrazinonicotinamide modified beads (0.5 mg) in 0.1 M acetate buffer, pH 4.7 (7.2 µL) was added 5'-n ttt ttt tag cct aac tga tgc cat g-3' (n=6-(4-formylbenzoylamino)hexyl phosphodiester, 5'-aldehyde modified oligonucleotide) prepared as described in Example 2 (14.5 µL of a 0.92 OD/µL solution) in acetate buffer. The suspension was placed on the rotator overnight. The beads were centrifuged and the supernatant discarded. The beads were washed with hybridization buffer (50 mM tris, 0.5 M NaCl, 0.1% tween; 3×500 µL).

D. Hybridization Protocol

A solution of 5'-fluorescein-cat ggc atc agt tac gct (SEQ ID NO:3) ($7.24e^{-5}$ OD) in hybridization buffer (1000 µL) was prepared. To the oligo-modified beads was added above fluorescent oligo (100 µL) and the tubes were placed on the rotator overnight. The beads were centrifuged and the supernatant discarded. The beads were washed with hybridization buffer (2×400 µL) at room temperature and at 40° C. for 30 min (2×400 µL). The beads were examined for fluorescence using a Beckman Coulter Fluorescent Activated Cell Sorter by examining 100,000 beads/sample. The beads (amino, hydrazino and oligonucleotide) showed little or no fluorescence, while the hybridized beads showed fluorescence of greater than 350.

EXAMPLE 15

Preparation of a 5'-N-MMT-Aminooxy-Substituted Oligonucleotide

A. 6-O-hydroxylaminonicotinic acid (14-2) and 6-N-hydroxylaminonicotinic acid (11-3)

Figure 11:
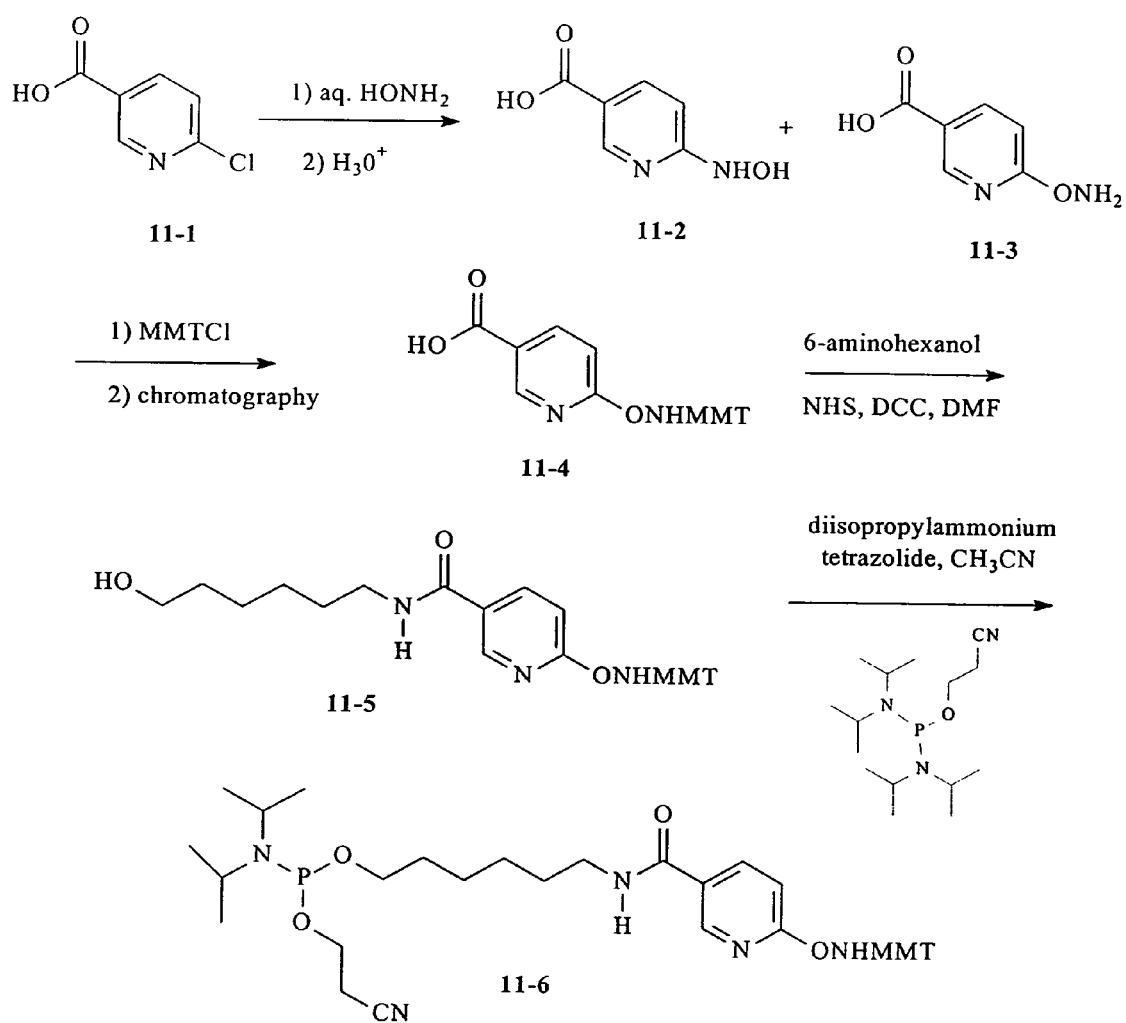
FIG. 11 illustrates the synthesis of a monomethoxytrityl (MMT) protected oxyamino phosphoramidite provided herein.

As shown in FIG. 11, a solution of hydroxylamine.HCl (Aldrich Chemical Co.) in water is basified to pH 10 with 10 M sodium hydroxide. 6-Chloronicotinic acid (11-1) is added to the hydroxylamine solution heated at 95° C. for 16 hours. The solvent is removed under reduced pressure and water is added and the solution acidified with conc. HCl leading to the formation of a precipitate. The precipitate is isolated by filtration, washed with ethanol and dried under vacuum to give a mixture of 11-2 and 11-3.

B. 6-O-MMT-hydroxylaminonicotinic acid (11-4)

The solids are dissolved in DMF and treated with triethylamine and monomethoxytrityl chloride. The reaction mixture is stirred at room temperature for 4 hours and the solvent removed under reduced pressure. The residue is chromatographed on silica gel and the fractions containing the desired product are combined and concentrated yielding a solid product 11-4.

C. 6-O-MMT-hydroxylamino-(6-hydroxylhexyl)-nicotinamide (11-5)

The N-MMT product 11-4 (1 equiv) is dissolved in DMF and N-hydroxysuccinimide (1 equiv) and 6-aminohexanol are added followed by the dropwise addition of a solution of dicyclohexylcarbodiimide (1 equiv). The reaction mixture is stirred at room temperature and the progress of the reaction is followed by TLC. Dicyclohexylurea solids are removed by filtration and the filtrate is concentrated under reduced pressure. The residue is treated with ethyl acetate and insolubles are removed by filtration. The filtrate is concentrated to dryness under reduced pressure and the product 11-5 is isolated by silica gel chromatography. Alcohol 11-5 is converted into its phosphoramidite 11-6 as described in Example 3.

EXAMPLE 16

Hydrazine Modification of Cellulose and Conjugation to 5'-Aldehyde Oligonucleotide A shown in FIG. 12, to a solution of 1,6-hexanediamine (1 equiv; Aldrich Chemical Co.) in THF is added dropwise a solution of succinimidyl 6-BOC-hydrazinonicotinate (12-1; 2 equiv) in THF. The reaction mixture is stirred at room temperature for 4 hours. The solvent is removed under reduced pressure and the product 12-2 is purified by silica gel chromatography.

Cellulose is activated by immersion in a solution of 1-cyano-4-dimethylaminopyridine bromide (Research Organics, Cleveland, Ohio; see Lees et al. (1996) *Vaccine* 14:190) for 30 seconds, followed by basification with 0.2 M triethylamine. At t=2.5 min a solution of 0.1 M dihydrazine 12-2 is added and the reaction allowed to stand at room temperature overnight. The cellulose is washed in DI water three times.

A solution of 5'-aldehyde modified oligonucleotide (as prepared in Example 2; 0.2 OD/μL in 0.1 M acetate buffer, pH 4.7) is spotted (1 μL) on the hydrazino-modified cellulose. The spot is allowed to stand until dry and washed with hybridization buffer (50 mM tris, 0.5 M NaCl, 1% tween, pH 7.4).

The modification is analyzed for successful modification by hybridization to the immobilized oligonucleotide's 5'-modified complement. The hybridization is performed by spotting a 0.2 OD/mL solution of the complementary oligonucleotide in hybridization buffer (1 μL) and incubation at room temperature until fry. The membrane is washed with hybridization buffer and visualized using a fluorescent microscope.

EXAMPLE 17

Preparation of an FMOC-Protected Hydrazinonicotinamide Phosphoramidite Monomer

A. 1-($N^2$-Fluorenylmethyloxycarbonyl)hydrazino-nicotinamidohexanol (7-2)

Figure 7:
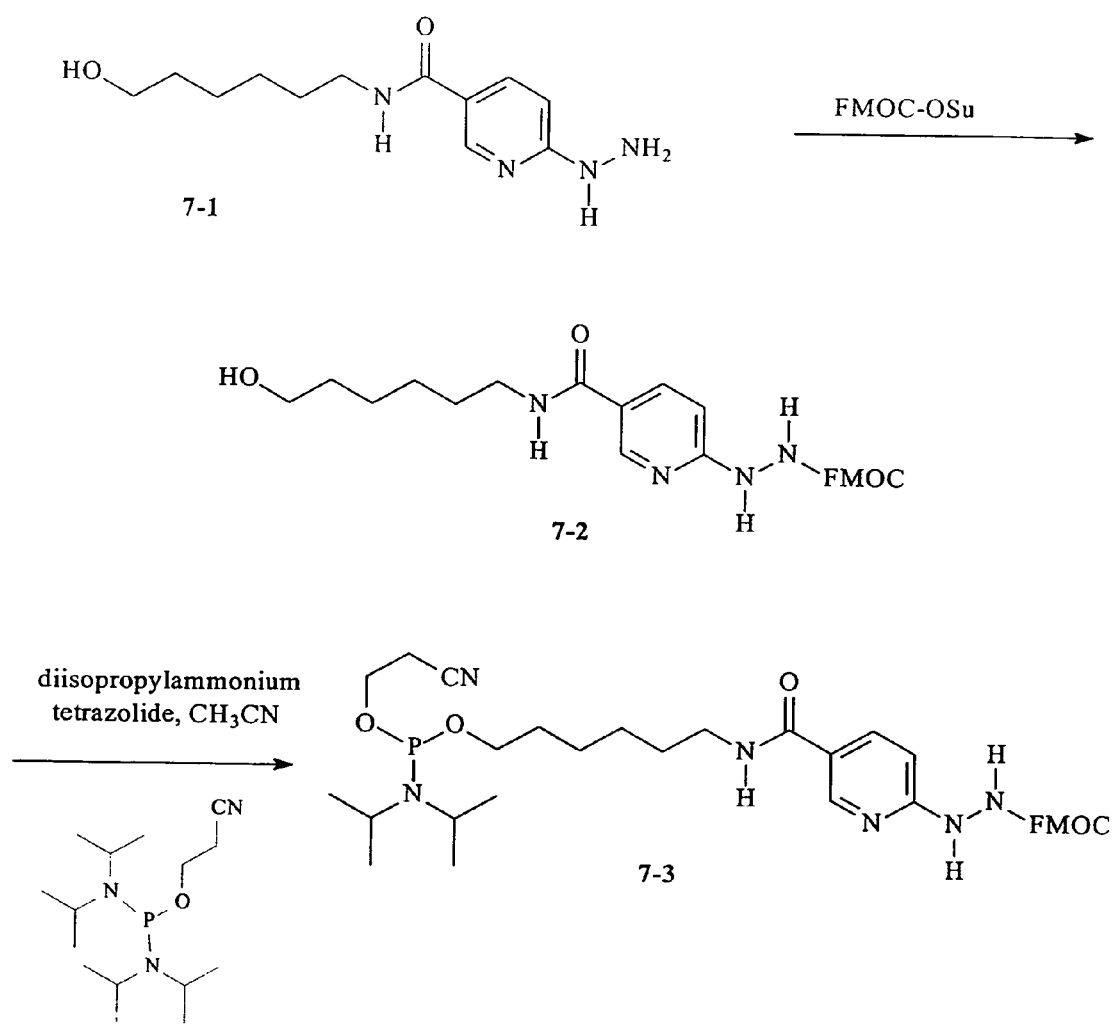
FIG. 7 illustrates the synthesis of a 9-fluorenylmethoxycarbonyl (FMOC)-protected hydrazino phophoramidite monomer provided herein.

As shown in FIG. 7, hydrazinonicotinamidohexanol (7-1; 1.9 g, 6.84 mmole) was dissolved in water/methanol (2:1) and 2.2 g (6.84 mmole, 1 eq) of FMOC-O—Su was added and stirred at room temperature for 3 hours. Further acetonitrile was added to dissolve precipitate. The reaction mixture was evaporated and re-dissolved in methanol. On standing a precipitate formed. The precipitate was filtered and dried under vacuum to give 7-2 (1.9 grams; 60% yield). The structure of the product was confirmed by $^1$H NMR.

B. 2-Cyanoethyl-N,N-diisopropylphosphoramidite of 1-($N^2$-fluorenylmethyloxycarbonyl)hydrazino-nicotinamidohexanol (7-3)

1-($N^2$-fluorenylmethyloxycarbonyl)hydrazino-nicotinamidohexanol (1.0 g, 1.89 mmole) was dissolved in 20 ml acetonitrile and 0.181 g (1.06 mmole, 0.5 eq.) of diisopropylammonium tetrazolide was added followed by the addition of 0.762 g (1.2 eq.) of 2-cyanoethyl-N,N,N',N'-tetraisopropylphosphordiamidite. The reaction mixture was stirred at room temperature for 3 hours. The reaction was analyzed by TLC on silica gel using ethyl acetate/hexane (1:1) with 5% triethylamine. The mixture was dried down and redissolved in 5 ml of ethyl acetate and purified on a 20 grams silica gel with ethyl acetate hexane.

EXAMPLE 18

Preparation of an DMT-Protected Hydrazinonicotinamide Phosphoramidite Monomer

A. 6-$N^2$-dimethoxytrityl-hydrazinonicotinic acid (6-2)

Figure 6:
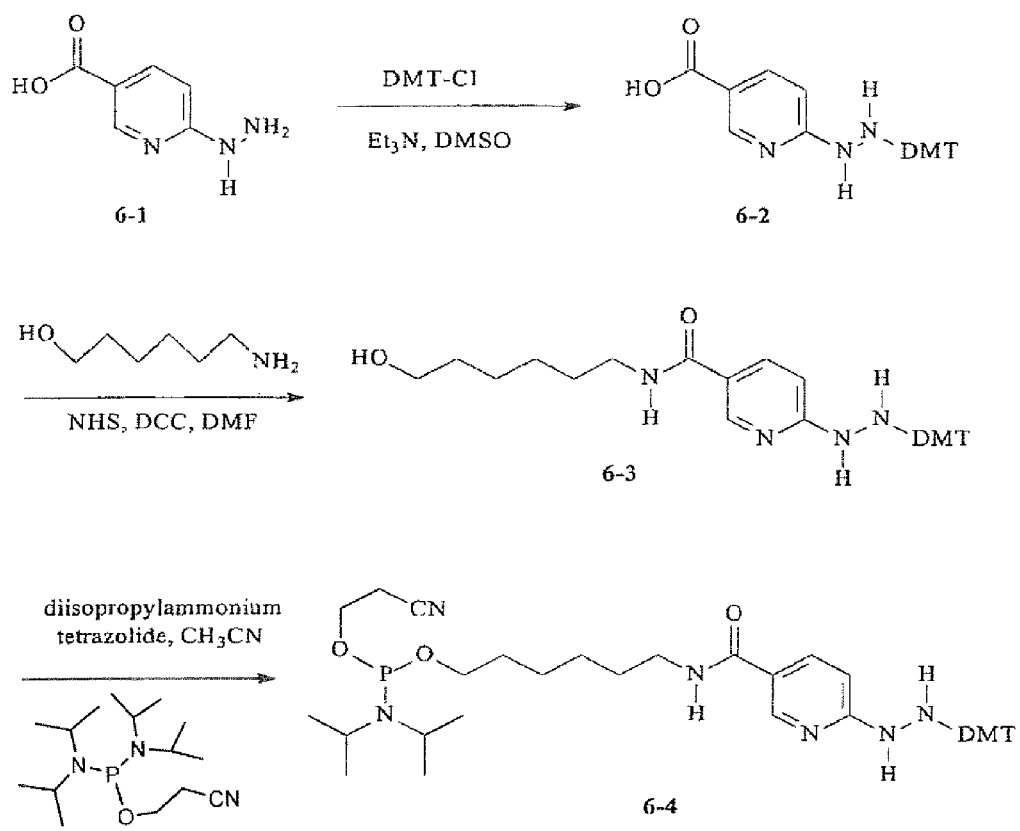
FIG. 6 illustrates the synthesis of a dimethoxytrityl (DMT)-protected hydrazino phophoramidite monomer provided herein (see, Example 4).

As shown in FIG. 6, hydrazinonicotinic acid (6-1; 5.0 g, 32.64 mmole) was co-evaporated with anhydrous pyridine (2×30 ml) and dissolved in 30 ml of dichloromethane. The solution was cooled in an ice bath and triethylamine (3.96 g; 39.2 mmole) was added. Dimethoxytrityl chloride (8.85 g, 26.14 mmole, 0.8 eq) was dissolved in 30 ml of dichloromethane and added and stirred at room temperature overnight. Anhydrous pyridine (10 ml) was added to dissolve any insolubles. After 3 hours the TLC of the reaction shows about 70% conversion to DMT-protected hydrazine product. The reaction mixture extracted with of sat. $NaHCO_3$ (30 ml). The organic layer was dried ($Na_2SO_4$) and filtered. The solution was evaporated and redissolved in dichloromethane (20 mL) and poured into hexanes (200 mL). The solution was placed in the freezer overnight yielding a solid. The product was filtered and dried to give desired product (7.03 g; 60% yield). The structure of the product 6-2 was confirmed by $^1$H NMR.

B. 1-(6-$N^2$-dimethoxytrityl)hydrazino-nicotinamidohexanol (6-3)

1-($N^2$-dimethoxytrityl)hydrazino-nicotinic acid (6-2; 2.0 g, 4.39 mmole) was suspended in 30 ml of ethyl acetate and 0.99 g (4.83 mmole) of dicyclohexylcarbodiimide (DCC) and 0.5 g (4.39 mmole) of N-hydroxysuccinimide was added. Reaction was allowed to stir at RT overnight. TLC on silica gel plate showed disappearance of the starting material and formation of one major product. The precipitated dicyclohexylurea was filtered off and washed with ethyl acetate. The combined filtrates were evaporated to dryness and redissolved in 5 ml dichloromethane and 40 ml of ethyl alcohol was added. The product was allowed to crystallize in the freezer. The crystals were filtered and dried to obtain 6-3 (1.7 g; 71% yield).

C. 2-Cyanoethyl-N,N-diisopropylphosphoramidite of 1-($N^2$-dimethoxytrityl)hydrazino-nicotinamidohexanol (6-4)

1-($N^2$-Dimethoxytrityl)hydrazino-nicotinamidohexanol (6-3; 1.0 g, 0.19 mmole) was dissolved in acetonitrile (20 mL) and of diisopropylammonium tetrazolide (0.181 g; 1.06 mmole, 0.5 eq.) was added, followed by the addition of 2-cyanoethyl-N,N,N',N'-tetraisopropylphosphordiamidite (0.762 g, 1.2 eq.). The reaction mixture was stirred at room temperature for 3 hours. The reaction was analyzed by TLC on silica gel using ethyl acetate/hexane (1:1) with 5% triethylamine. The mixture was evaporated, redissolved in 5 ml of ethyl acetate and purified on a 20 grams silica gel. The column was packed with ethyl acetate/hexane (1:1) with 5% triethylamine and washed with the same solvent but only 1% triethylamine. The product was eluted with ethyl acetate/hexane (1:1). The product fractions were pooled and dried to obtain 400 mg of 6-4. The structure was analyzed by $^1$H NMR and $^{31}$P NMR.

EXAMPLE 19

Figure 19:
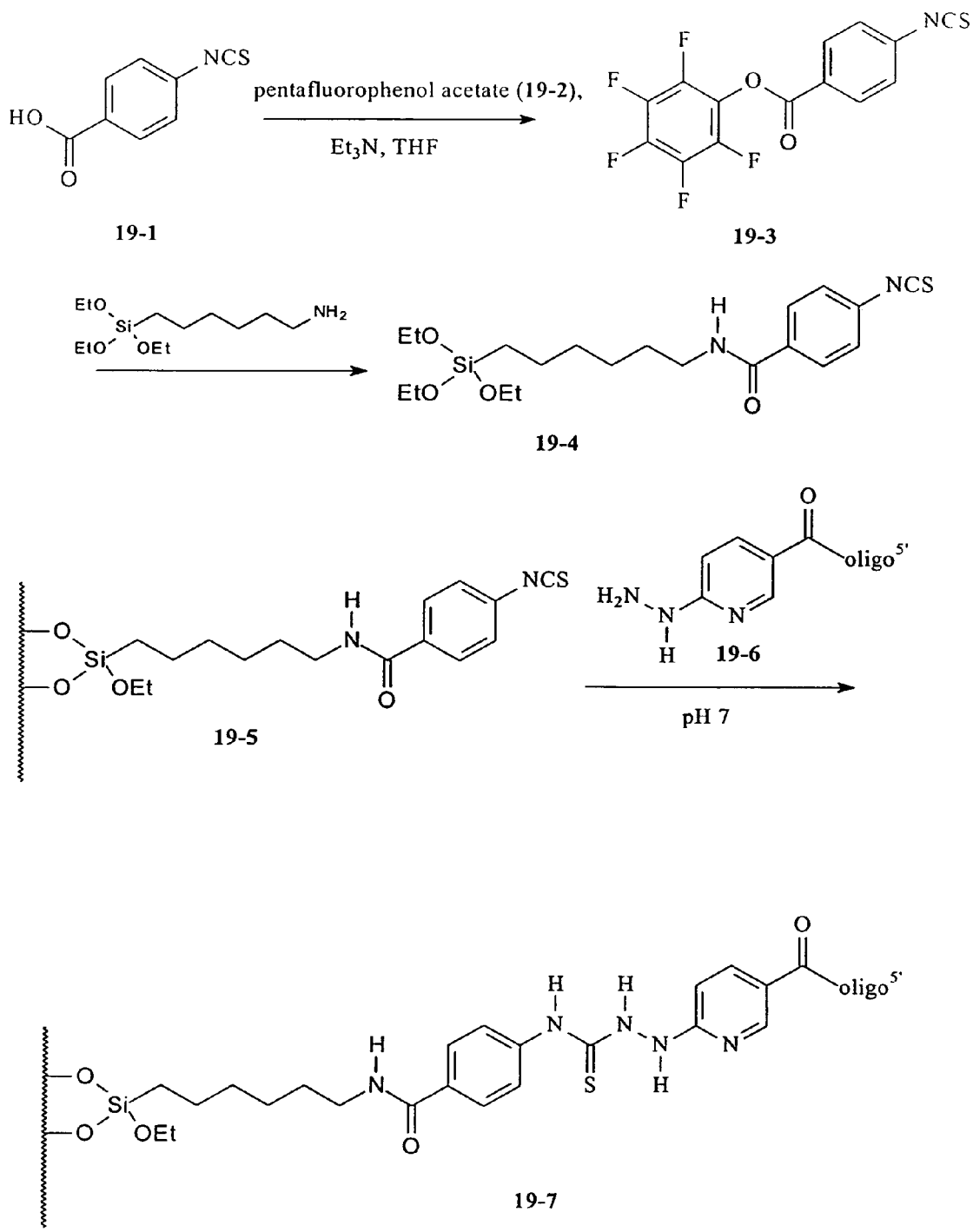
FIG. 19 shows the preparation of an isothiocyanato modified solid surface and conjugation of a hydrazino modified oligonuceotide thereto.
Figure 20:
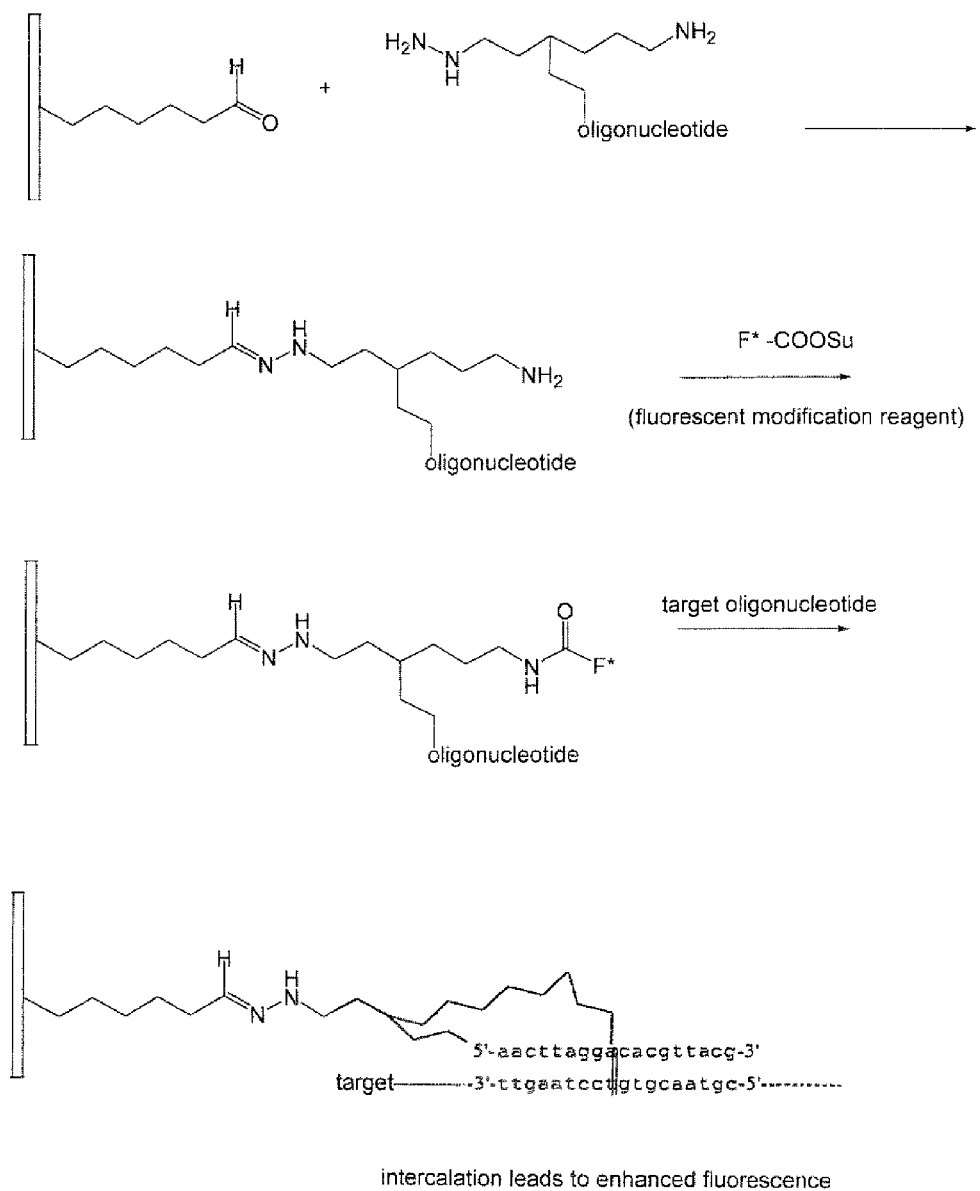
FIG. 20 illustrates the immobilization of a hydrazino modified oligonucleotide onto an aldehyde modified solid surface. The hydrazino modified oligonucleotide (e.g., modified SEQ ID NO:4) possesses an amino group for incorporation of a fluorescent modification reagent that, upon hybridization with a target oligonucleotide (e.g., SEQ ID NO:5), intercalates into the hybridized complex, leading to enhanced fluorescence.

Covalent Coupling of a 5'-Hydrazino-Substituted Oligonucleotide to a Isothiocyanate-Modified Silica-Based Surface As shown in FIG. 19, to a solution of 4-isothiocyanatobenzoic acid (19-1; 2.0 g; 11.1 mmol; 1 equiv; TransWorld Chemicals, Gaithersburg, Md.) in THF (30 mL) was added pentafluorophenol acetate (19-2; 2.11 mL; 12.2 mmol; 1.1 equiv; Aldrich Chemicals). To the slightly cloudy reaction mixture, triethylamine (3.1 mL; 2.0 equiv) was added. TLC (ethyl acetate) indicated the reaction was complete within 30 min. The solvent was removed on the rotavap to give a white solid. The solids were treated with hexanes/ethyl acetate (1/1) and the solids were isolated by filtration to give desired ester 19-3 (0.92 g). The structure was confirmed by $^1$H NMR.

To a solution of 6-aminohexyltriethoxysilane (1 equiv.; United Chemical Technologies, Bristol, Pa.) in tetrahydrofuran is added a solution of 19-3 (1 equiv.) in tetrahydrofuran. The reaction mixture is allowed to incubate at room temperature until complete as monitored by silica gel chromatography. The solvent is removed under reduced pressure and the residue is chromatographed on silica gel. Fractions containing the product are pooled and concentrated to give the desired silane 19-4.

A 95% ethanol-5% water solution is adjusted to pH 4.5-5.5 with acetic acid. Silane 19-4 added with stirring to yield a 2% final concentration. Five minutes is allowed for hydrolysis and silanol formation. The glass plates are dipped into the solution, agitated gently, and removed after 1-2 minutes. The plate is rinsed free of excess materials by dipping briefly in ethanol. Cure of the silane layer is 24 hours at room temperature to give 19-5.

Incubation of a buffered, pH 7.0-7.4 solution of a 5'-hydrazino-oligonucleotide on isothiocyante modified glass surface covalently couples the oligonucleotide to the surface.

EXAMPLE 20

Preparation of a Hydrazino Cytosine Amidite

As shown in FIG. 13, 3-(5-trifluoroacetamido)propynyl-cytosine (13-1; 1 equiv), prepared following the procedure of U.S. Pat. No. 5,151,507) is treated with a solution of ammonium hydroxide in acetone for 30 min at room temperature. The volatiles are removed under reduced pressure and dissolved in 0.1 M phosphate buffer, pH 7.4. An equal volume of dioxane is added followed by the dropwise addition of a solution of succinimidyl 6-FMOC-hydrazinonicotinate (1.2 equiv). The reaction mixture is stirred at room temperature for 3 hours. The dioxane is removed under reduced pressure and the aqueous residue is extracted twice with ethyl acetate. The combined organic extracts are dried (magnesium sulfate), filtered and concentrated to give 13-2.

Amino diol 13-2 (1 equiv) is co-evaporated from DMF and redissolved in DMF and treated with hexamethyldisilazine (1 equiv) and stirred until the reaction is complete as determined by TLC (1 hour). To the resulting mixture a solution of benzoic anhydride (2 equiv) and triethylamine (2 equiv) are added and the reaction mixture is stirred at room temperature until the reaction is complete as determined by TLC. The silyl groups are removed by addition of methanol/water (1/1) over one hour. The solvents were removed under reduced pressure and the residue is dissolved in ethyl acetate and washed with saturated aqueous sodium bicarbonate and brine. The organic phase is dried over magnesium sulfate, filtered and concentrated to give the desired diol. The diol is coevaporated twice from DMF and redissolved in DMF and a solution of dimethoxytritylchloride (1.1 equiv) in 1/1 DMF is added dropwise over 1 h. The reaction mixture is stirred until complete as determined by TLC. The solvent were removed under reduced pressure and the residue is dissolved in ethyl acetate and washed with saturated sodium bicarbonate and brine. The organic phase is dried (magnesium sulfate), filtered and concentrated under reduced pressure to give 13-3.

Alcohol 13-3 was converted to its amidite 13-4 using the general procedure for preparation of amidites described in Example 3.

EXAMPLE 21

Preparation of an Aldehyde Cytosine Amidite

As shown in FIG. 15, 3-(5-trifluoroacetamido)propynyl-cytosine (15-1; 1 equiv), prepared according to the procedure of U.S. Pat. No. 5,151,507, is treated with a solution of ammonium hydroxide in acetone for 30 min at room temperature. The volatiles are removed under reduced pressure and dissolved in 0.1 M phosphate buffer, pH 7.4. An equal volume of dioxane is added followed by the dropwise addition of a solution of 4-formylbenzoate (1 equiv). The reaction mixture is stirred at room temperature for 3 hours. The dioxane is removed under reduced pressure and the aqueous residue is extracted twice with ethyl acetate. The combined organic extracts are dried (magnesium sulfate), filtered and concentrated to give 15-2.

Aldehyde 15-2 (1 equiv) is coevaporated from pyridine and redissolved in pyridine and treated with hexamethyldisilazine (1 equiv) and stirred until the reaction is complete as determined by TLC-1 hour. To the resulting mixture a solution of benzoic anhydride (2 equiv) are added and the reaction mixture is stirred at room temperature until the reaction is complete as determined by TLC. The silyl groups are removed by addition of methanol/water (1/1) over one hour. The solvents were removed under reduced pressure and the residue is dissolved in ethyl acetate and washed with saturated aqueous sodium bicarbonate and brine. The organic phase is dried over magnesium sulfate, filtered and concentrated to give 15-3. 15-3 is coevaporated twice from pyridine and redissolved in pyridine and a solution of dimethoxytrityl chloride (1.1 equiv) in 1/1 didchloromethane/pyridine is added dropwise over 1 h. The reaction mixture is stirred until complete as determined by TLC. The solvent were removed under reduced pressure and the residue are dissolved in ethyl acetate and washed with saturated sodium bicarbonate and brine. The organic phase is dried (magnesium sulfate), filtered and concentrated under reduced pressure to give 15-3.

Alcohol 15-3 was converted to its amidite 15-4 using the general procedure for preparation of amidites described in Example 3.

EXAMPLE 22

Preparation of a Fluorophore Containing Amidite

As shown in FIG. 21, 6-(N-dimethoxytrityl)hydrazinonicotinic acid 21-1 (1 equiv.; as prepared in Example 18) is dissolved was dissolved in DMF and N-hydroxysuccinimide (1 equiv.) was added followed by the dropwise addition of a solution of dicyclohexylcarbodiimide (DCC) (1.0 equiv.) in DMF. The reaction mixture was stirred at room temperature for three hours. Dicyclohexylurea (DCU) precipitate was removed by filtration and the filtrate was concentrated to a viscous oil. The oil was treated with ethyl acetate and further DCU was removed by filtration. The filtrate was concentrated to give desired ester 21-2.

A solution of N-ε-FMOC lysine (1 equiv.) and triethylamine (1.2 equiv) in DMF is added dropwise to a solution of 21-2 (1 equiv) in DMF. The reaction mixture is stirred at room temperature overnight at room temperature. The solvent is removed under reduced pressure and the residue is dissolved in ethyl acetate and washed with 5% citric acid and brine. The organic phase is dried over magnesium sulfate, filtered and concentrated. The product 21-3 is isolated by silica gel chromatography.

To a solution of 21-3 (1 equiv.), N-hydroxysuccinimide (NHS) (1 equiv.) and 6-aminohexanol (1 equiv.) in DMF is added a solution of DCC (1 equiv.) in DMF. The reaction mixture is stirred at room temperature for 3 hours. The product 21-4 is isolated in a manner similar to the protocol for the purification of 21-2.

10-Carboxyethyl-2,7-biscarboethoxyamino-9-phenylphenanthridine (22-2)

2,7-Biscarboethoxyamino-9-phenylphenanthridine (22-1, 1 equiv.), prepared by the method of Watkins (1952) *J. Chem. Soc.* 3059, is combined with 3-bromopropionic acid (2.5 equiv.; Aldrich Chemical Co., Milwaukee, Wis.) and is heated in nitrobenzene at 100° C. for 4-6 hours. Following cooling to room temperature the crude product is precipitated by addition of ether. The product 22-2 is isolated by filtration and used directly.

Succinimidyl 10-carboxyethyl-2,7-biscarbiethoxyamino-9-phenylphenanthridine (22-3)

To a solution of 22-2 (1 equiv) in DMF is added N-hydroxysuccinimide (1.1 equiv) and a solution of dicyclohexylcarbodiimide (1.0 equiv). The reaction mixture is stirred at room temperature for 4 hours. The precipitated solids (dicyclohexylurea) are removed by filtration and the filtrate is concentrated to dryness and the product 22-3 is isolated by silica gel chromatography.

To a solution of 21-4 in DMF is a added dropwise a solution of fluorophore succinimidyl ester 22-3 in DMF. The reaction mixture is stirred at room temperature for 3 hours and the solvent removed under reduced pressure. The product 21-6 is isolated by reverse phase HPLC chromatography.

Alcohol 21-6 is converted into its amidite 21-7 using the general procedure for preparation of amidites described in Example 3.

Amidite 21-7 is incorporated onto the 5'-terminus of an oligonucleotide using the procedure of Example 4.

Since modifications will be apparent to those of skill in this art, it is intended that this invention be limited only by the scope of the appended claims.

What is claimed is:

1. A compound that has formula (I):

$$P^1\text{-M-X}$$

wherein:
- $P^1$ is a phosphorous based coupling group selected from the group consisting of phosphoramidite, H-phosphonate and phosphotriester;
- X is selected from the group consisting of: —NHNH—$R^4$, —NHN=C(CH$_3$)$_2$, —(C=O)CH$_3$, —(C=O)H and —ONHR$^4$
wherein $R^4$ is a protecting group; and
- M is a divalent group of the formula —(CH$_2$)$_n$—NH—(C=R$^1$)—R$^2$— wherein $R^1$ is S or O; $R^2$ is pyrimidinyl group, a quinolinyl group or a pyrrolyl group; and n is 2, 3, 4, 5, 6, 7, 8, 9, or 10.

2. The compound of claim 1, wherein $R^4$ is a protecting group selected from the group consisting of monomethoxytrityl (MMT), dimethoxytrityl (DMT), 9-fluorenylmethoxycarbonyl (FMOC) and trifluoroacetyl (TEA).

3. The compound of claim 1 wherein X is —NHNH—$R^4$.

4. The compound of claim 1 wherein X is —NHN=C(CH$_3$)$_2$.

5. The compound of claim 1 wherein X is —(C=O)CH$_3$.

6. The compound of claim 1 wherein X is —(C=O)H.

7. The compound of claim 1 wherein X is —ONR$^4$.

8. The compound of claim 1 wherein $R^4$ is MMT.

9. The compound of claim 1 wherein $R^4$ DMT.

10. The compound of claim 1 wherein $R^4$ FMOC.

11. The compound of claim 1 wherein $R^4$ is TFA.

* * * * *